(12) United States Patent
Korkaya et al.

(10) Patent No.: US 10,722,528 B2
(45) Date of Patent: Jul. 28, 2020

(54) COMPOSITIONS AND METHODS FOR INHIBITING METASTASIS

(71) Applicant: Augusta University Research Institute, Inc., Augusta, GA (US)

(72) Inventors: Hasan Korkaya, Martinez, GA (US); Eunmi Lee, Augusta, GA (US)

(73) Assignee: Augusta University Research Institute, Inc., Augusta, GA (US)

( * ) Notice: Subject to any disclaimer, the term of this patent is extended or adjusted under 35 U.S.C. 154(b) by 0 days.

(21) Appl. No.: 16/366,469

(22) Filed: Mar. 27, 2019

(65) Prior Publication Data

US 2019/0298746 A1   Oct. 3, 2019

Related U.S. Application Data

(60) Provisional application No. 62/649,301, filed on Mar. 28, 2018.

(51) Int. Cl.

| | |
|---|---|
| *C07D 209/94* | (2006.01) |
| *A61K 31/404* | (2006.01) |
| *A61P 35/04* | (2006.01) |
| *A61K 31/675* | (2006.01) |
| *C07C 49/84* | (2006.01) |
| *A61K 31/122* | (2006.01) |

(52) U.S. Cl.
CPC .......... *A61K 31/675* (2013.01); *A61K 31/122* (2013.01); *A61K 31/404* (2013.01); *A61P 35/04* (2018.01); *C07C 49/84* (2013.01); *C07D 209/94* (2013.01)

(58) Field of Classification Search
CPC .. C07D 209/94; A61K 31/404; A61K 31/675; A61P 35/04
USPC .......................................... 548/416; 514/410
See application file for complete search history.

(56) References Cited

U.S. PATENT DOCUMENTS

| 5,013,556 A | 5/1991 | Woodle | |
|---|---|---|---|
| 5,190,929 A | 3/1993 | Borch | |
| 2016/0361311 A1* | 12/2016 | Al-Olaby | ........... A61K 31/5513 |

OTHER PUBLICATIONS

PubChem Compound CID 243149, Create Date Mar. 26, 2005.*
Argyris et al. Journal of Dental Research 97(6), 674-682, 2018.*
Shabani et al. Inflamm. Res, 67(10), 801-802, 2018.*
Cecil Textbook of Medicine, edited by Bennet, J.C., and Plum F., 20th edition,vol. 1, 1004-1010, 1996.*
Freshney et al.,Culture of Animal Cells, A Manual of Basic Technique, Alan R. Liss, Inc., 1983, New York, p. 4.*
Dermeret al., Bio/Technology, 1994, 12:320.*
Olub et al., Science, 286, 531-537, 1999.*
Abuchowski, Abraham et al., "Soluble Polymer-Enzyme Adducts," in Enzymes as Drugs. Hocenberg and Roberts, eds. Wiley-Interscience: New York, N. Y., pp. 367-383 (1981).
Aslakson, Cheryl J. et al., "Selective Events in the Metastatic Process Defined by Analysis of the Sequential Dissemination of Subpopulations of a Mouse Mammary Tumor", Cancer Res, 52:1399-1405 (1992).
Chikaishi, Yasuhiro et al., "The EMT Status in the Primary Tumor Does Not Predict Postoperative Recurrence or Disease-Free Survival in Lung Adenocarcinoma", Anticancer Res, 31:4451-4456 (2011).
Condamine, Thomas et al., "Regulation of Tumor Metastasis by Myeloid-Derived Suppressor Cells", Annu Rev Med, 66:97-110 (2015).
Ding, Zhi-Chun et al., "Chemotherapy-Induced Myeloid Suppressor Cells and Antitumor Immunity: The Janus Face of Chemotherapy in Immunomodulation", Oncoimmunology, 3:8, e954471 (2014).
Erin, N. et al., "Bidirectional Effect of CD200 on Breast Cancer Development and Metastasis, with Ultimate Outcome Determined by Tumor Aggressiveness and a Cancer-Induced Inflammatory Response", Oncogene, 34:3860-3870 (2015).
Fidler, I.J. et al., "Metastasis Results from Preexisting Variant Cells within a Malignant Tumor", Science, 197:893-895 (1977). (Abstract Only).
Fidler, Isaiah J. et al., "Tumor Heterogeneity and the Biology of Cancer Invasion and Metastasis", Cancer Res, 38:2651-2660 (1978).
Gargett, Tessa et al., "GM-CSF Signalling Blockage and Chemotherapeutic Agents Act in Concert to Inhibit the Function of Myeloid-Derived Suppressor Cells in vitro", Clin Transl Immunology, 5(12): e119 (2016).
Grűnert, Stefan et al., "Diverse Cellular and Molecular Mechanisms Contribute to Epithelial Plasticity and Metastasis", Nat Rev Mol Cell Biol, 4:657-665 (2003).
Hűsemann, Yves et al., "Systemic Spread is an Early Step in Breast Cancer", Cancer Cell, 13:58-68 (2008).
Kaur, Punit et al., "A Mouse Model for Triple-Negative Breast Cancer Tumor-Initiating Cells (TNBC-TICs) Exhibits Similar Aggressive Phenotype to the Human Disease", BMC Cancer, 12:120 (2012).
Kim G. et al., "SOCS3-Mediated Regulation of Inflammatory Cytokines in PTEN and p53 Inactivated Triple Negative Breast Cancer Model", Oncogene, 34:671-680 (2015).
Klein, C.A., "Parallel Progression of Primary Tumours and Metastases", Nat Rev Cancer, 9(4) 302-312 (2009). (Abstract Only).
Liang, J. et al., "Design of New Oxazaphosphorine Anticancer Drugs", Curr Pharm Des, 13(9):963-978 Review (2007). (Abstract Only).
Marotta, Lauren L.C. et al., "The JAK2/STAT3 Signaling Pathway is Required for Growth of CD44+CD24− Stem Cell-Like Breast Cancer Cells in Human Tumors", J Clin Invest, 121(7):2723-2735 (2011).

(Continued)

*Primary Examiner* — Venkataraman Balasubramanian
(74) *Attorney, Agent, or Firm* — Smith, Gambrell & Russell, LLP

(57) ABSTRACT

Calprotectin inhibitors and derivatives thereof, and methods of using them for inhibiting or reducing metastatis and treating cancer are provided. The pharmaceutical formulations prepared from the compounds can be used in the treatment of cancer either as a single agent or in combination with at least one other cancer therapeutic, chemotherapeutic or anti-cancer agent.

15 Claims, 34 Drawing Sheets
Specification includes a Sequence Listing.

(56) References Cited

OTHER PUBLICATIONS

Marvel, Douglas et al., "Myeloid-Derived Suppressor Cells in the tumor Microenvironment: Expect the Unexpected", J. Clin Invest, 125(9):3356-3362 (2015).

Newmark, J. et al., "Preparation and Properties of Adducts of Streptokinase and Streptokinase-Plasmin Complex with Polyethylene Glycol and Pluronic Polyol F38", J Appl Biochem, 4:185-189 (1982).

Nguyen, D.X. et al., "Metastasis: From Dissemination to Organ-Specific Colonization", Nat Rev Cancer, 9 (4):274-284 (2009). (Abstract Only).

Ouzounova, Maria et al., "Monocytic and Granulocytic Myeloid Derived suppressor Cells Differentially Regulate Spatiotemporal Tumour Plasticity During Metastatic Cascade", Nat Comm, 8:14979 (2017).

Paget, Stephen, "Distribution of Secondary Growths in Cancer of the Breast", Cancer Metastat Rev, 8:98-101 (1989).

Remington's Pharmaceutical Sciences, 20th ed., Lippincott Williams & Wilkins, Baltimore, MD, p. 704 (2000).

Riggi, Nicolo et al., "Cancer Metastasis: A Reappraisal of Its Underlying Mechanisms and Their Relevance to Treatment", Annu Rev of Pathol: Mechanisms of Disease, 13:117-140 (2017).

Soundararajan, Rama et al., "A Novel Embryonic Plasticity Gene Signature that Predicts Metastatic Competence and Clinical Outcome", Sci Rep, 5:11766 (2015).

Tan, Tuan Zea et al., "Epithelial-Mesenchymal Transition Spectrum Quantification and its Efficacy in Deciphering Survival and Drug Responses of Cancer Patients", EMBO Mol Med, 6(10):1279-1293 (2014).

Tsai, Jeff H. et al., "Spatiotemporal Regulation of Epithelial-Mesenchymal Transition is Essential for Squamous Cell Carcinoma Metastasis", Cancer Cell, 22(6):725-736 (2012).

\* cited by examiner

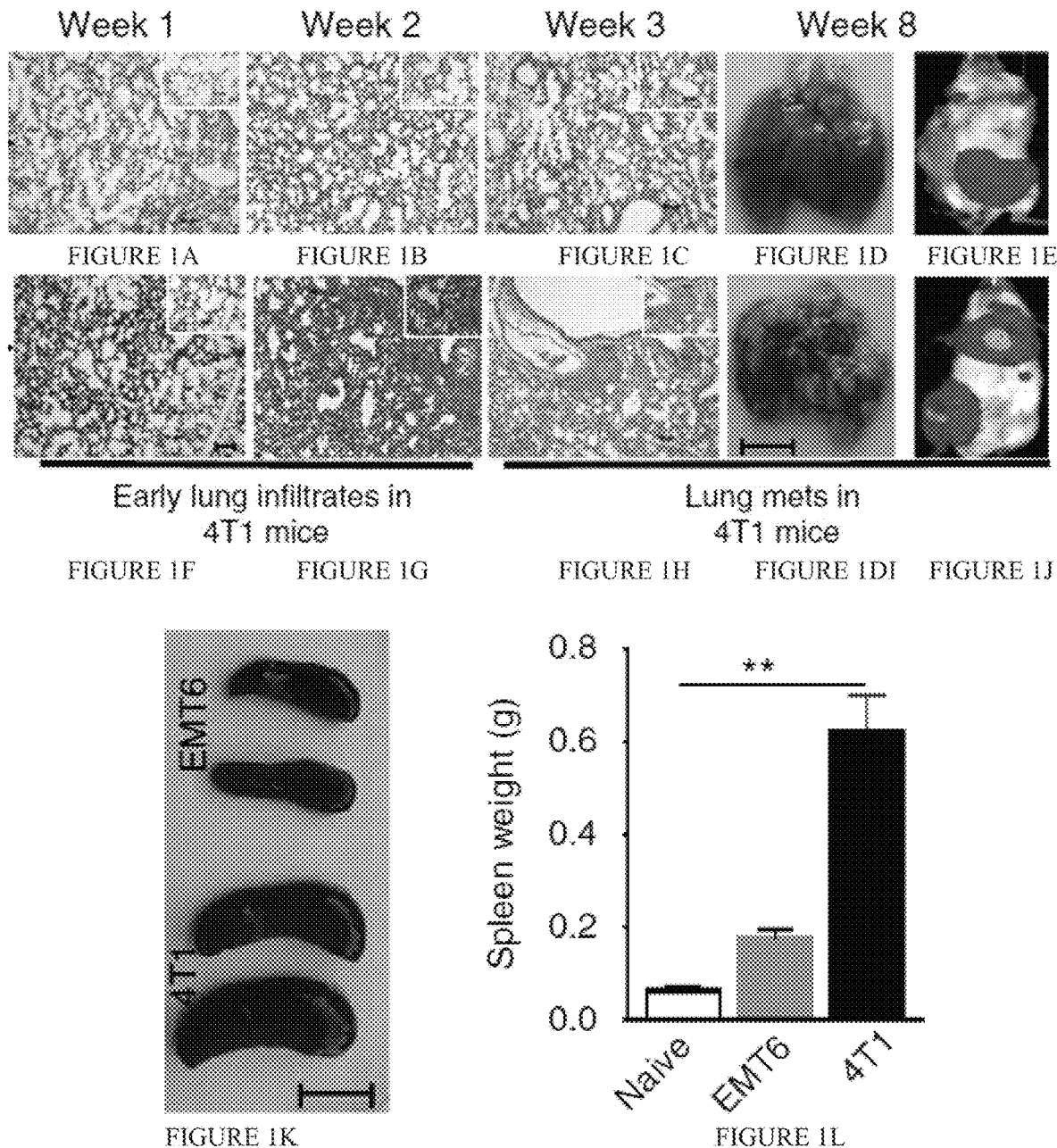

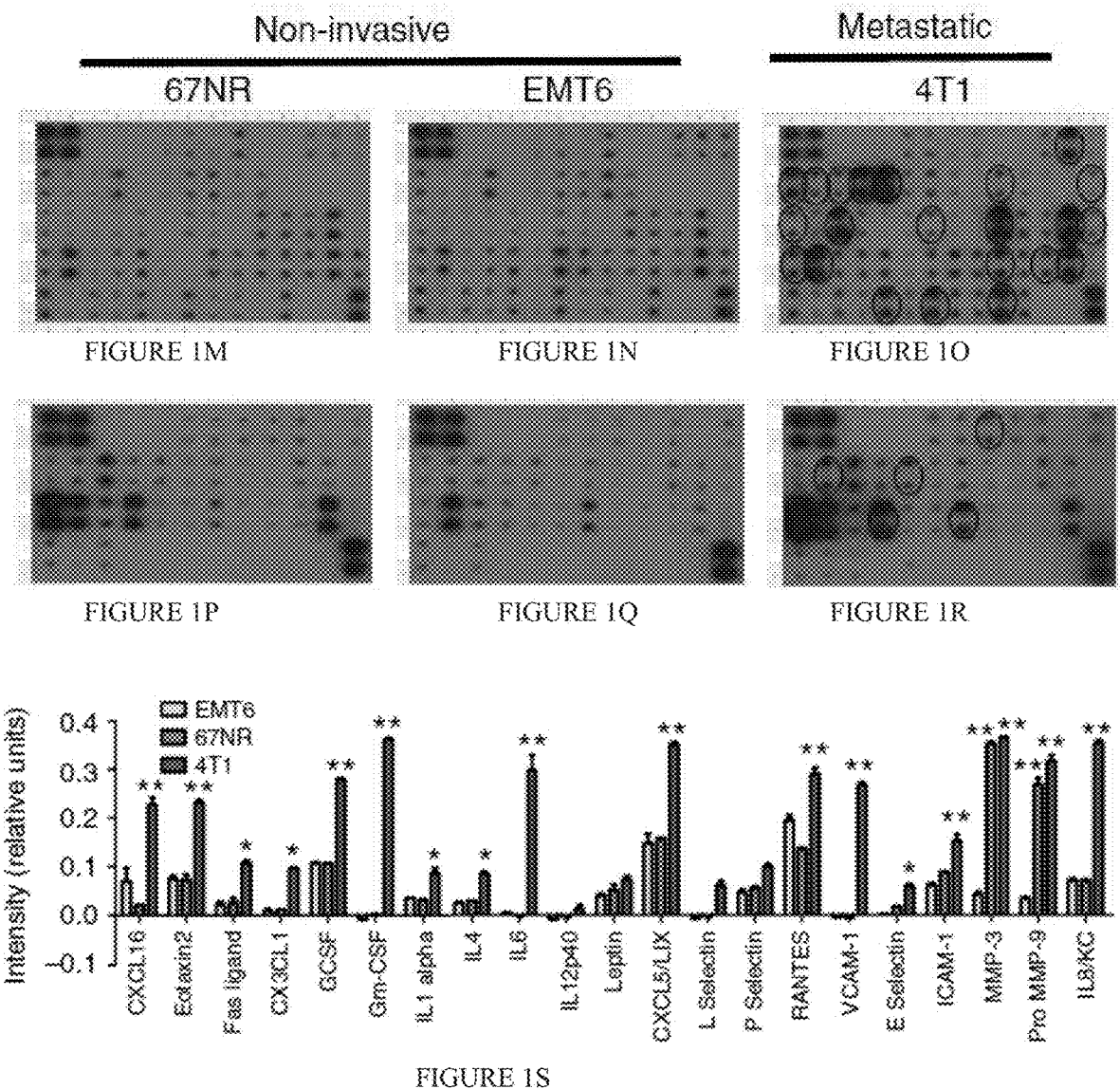

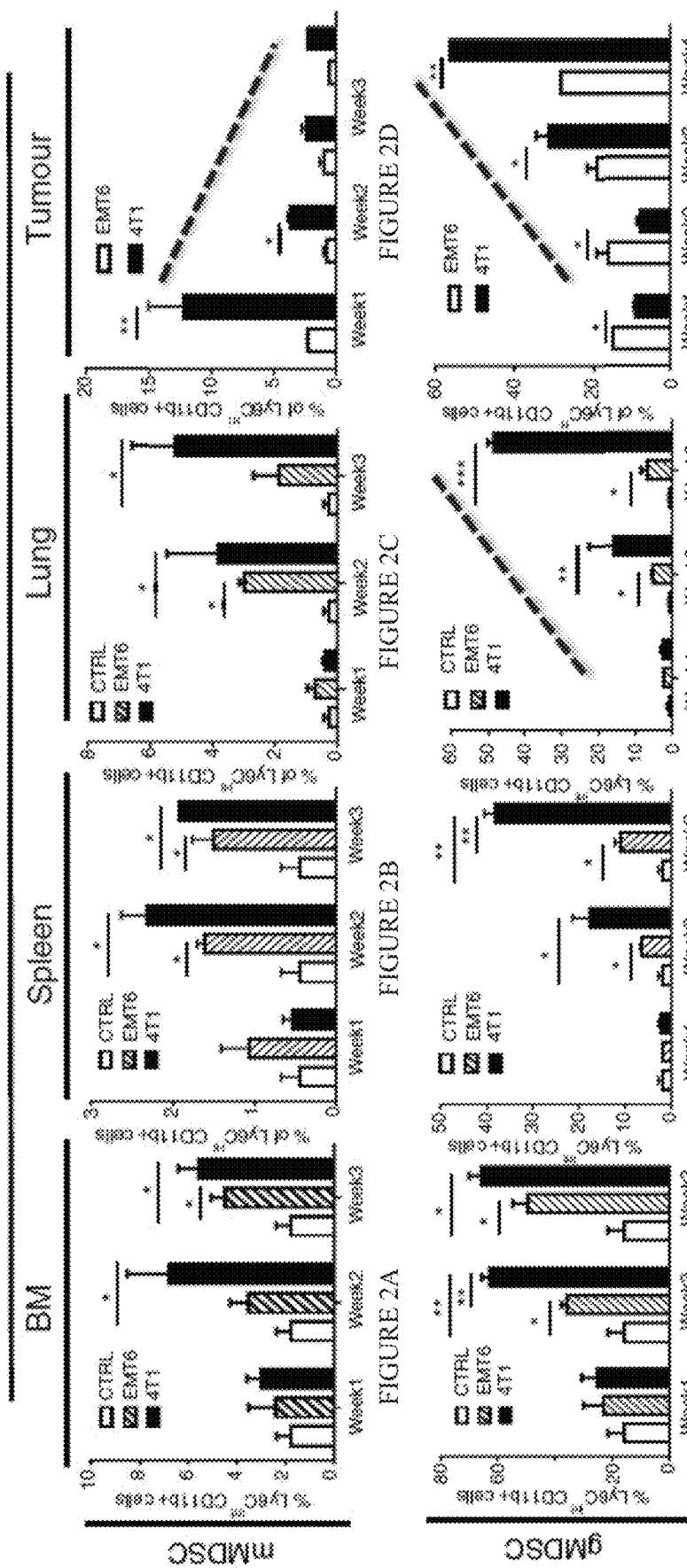

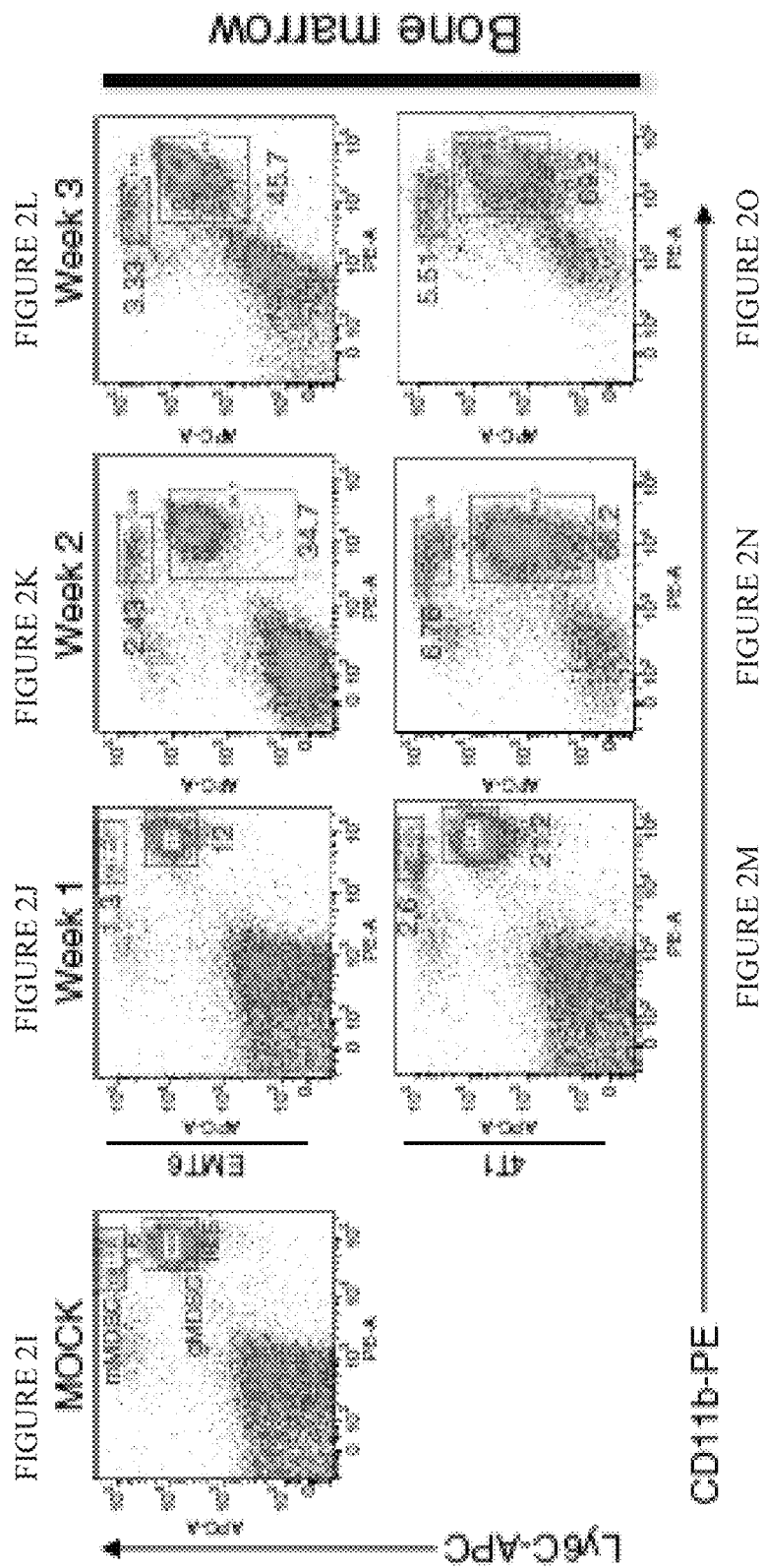

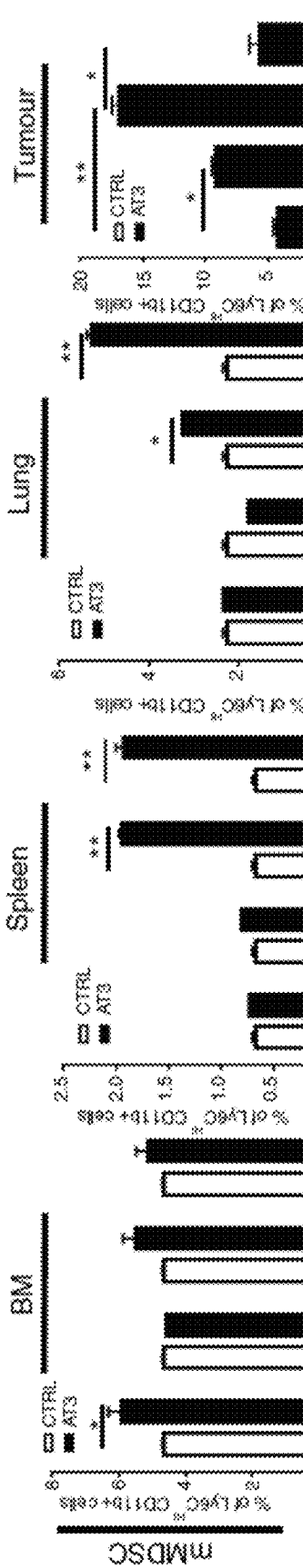

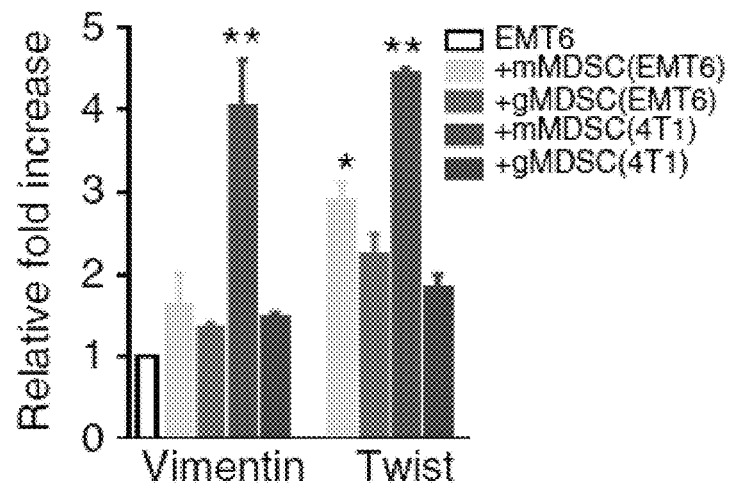
FIGURE 3W
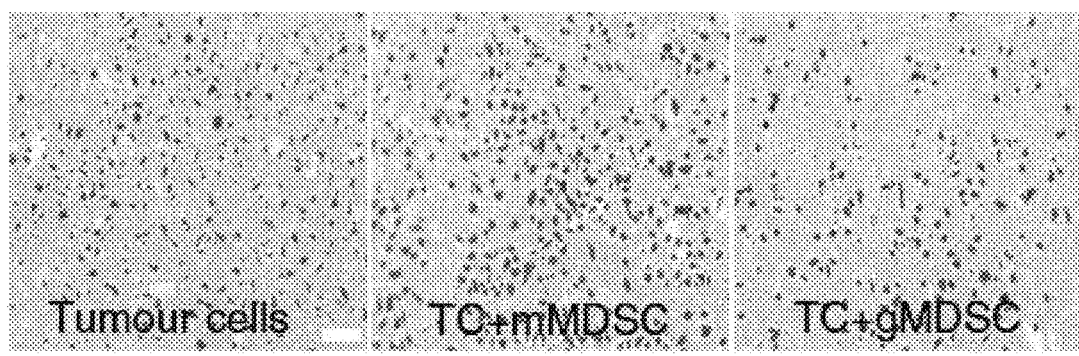
FIGURE 3X — FIGURE 3Y — FIGURE 3Z
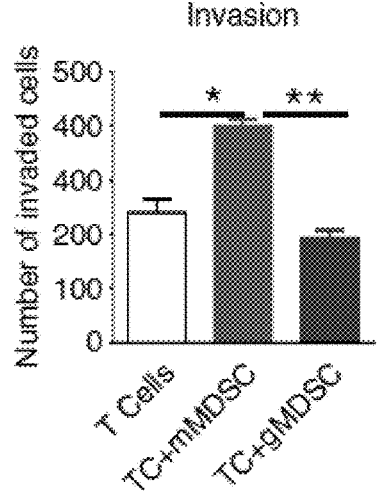 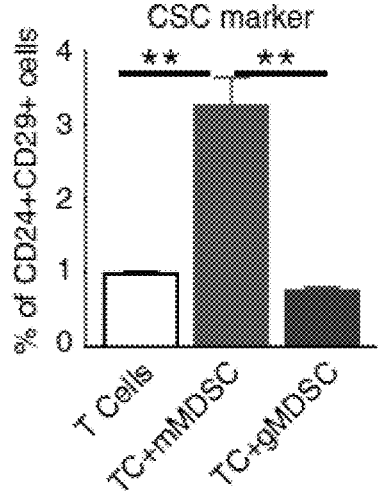 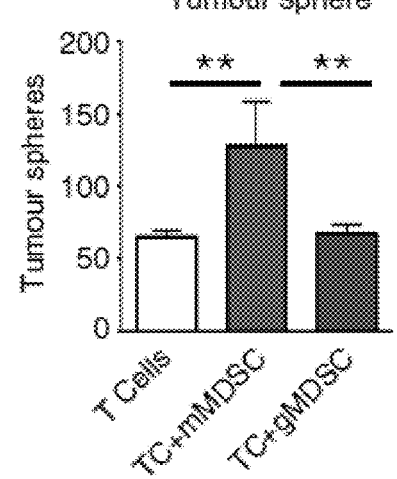
FIGURE 3AA — FIGURE 3BB — FIGURE 3CC

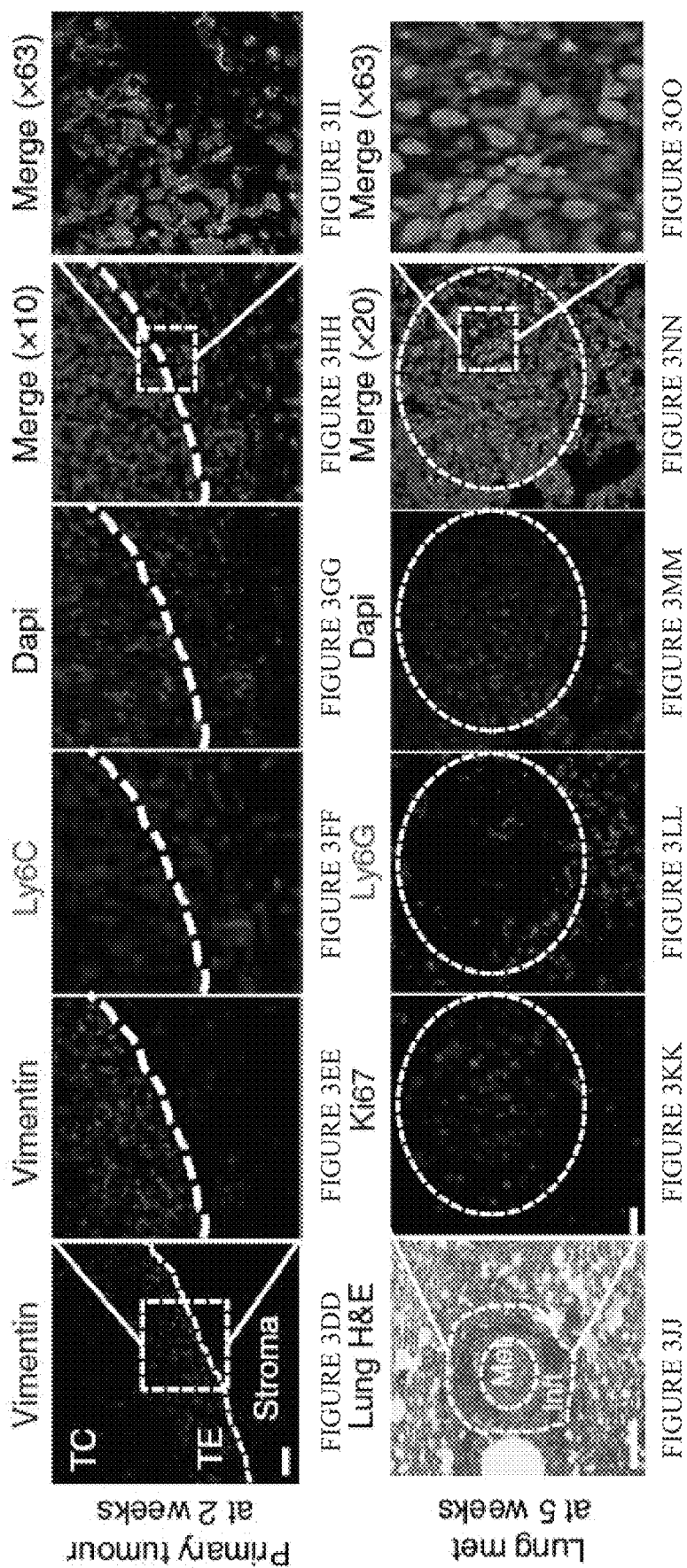

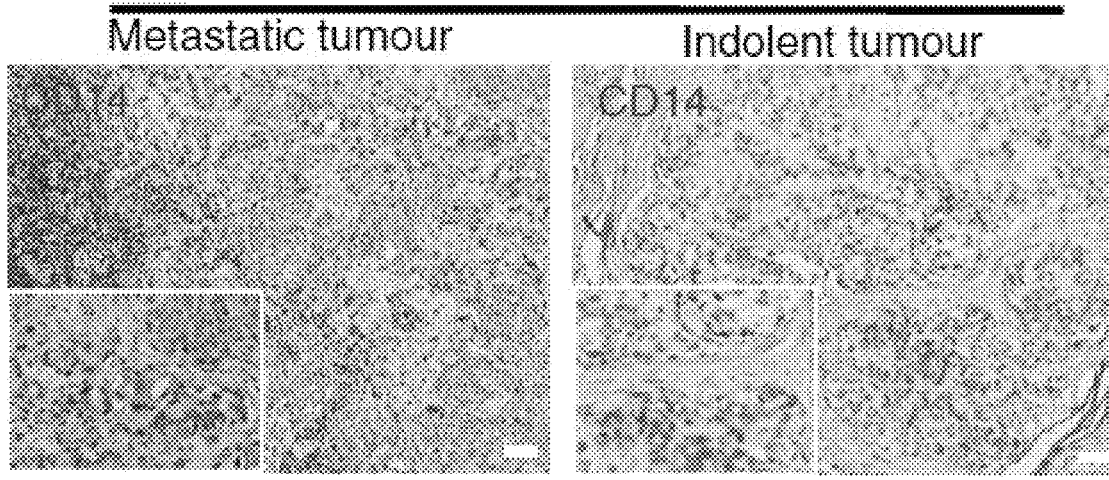
FIGURE 3PP — Human breast cancer samples, Metastatic tumour
FIGURE 3QQ — Indolent tumour
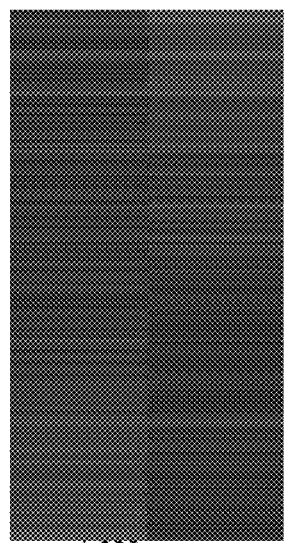
FIGURE 4A — MDSC subsets only; 1,029 genes; BM ← Source of MDScs
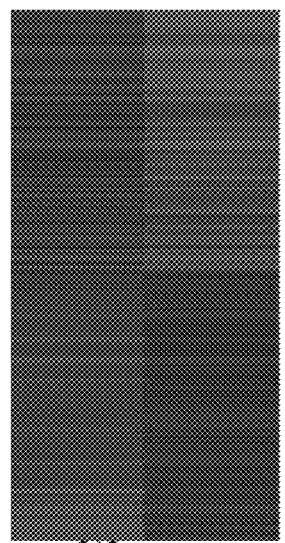
FIGURE 4B — Co-culture: Tumour +MDSC subsets; 312 genes; → BM
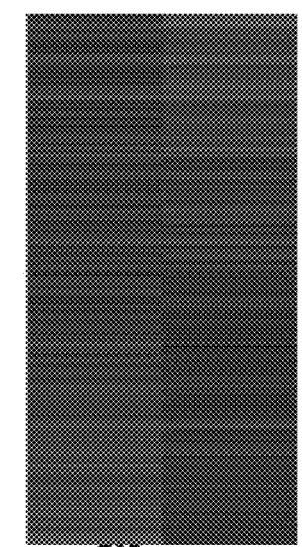
FIGURE 4C — 765 genes; Tumour

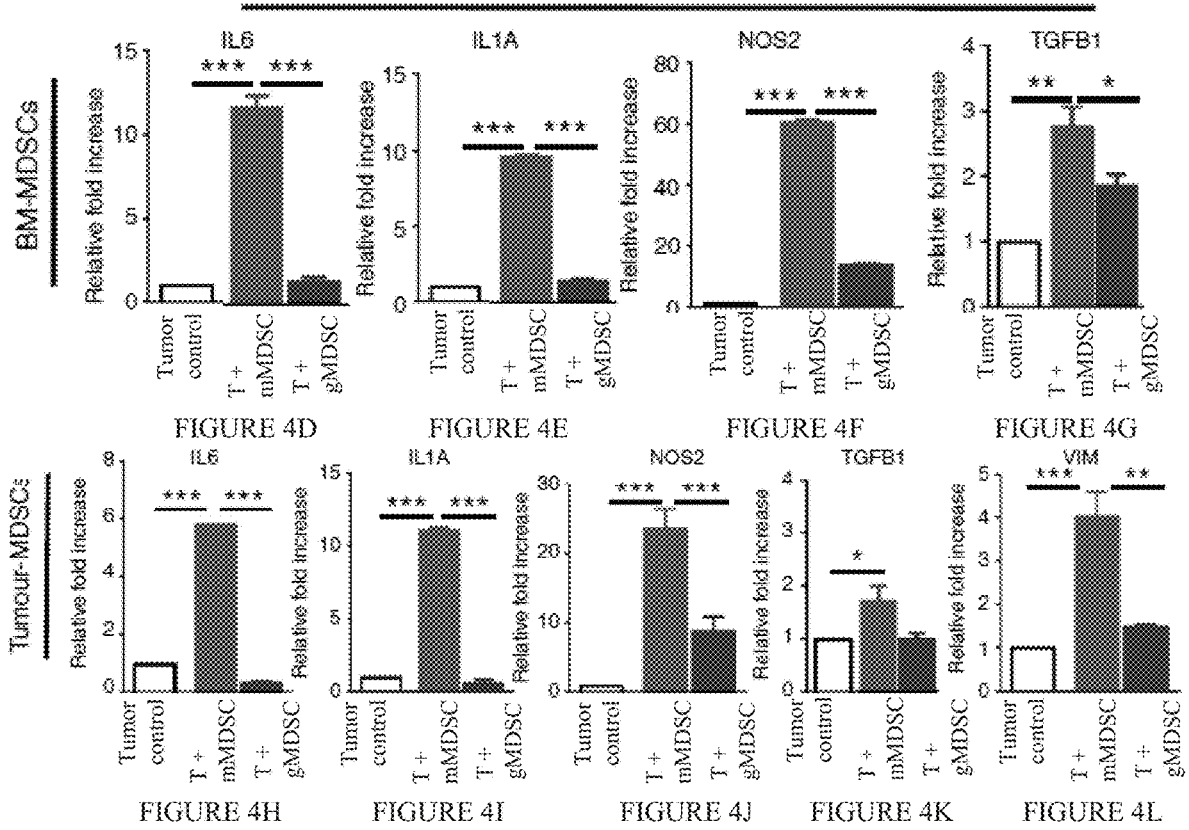
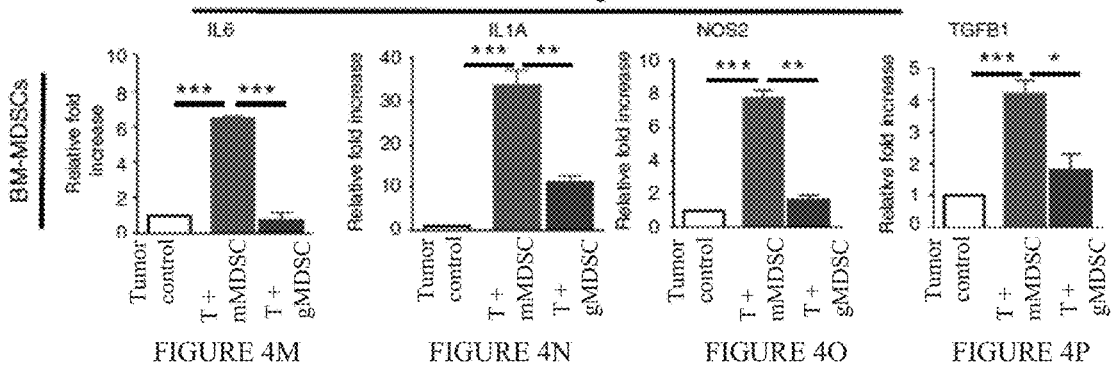

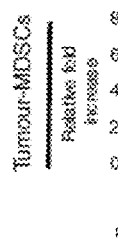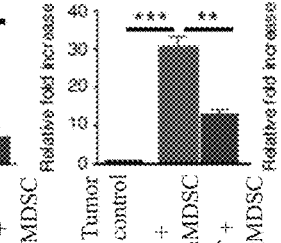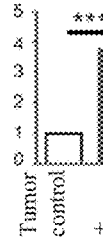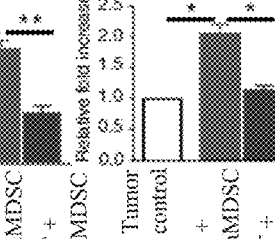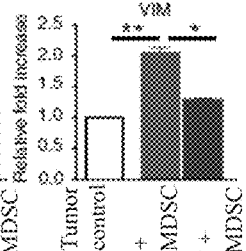
FIGURE 4Q   FIGURE 4R   FIGURE 4S   FIGURE 4T   FIGURE 4U
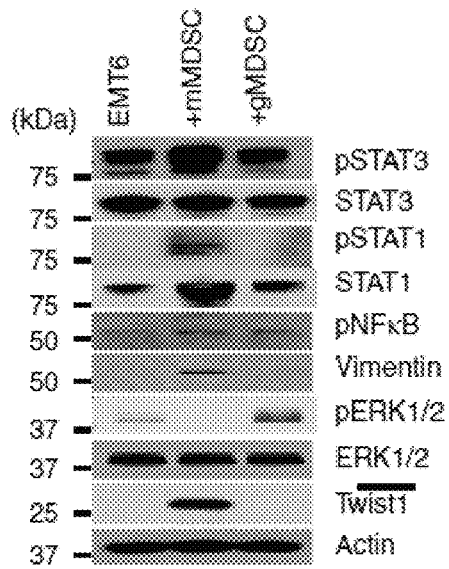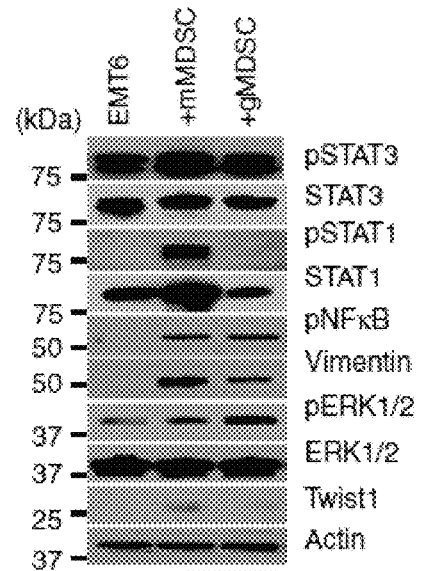
FIGURE 4V   FIGURE 4W
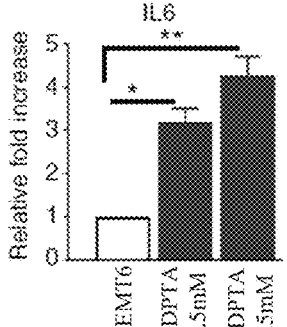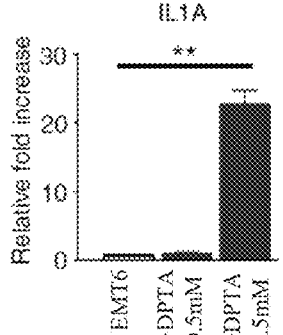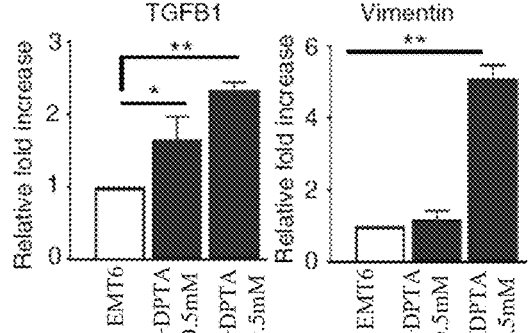
FIGURE 5A   FIGURE 5B   FIGURE 5C   FIGURE 5D

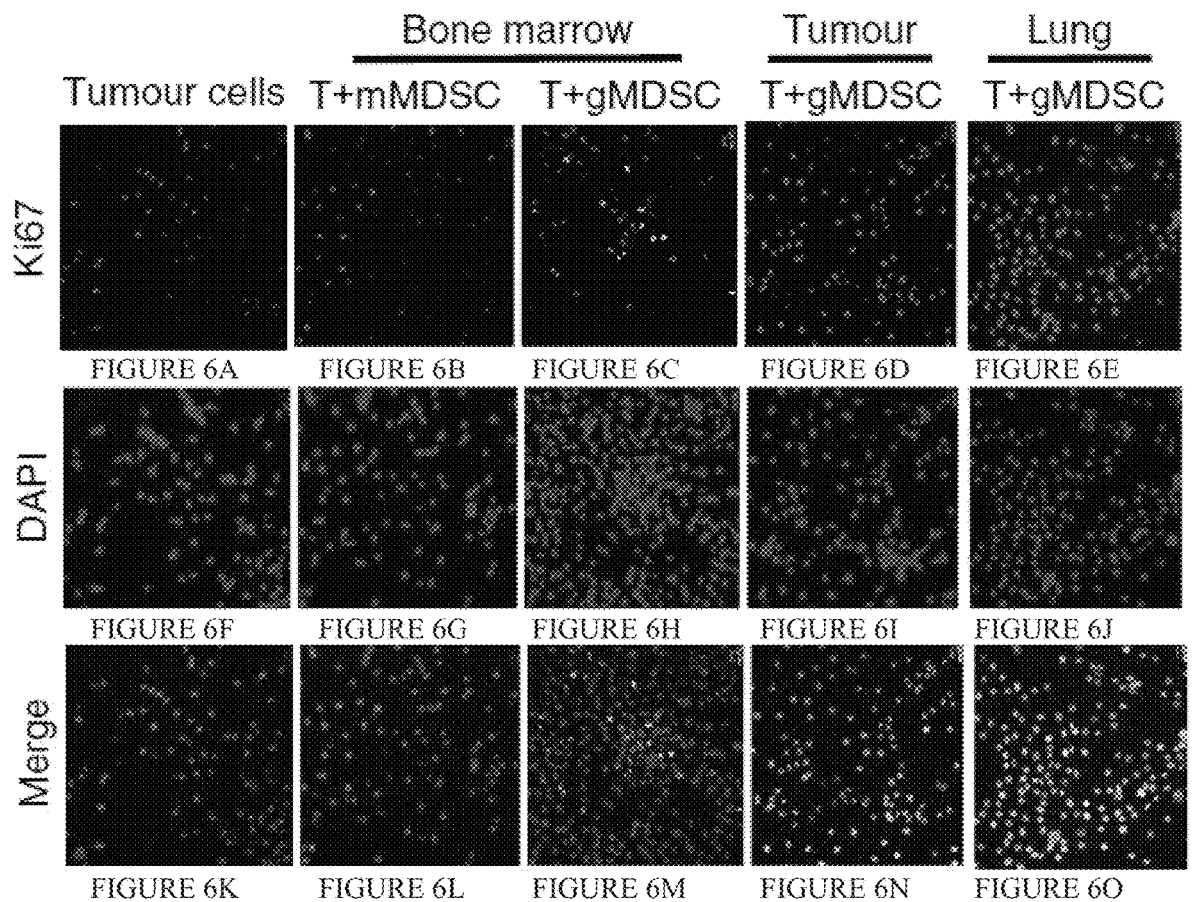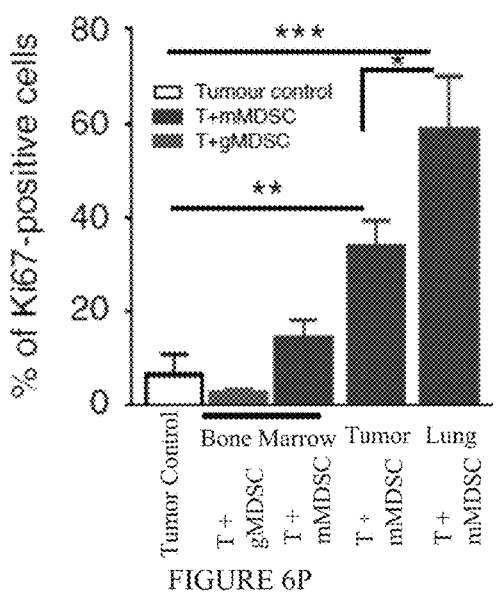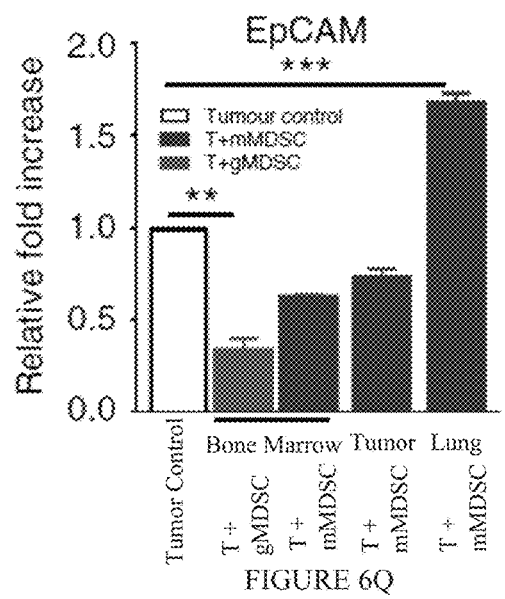

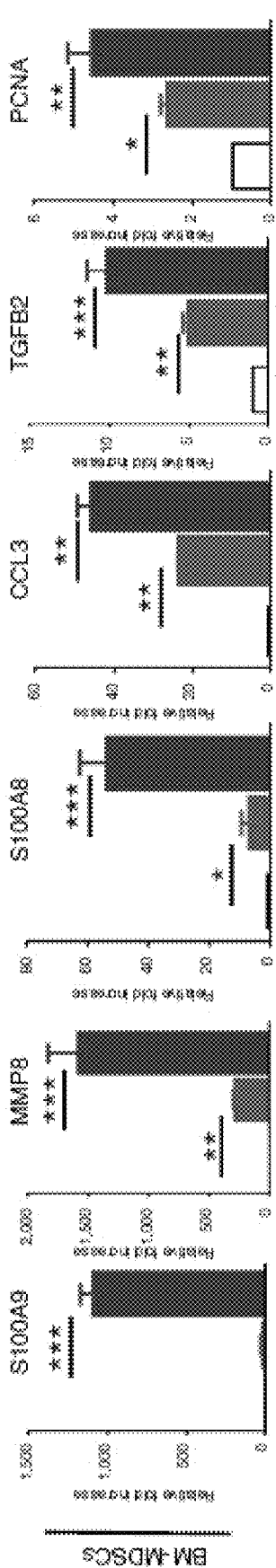

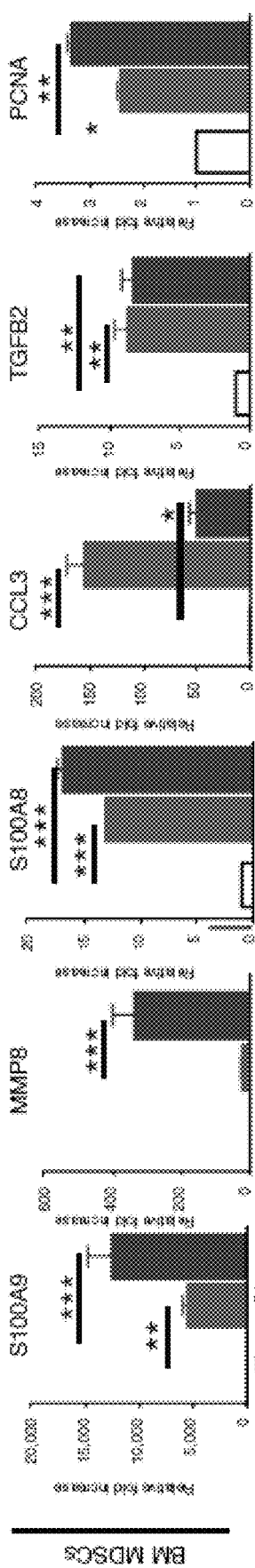
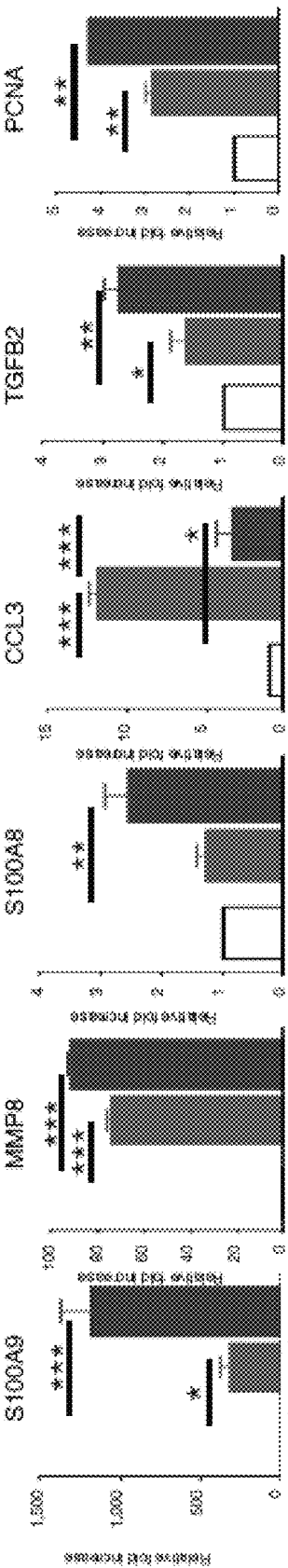
FIGURE 6FF, FIGURE 6GG, FIGURE 6HH, FIGURE 6II, FIGURE 6JJ, FIGURE 6KK, FIGURE 6LL, FIGURE 6MM, FIGURE 6NN, FIGURE 6OO, FIGURE 6PP, FIGURE 6QQ

Breast carcinoma (TCGA, Cell 2015)

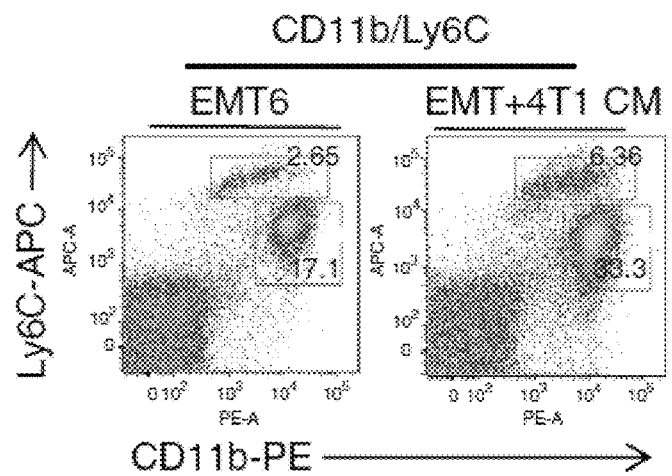
FIGURE 8D  FIGURE 8E
 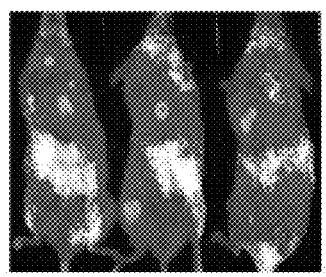
FIGURE 8F  FIGURE 8G
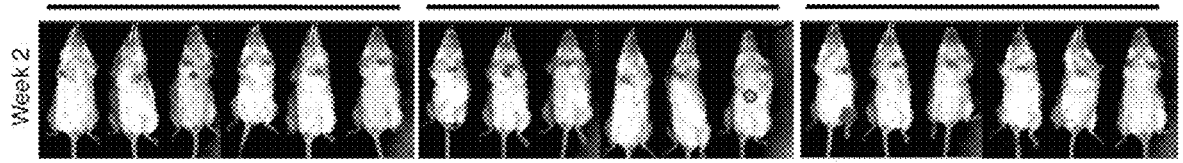
FIGURE 8H  FIGURE 8I  FIGURE 8J
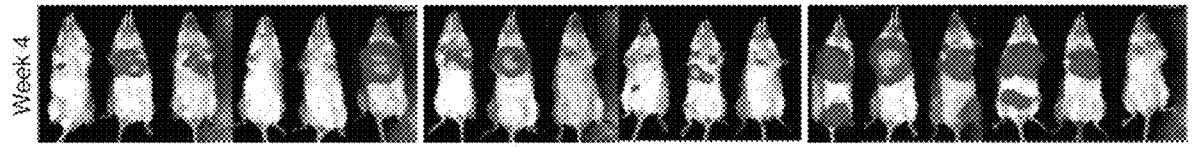
FIGURE 8K  FIGURE 8L  FIGURE 8M

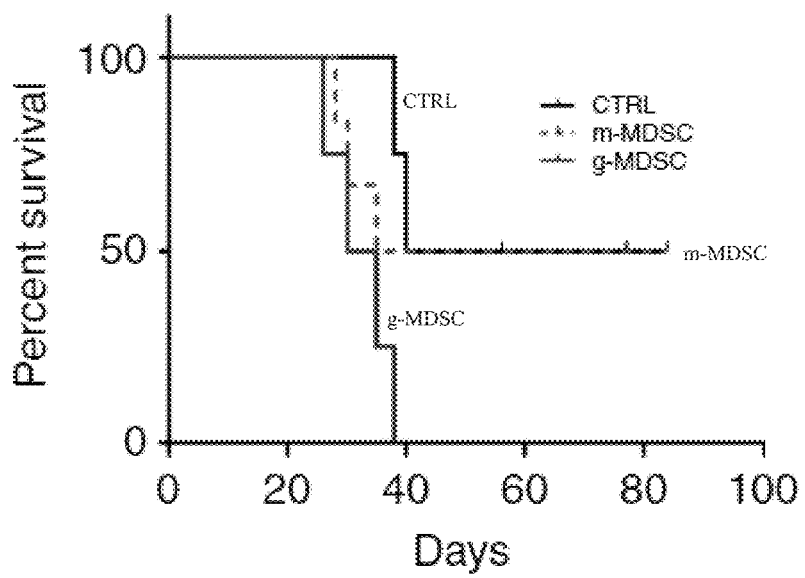
FIGURE 8N
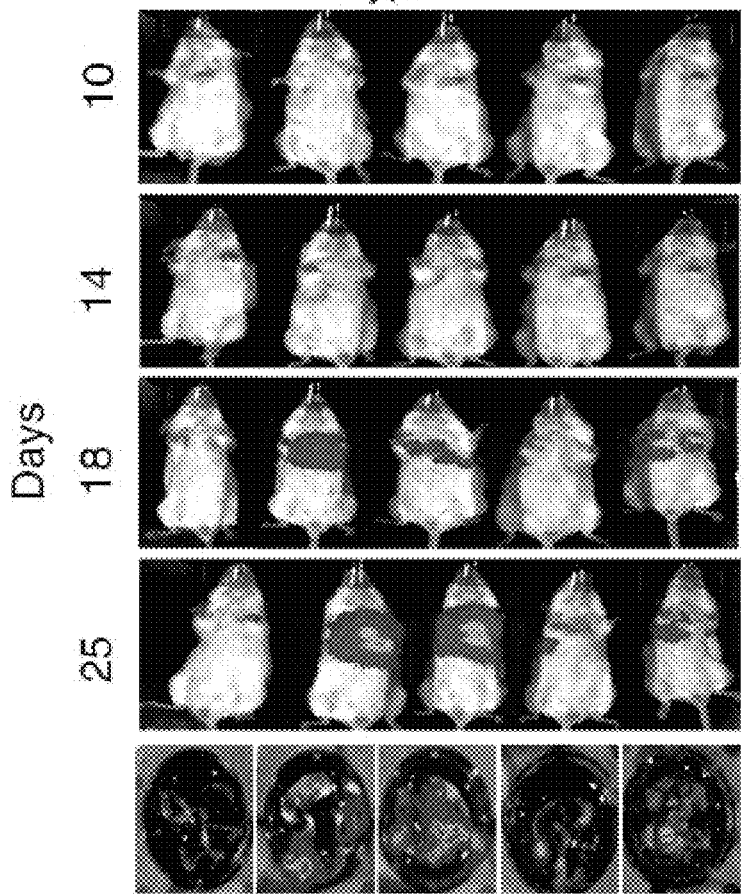
FIGURE 9A
FIGURE 9B
FIGURE 9C
FIGURE 9D
FIG. 9E  FIG. 9F  FIG. 9G  FIG. 9H  FIG. 9I Anti-Ly6gAb

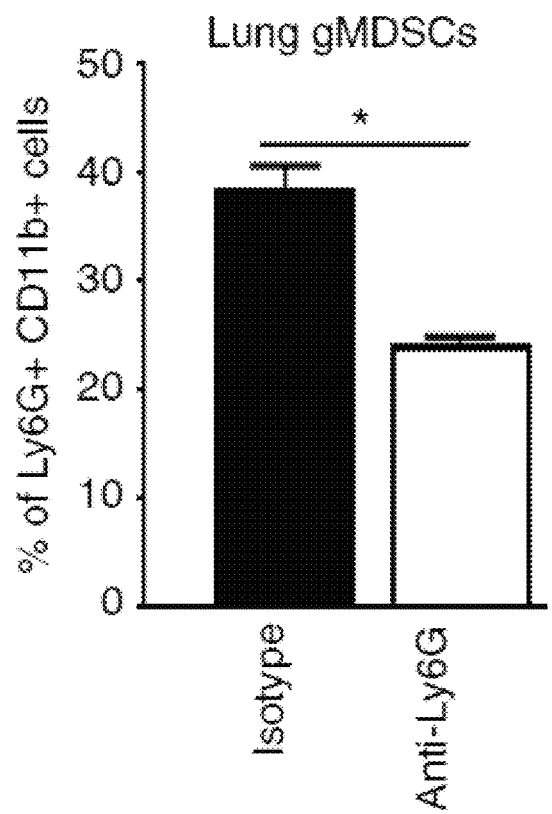
FIGURE 9T
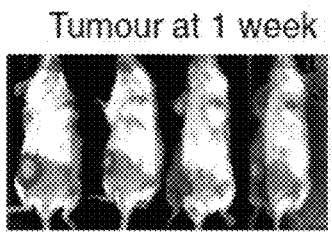
FIGURE 10A
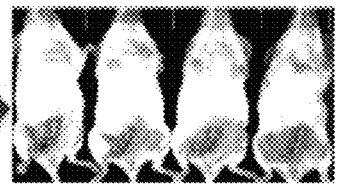
FIGURE 10B
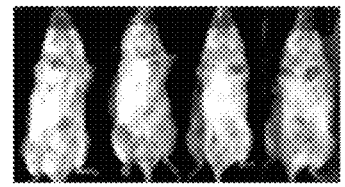
FIGURE 10C
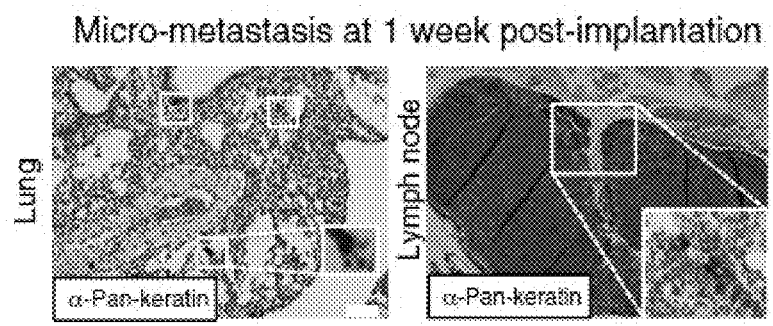
FIGURE 10D
FIGURE 10E

 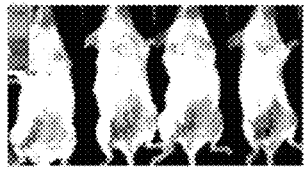 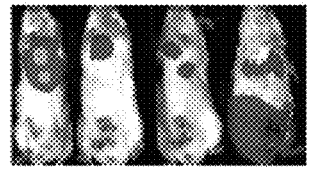
FIGURE 10F          FIGURE 10G          FIGURE 10H
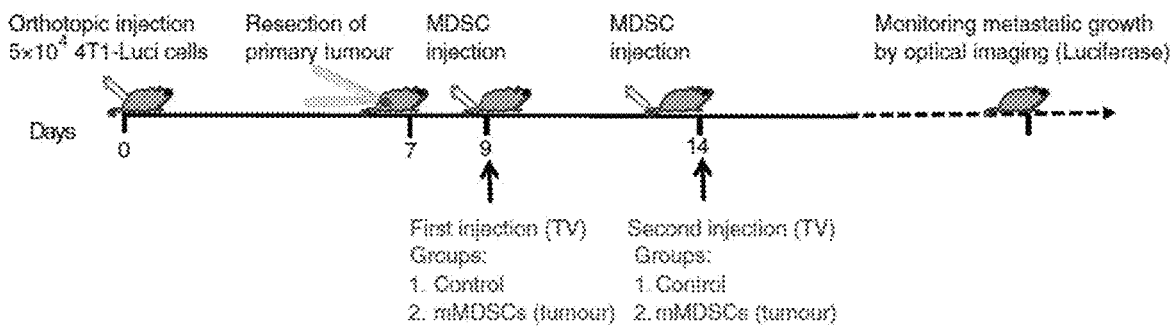
FIGURE 10I
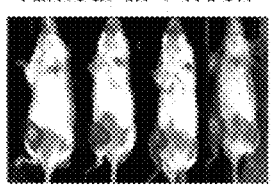 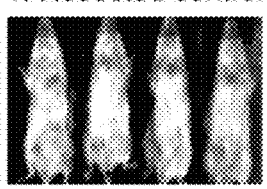 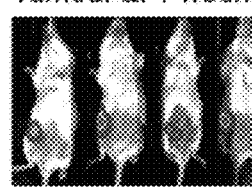 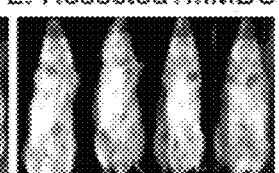
FIGURE 10J     FIGURE 10K          FIGURE 10L          FIGURE 10M
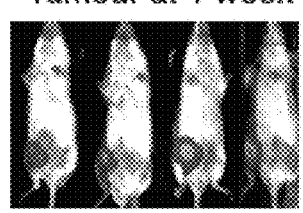 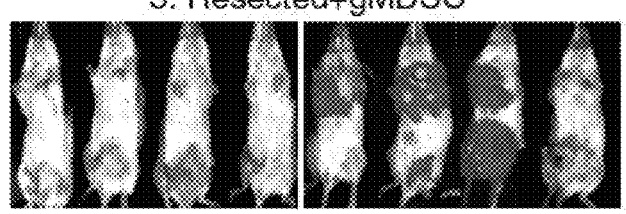
FIGURE 10N          FIGURE 10O          FIGURE 10P

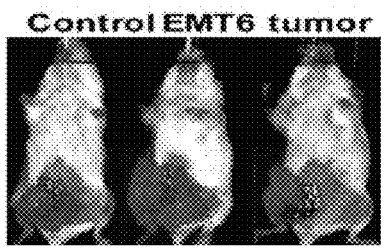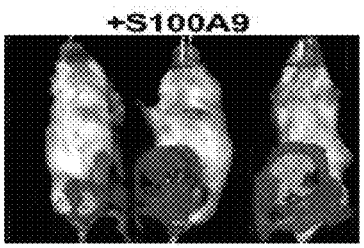
FIGURE 11B　　　　FIGURE 11C　　　　FIGURE 11D

FIGURE 11E　　　　FIGURE 11F　　　　FIGURE 11G

FIGURE 11H　　　　FIGURE 11I　　　　FIGURE 11J
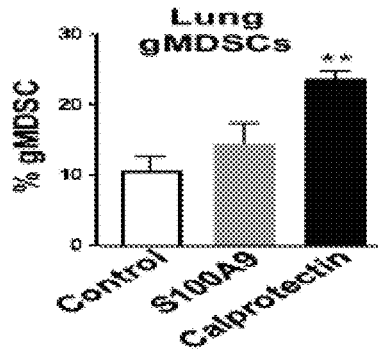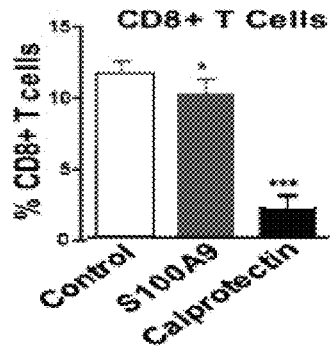
FIGURE 11K　　　　FIGURE 11L
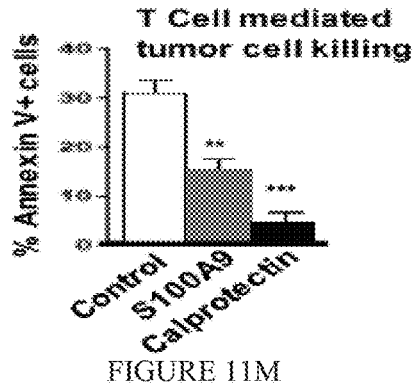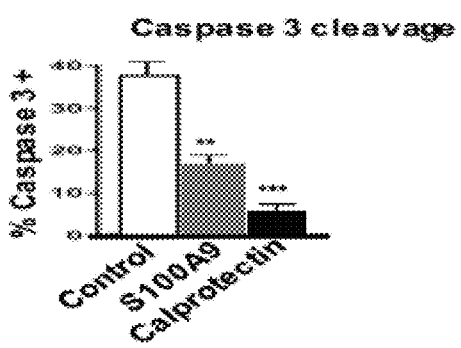
FIGURE 11M　　　　FIGURE 11N

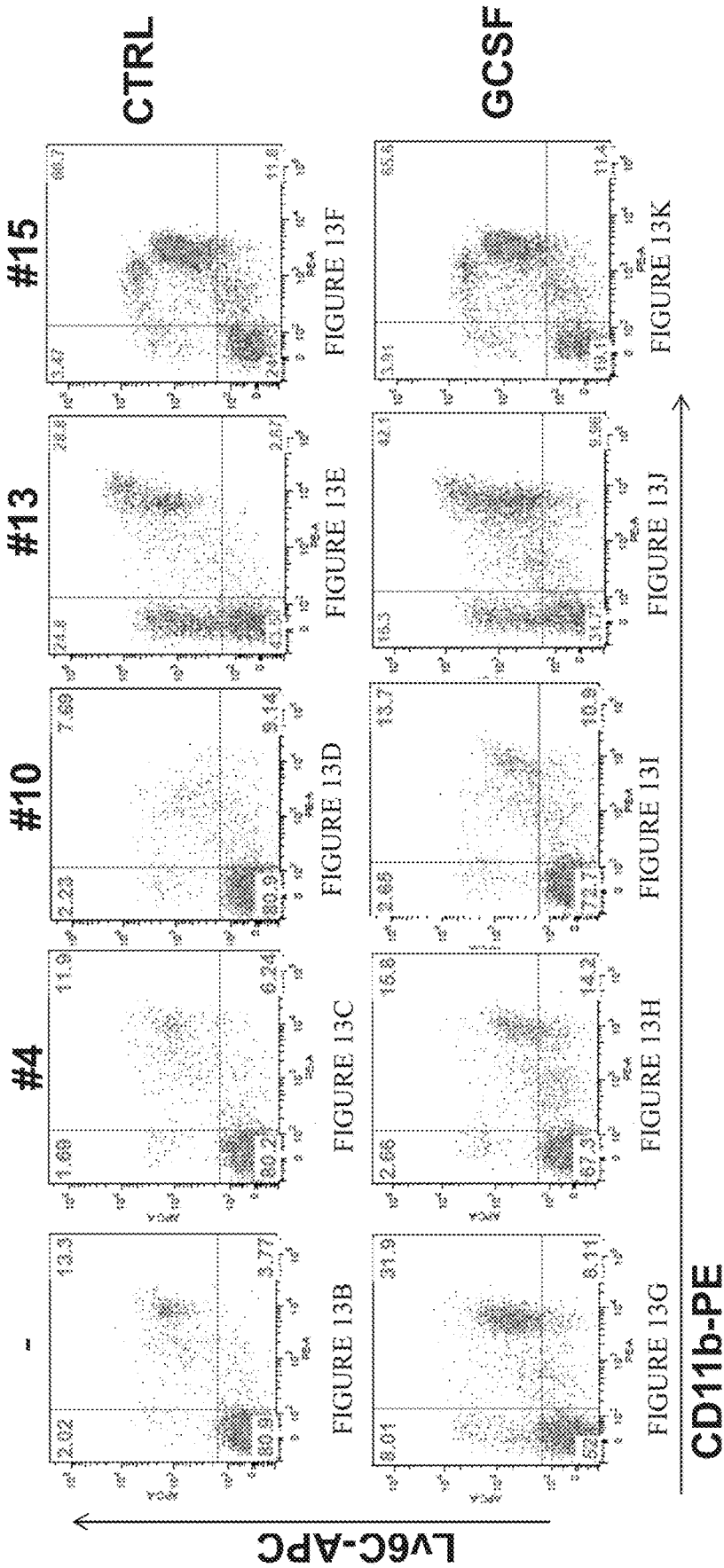

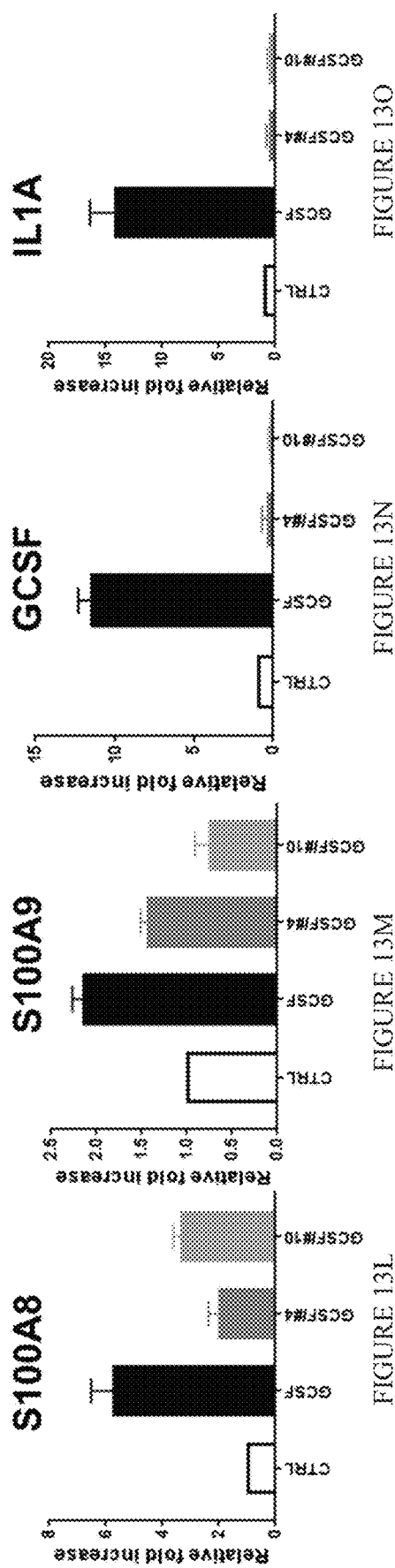

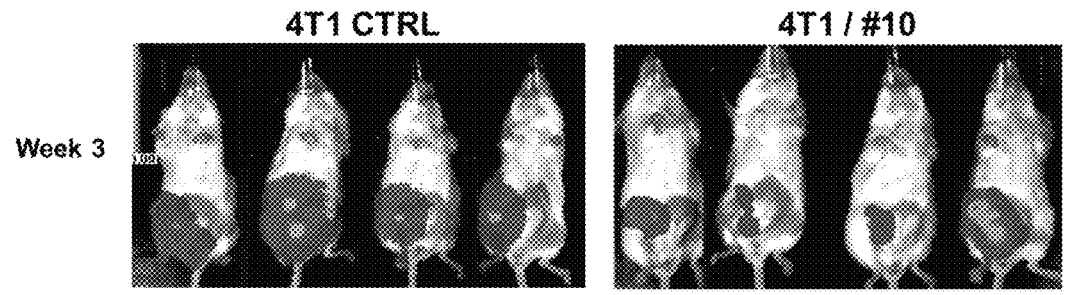
FIGURE 14A   FIGURE 14B
FIGURE 14C   FIGURE 14D
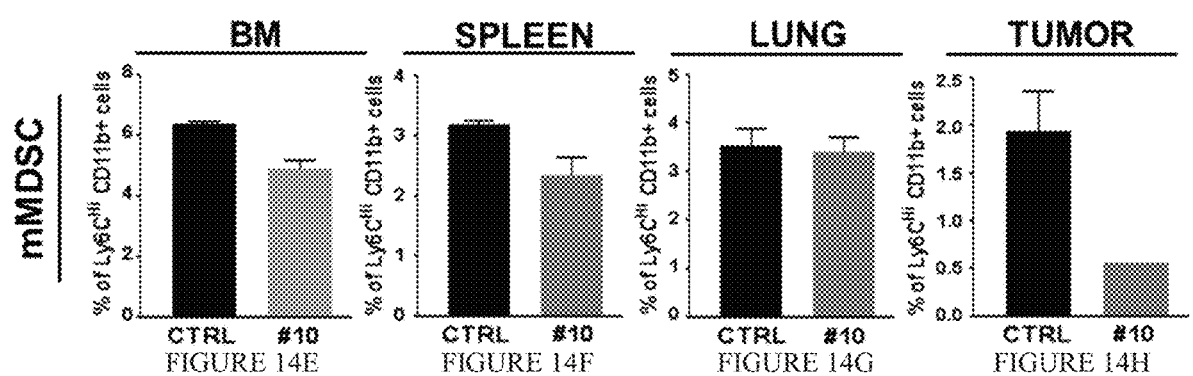
FIGURE 14E   FIGURE 14F   FIGURE 14G   FIGURE 14H
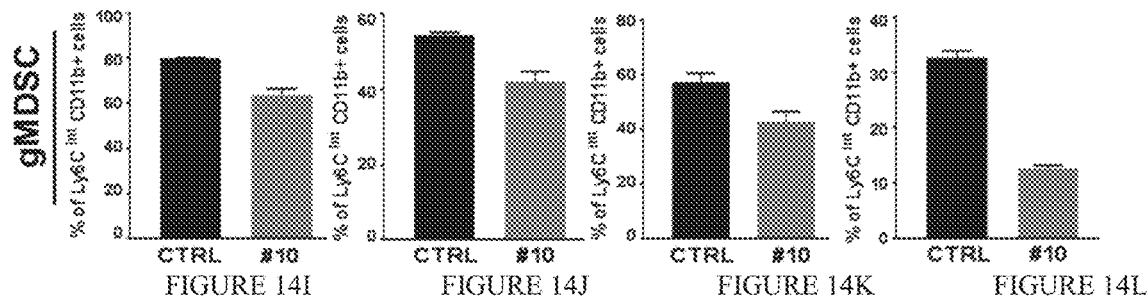
FIGURE 14I   FIGURE 14J   FIGURE 14K   FIGURE 14L

```
                            SEQUENCE LISTING

<160> NUMBER OF SEQ ID NOS: 27

<210> SEQ ID NO 1
<211> LENGTH: 24
<212> TYPE: DNA
<213> ORGANISM: Artificial Sequence
<220> FEATURE:
<223> OTHER INFORMATION: Synthetic

<400> SEQUENCE: 1
gcctgcagga tgagattcag aata                                          24

<210> SEQ ID NO 2
<211> LENGTH: 25
<212> TYPE: DNA
<213> ORGANISM: Artificial Sequence
<220> FEATURE:
<223> OTHER INFORMATION: Synthetic

<400> SEQUENCE: 2
aaccagaggg agtgaatcca gatta                                         25

<210> SEQ ID NO 3
<211> LENGTH: 18
<212> TYPE: DNA
<213> ORGANISM: Artificial Sequence
<220> FEATURE:
<223> OTHER INFORMATION: Synthetic

<400> SEQUENCE: 3
cgggtcatgg ctaacgtg                                                 18

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
cagcttgcca tcttggagtc                                               20

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
aagaaatgat ggatgctacc                                               20

<210> SEQ ID NO 6
<211> LENGTH: 22
<212> TYPE: DNA
<213> ORGANISM: Artificial Sequence
<220> FEATURE:
<223> OTHER INFORMATION: Synthetic

<400> SEQUENCE: 6
gagtttctgt atctctctga ag                                            22

<210> SEQ ID NO 7
```

```
<211> LENGTH: 20
<212> TYPE: DNA
<213> ORGANISM: Artificial Sequence
<220> FEATURE:
<223> OTHER INFORMATION: Synthetic

<400> SEQUENCE: 7
cataacccat gatctggaag                                                    20

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
attcatgaca aacttctgcc                                                    20

<210> SEQ ID NO 9
<211> LENGTH: 21
<212> TYPE: DNA
<213> ORGANISM: Artificial Sequence
<220> FEATURE:
<223> OTHER INFORMATION: Synthetic

<400> SEQUENCE: 9
catcaaccag tattatggct c                                                  21

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
tttcctttgt tacagcttcc                                                    20

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
ccctatattt ggagcctgga                                                    20

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
cttgcgaccc acgtagtaga                                                    20

<210> SEQ ID NO 13
<211> LENGTH: 21
<212> TYPE: DNA
<213> ORGANISM: Artificial Sequence
<220> FEATURE:
<223> OTHER INFORMATION: Synthetic

<400> SEQUENCE: 13
```

```
gagatttgca ggtattgatg g                                              21

<210> SEQ ID NO 14
<211> LENGTH: 21
<212> TYPE: DNA
<213> ORGANISM: Artificial Sequence
<220> FEATURE:
<223> OTHER INFORMATION: Synthetic

<400> SEQUENCE: 14
caacaacatt agcaggagat g                                              21

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
atacaaggaa atcaccatgc                                                20

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
ctttagcctt gagcaagaag                                                20

<210> SEQ ID NO 17
<211> LENGTH: 21
<212> TYPE: DNA
<213> ORGANISM: Artificial Sequence
<220> FEATURE:
<223> OTHER INFORMATION: Synthetic

<400> SEQUENCE: 17
tccttcctag agtattgatg g                                              21

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
aactatggat tcccaaggag                                                20

<210> SEQ ID NO 19
<211> LENGTH: 22
<212> TYPE: DNA
<213> ORGANISM: Artificial Sequence
<220> FEATURE:
<223> OTHER INFORMATION: Synthetic

<400> SEQUENCE: 19
ctttgattgt catatctcca gc                                             22

<210> SEQ ID NO 20
<211> LENGTH: 21
<212> TYPE: DNA
```

```
<213> ORGANISM: Artificial Sequence
<220> FEATURE:
<223> OTHER INFORMATION: Synthetic

<400> SEQUENCE: 20
cggaagattc cacgccaatt c                                              21

<210> SEQ ID NO 21
<211> LENGTH: 21
<212> TYPE: DNA
<213> ORGANISM: Artificial Sequence
<220> FEATURE:
<223> OTHER INFORMATION: Synthetic

<400> SEQUENCE: 21
ggtgaggaac gtgtcctgaa g                                              21

<210> SEQ ID NO 22
<211> LENGTH: 21
<212> TYPE: DNA
<213> ORGANISM: Artificial Sequence
<220> FEATURE:
<223> OTHER INFORMATION: Synthetic

<400> SEQUENCE: 22
ctgaggtacc tgaactttt c                                               21

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
tatactctac aacaaggggc                                                20

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
aaggtcatcc cagagctgaa                                                20

<210> SEQ ID NO 25
<211> LENGTH: 20
<212> TYPE: DNA
<213> ORGANISM: Artificial Sequence
<220> FEATURE:
<223> OTHER INFORMATION: Synthetic

<400> SEQUENCE: 25
ctgcttcacc accttcttga                                                20

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
gatgtatgaa ggctttggtc                                                20
```

```
<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27 tgtgcactttt tattggtctc                                              20
```

COMPOSITIONS AND METHODS FOR INHIBITING METASTASIS

CROSS-REFERENCE TO RELATED APPLICATIONS

This application claims benefit of and priority to U.S. Provisional Patent Application No. 62/649,301 filed on Mar. 28, 2018, which is incorporated by reference in its entirety.

REFERENCE TO A SEQUENCE LISTING

The Sequence Listing submitted on Mar. 27, 2019, as a text file named "064466_090_ST25.txt" created on Mar. 26, 2019, and having a size of 5,203 bytes is hereby incorporated by reference pursuant to 37 C.F.R. § 1.52(e)(5).

TECHNICAL FIELD OF THE INVENTION

The invention is generally directed to methods of treating cancer, and more particularly to the use of molecules that bind to protein calprotectin.

BACKGROUND OF THE INVENTION

According to the American Cancer Society survey, about 1.7 million Americans will be diagnosed with cancer and about 609,640 Americans are expected to die of cancer this year alone (American Cancer Society, Cancer Facts & Figures (2018)). Cancer metastasis is responsible for a vast majority of cancer-related deaths (Nicolo, R., et al., Annu Rev of Pathol: Mechanisms of disease, 13: 117-140 (2017)). Metastasis is the development of secondary malignant growths in a site in the body distant from the primary site of the cancer.

Metastatic disease is the end stage of extremely inefficient processes that entails overcoming multiple physiological barriers. Evidence from preclinical and clinical settings suggests that dissemination of malignant cells is an early process in cancer progression (Husemann, Y., et al., Cancer Cell, 13:58-68 (2008)). However, the majority of disseminated cells are either eliminated in circulation or remain dormant in distant organs including the bone marrow, while very few cells eventually develop successful metastasis (Husemann, Y., et al., Cancer Cell, 13:58-68 (2008); Nguyen, D., et al., Nat Rev Cancer, 9:274-284 (2009); Klein, C. A., Nat Rev Cancer, 9:302-312 (2009)). Therefore, the mechanism by which disseminated cells go on to establish successful metastasis is of utmost importance. S. Paget's 'seed and soil' hypothesis (Paget, S., Cancer Metastat Rev, 8:98-101 (1989)) for metastasis was a key milestone in cancer research that determined the direction of subsequent studies. Isaiah J. Fidler and others provided an unequivocal confirmation of the concept suggesting that some organs were more conducive than others for disseminated tumor cells 'seed' to grow (Nguyen, D., et al., Nat Rev Cancer, 9:274-284 (2009); Fidler, I. J. and Kripke, M. L., Cancer Res, 38:2651-2660 (1978); Fidler, I. J. and Kripke, M. L., Science, 197:893-895 (1977)). Advanced studies in recent decades reframed the 'seed and soil' concept in a modern context by which successful metastases require that developing malignant cells eliminate anti-tumor responses, a small subset of (disseminating) cells—'seed'—undergo epithelial-mesenchymal transition (EMT) leading to cancer stem cell (CSC) phenotype and remotely generate a supportive microenvironment—'soil'— in distant tissues (Soundararaj an, R., et al., Sci Rep, 5:11766 (2015); Grunert, S., et al., Nat Rev Mol Cell Biol, 4:657-665 (2003)). It is also accepted that successful colonization in distant organs requires disseminated tumors to revert back to epithelial phenotype via mesenchymal-epithelial transition (MET) to promote tumor cell proliferation (Tsai, et al., Cancer Cell, 22:725-736 (2012)). Furthermore, a dynamic and reversible transition between EMT and MET state has been shown to be a critical process in driving squamous cell carcinoma metastasis (Tsai, et al., Cancer Cell, 22:725-736 (2012)). Consistent with this notion, EMT signature alone fails to predict metastasis in majority of malignancies (Soundararajan, R., et al., Sci Rep, 5:11766 (2015); Tan, et al., EMBO Mol Med, 6:1279-1293 (2014); Chikaishi, Y., et al., Anticancer Res, 31:4451-4456 (2011)).

Emerging evidence suggests that tumor-infiltrated immune cells (mainly from myeloid origin) differentiate into cells that promote tumor growth and invasion in addition to their immunosuppressive role (Marvel, D. and Gabrilovich, D. I., J Clin Invest, 125:3356-3362 (2015); Condamine, T., et al., Annu Rev Med, 66:97-110 (2015)). Although myeloid-derived suppressor cells (MDSC) were initially identified in cancer patients and mouse models due to their potent immunesuppressive activity, they are now being implicated in the promotion of tumor metastasis by participating in the formation of pre-metastatic niches, angiogenesis and invasion (Condamine, T., et al., Annu Rev Med, 66:97-110 (2015)). MDSCs are a heterogeneous population of immature myeloid cells that include monocytic (mMDSC) and granulocytic (gMDSC) subsets both of which have been shown to be immunesuppressive. However, the majority of current studies do not separate the two groups of MDSCs.

The majority of well-known chemotherapies are hindered by induction of MDSCs, and T-cell suppression (Ding, Z., et al., Oncoimmunology, 8: e954471, (2014), Gargett, T., et al., Clin Transl Immunology, 5(12): e119 (2016)). There is a great need for drugs that can assist in boosting T-cell production, prevent cancer metastasis, and prepare the host body to accommodate adjuvant cancer therapeutics.

Therefore, it is an object of the invention to provide compositions and methods for inhibiting metastasis.

It is another object of the invention to provide compositions and methods for treating metastatic cancer.

SUMMARY OF THE INVENTION

Compositions and methods are provided that inhibit or reduce cancer metastasis. In one embodiment, the compositions are calprotectin inhibitors. In another embodiment, the metastatic inhibition occurs through the inhibition of granulocytic myeloid derived suppressor cells.

One embodiment provides a compound according Formula I:

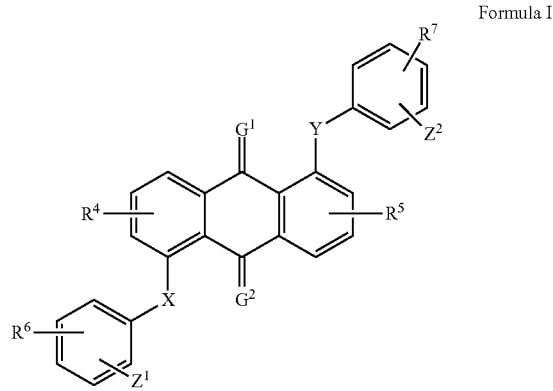

Formula I wherein:

G¹ and G² are each independently —O, —S, —NH, —NR¹, —CH₂, —CHR¹, —CR¹R²,

X and Y are each independently —O, —NH, —NR¹, or —S, wherein each occurrence of R¹ is selected from straight chain or branched non-cyclic lower alkyl group, R⁴, R⁵, R⁶, and R⁷ are separately selected from a group consisting of —H, —F, —Cl, —Br, —I, alkoxy group, —CF₃, —OCF₃, —CN, —CONHR², —CONR²R³, —SO₂CH³, —SO₂NHR³, Z¹ and Z² may separately be an —H, —F, —Cl, —Br, —I, —N—(C1-C12)-alkyl, N-aryl, —N-aralkyl, benzyl, benzyloxy, alkoxy, aryl, aralkyloxy, —SH, —S—(C1-C12)-alkyl, —S-aryl, —SO₂, CF₃, —OCF₃, —CN, —CONHR¹, —CONR¹R², —SO₂CH₃, or —SO₂NHR¹, or a pharmaceutically acceptable salt, hydrate, solvate, or derivative thereof.

Another embodiment provides a compound according to Formula II:

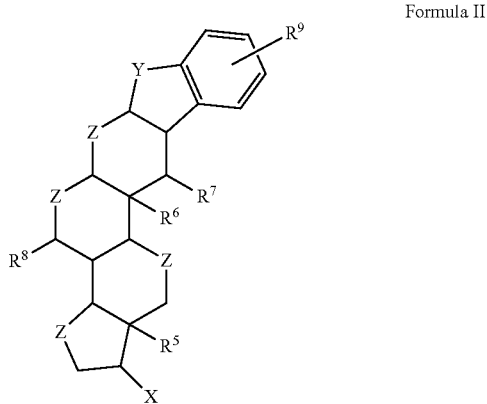

Formula II wherein:

X is selected from a group consisting of alkoxy, —OH, —NH₂, —NHR¹, —NR¹R², —SH, or —SR¹, lower alkyl group, aryl group, heteroaryl group, aralkyloxy, benzyl, benzoyl, ester, carboxylic acid, aldehyde or amide, Y is selected from a group consisting of —NH, —O, —S, —C═O, (CH₂)n, —CHR³, or —CR³R⁴, wherein n is 1 to 5, R³ and R⁴ are each independently selected from —H, —F, —Cl, —Br, —I, —NH₃, —NHR¹, —NR¹R², alkoxy, aryl, lower alkyl group, aralkyloxy, benzyl, benzoyl, ester, carboxylic acid or amide, Z is selected from a group consisting of —NH, —O, —S, —C═O, (CH₂)n, —CHR³, or —CR³R⁴, wherein n is 0 to 5, R³ and R⁴ are each independently selected from —H, —F, —Cl, —Br, —I, —NH₃, —NHR¹, —NR¹R², alkoxy, aryl, lower alkyl group, aralkyloxy, benzyl, benzoyl, or amide, R⁵, R⁶, R⁷ and R⁸ are separately straight chain or branched non-cyclic lower alkyl group; wherein R⁵ is selected from a group consisting of —H, —F, —Cl, —Br, —I, alkoxy, aryl, aralkyloxy, —CF₃, —OCF₃, —CN, —CONHR¹, —CONR¹R², —SO₂CH₃, —SO₂NHR¹, R⁹ is selected from —H, —F, —Cl, —Br, —I, —N—(C1-C12)-alkyl, N-aryl, —N-aralkyl, benzyl, benzyloxy, alkoxy, aryl, aralkyloxy, —SH, —S—(C1-C12)-alkyl, —S-aryl, —SO₂, CF₃, —OCF₃, —CN, —CONHR¹, —CONR¹R², —SO₂CH₃, or —SO₂NHR¹, or a pharmaceutically acceptable salt, hydrate, solvate, or derivative thereof.

Also provided are pharmaceutical compositions including the compounds according to Formula I or Formula II, or a pharmaceutically acceptable salt, hydrate, solvate, or derivative thereof and optionally a pharmaceutically acceptable excipient. In one embodiment, the pharmaceutical composition can also include cyclophosphamide.

Another embodiment provides methods for inhibiting or reducing cancer cell metastasis in a subject in need thereof. The method includes administering to the subject in need thereof a composition containing an effective amount of at least one calprotectin inhibitor. In one embodiment, the calprotectin inhibitor is a compound according to Formula I or Formula II, or a pharmaceutically acceptable salt, hydrate, solvate, or derivative thereof. In another embodiment, the calprotectin inhibitor is a compound selected from the group consisting of NSC37627, NSC60785, and NSC727038. In one embodiment, the metastatic inhibition occurs through the inhibition of the induction of granulocytic myeloid derived suppressor cells (gMDSCs) in the tumor microenvironment of the subject.

In one embodiment, the subject in need thereof has or is suspected of having a cancer selected from the group consisting of bladder, brain, breast, cervical, colo-rectal, esophageal, kidney, liver, lung, nasopharangeal, pancreatic, prostate, skin, stomach, uterine, ovarian, testicular and hematologic cancer. The stage of cancer can be pre-metastatic or metastatic.

In one embodiment, the disclosed compositions are administered parenterally or enterally. In some embodiments, the disclosed compositions are administered to the subject with a second active agent including, but not limited to one or more chemotherapeutic agents.

In another embodiment, the disclosed compositions are administered in combination with at least one other cancer therapeutic or chemotherapeutic agent selected from the group consisting of alkylating agents, cancer immunotherapeutic agents, or cytotoxic/cytostatic agents. The alkylating agent can be selected from the group consisting of cyclophosphamide, chlorambucil, mechhlorethamine, cisplatin, oxaliplatin, carboplatin, temolozomide, melphalan, streptozocin, busulfan, bendamustine, and trabectedin. The cancer immunotherapeutic agent can be selected from the group containing alemtuzumab, trastuzumab, bevacizumab, cetuximab, ibritumomab tiuxetan, brentuximab vedotin, ado-trastuzumab emtansine, denileukin diftitox, and blinatumomab. The cytotoxic/cytostatic agent can be selected from the group containing 5-Fluorouracil, Doxorubicin, Daunorubicin, lonidamine, altretamine, prednimustine, dibromodulcitol, ranimustine, fotemustine, nedaplatin, temozolomide, hepaplatin, estramustine, improsulfan tosilate, trofosfamide, nimustine, dibrospidium chloride, pumitepa, lobaplatin, Pemetrexed, bevacizumab, cetuximab, tositumonab, Bortezomib, Gefitinib, Ibritumomab tiuxetan, Imatinib mesylate, alemtuzumab, arsenic trioxide, gemtuzumab, temozolomide, valrubicin, tanstuzumab, capecitabine, rituximab, interferon-a, topotecan, gemcitabine, topotecan, docetaxel, tretinoin, navelbine, claribine, paclitaxel, bisantrene, mitoxantrone, and elinafide.

Another embodiment provides a method for reducing tumor size or tumor burden in a subject in need thereof by administering to the subject an effective amount of a pharmaceutical composition containing a compound according to any one of Formula I or Formula II, or a pharmaceutically acceptable salt, hydrate, solvate, or derivative thereof.

BRIEF DESCRIPTION OF THE DRAWINGS

FIGS. 1A-1B and FIGS. 1F-1G are representative histological images that show early 4T1 tumor lung-infiltration in mice 1 or 2 weeks after tumor implantation. FIG. 1C and FIG. 1H are representative histological images that show lung metastases in mice 3 weeks after tumor implantation. FIG. 1D and FIG. DI are representative gross images of lung mets in mice 8 weeks after tumor implantation. FIG. 1E and FIG. 1J are representative full body imaging photos showing lung metastases in mice 8 weeks after tumor implantation. FIG. 1K shows representative spleens from EMT6 and 4T1 tumor bearing mice and FIG. 1L is a bar graph showing the average weight (g) of the spleens. FIG. 1M-1R are cytokine arrays for noninvasive cells (67NR and EMT6) and invasive 4T1 tumor cells. FIG. 1S is a line graph showing the results of the cytokine arrays of FIGS. 1M-1R. White bars represent EMT6, gray bars represent 67NR, and black bars represent 4T1. The X axis represents the cytokine and the Y axis represents intensity in relative units.

FIGS. 2A-2H are bar graphs showing systemic induction of mMDSC (% Ly6C$^{hi}$ CD11b+ cells) (FIGS. 2A-2D) and gMDSC (% Ly6Cint+CD11b+ cells) (FIGS. 2E-2H) in bone marrow, spleen, lung, and tumor tissue from 4T1 and EMT6 tumor-bearing BALB/c mice at week 1, week 2 and week 3 after tumor implantation (Control (white bar), EMT6 (hatched bar), and 4T1 (black bar)). FIGS. 2I-2O are representative flow cytometry plots analyzing MDSC subsets in bone marrow on week 1, week 2 and week 3 post tumor implantation. FIGS. 2P-2W are bar graphs showing systemic induction of mMDSC (% Ly6C$^{hi}$ CD11b+ cells) (FIGS. 2P-2S) and gMDSC (% Ly6Cint+CD11b+ cells) (FIGS. 2T-2W) in bone marrow, spleen, lung, and tumor tissue from AT3 tumor-bearing C57BL/6J mice at week 1, week 2 and week 3 after tumor implantation (Control (white bar) and 4T1 (black bar)).

FIG. 3W is a bar graph showing the expression of vimentin and twist in EMT6, EMT6+mMDSC, EMT6+gMDSC, 4T1+mMDSC, and 4T1+gMDSC. The Y axis represents relative fold increase. FIG. 3X-3Z are microcopy images showing invasion assays of tumor cells (FIG. 3X), tumor cells+mMDSC (FIG. 3Y), and tumor cells+gMDSC (FIG. 3Z). FIG. 3AA is a bar graph showing the results of the invasion assay. White bar represents tumor cells, gray bar represents tumor cells+mMDSC, and black bar represents tumor cells+gMDSC. The Y axis represents number of invaded cells. FIG. 3BB is a bar graph that shows percent CD24+CD29+ cells out of total cells in tumor cells (white bar), tumor cells+mMDSC (gray bar), and tumor cells+ gMDSC (black bar). FIG. 3CC is a bar graph that shows the number of tumor spheres formed from tumor cells (white bar), tumor cells+mMDSC (gray bar), and tumor cells+ gMDSC (black bar). FIGS. 3DD-3II are representative fluorescent microscopy images of vimentin staining in primary tumors two weeks after implantation. FIGS. 3JJ-3OO are representative histology images of lung H&E staining, Ki67 staining and Ly6 staining in lung metastases 5 weeks after tumor implantation. FIGS. 3PP-3QQ are histology images showing CD14 staining in metastatic tumors and indolent tumors from human breast cancer samples.

FIG. 4A is a heat map from mouse transcriptome analysis of MDSC subsets from 4T1 tumor-bearing mice. FIG. 4B-4C is a heat map from mouse transcriptome analysis of tumor cells co-cultured with MDSC subsets. FIGS. 4D-4G are bar graphs showing expression of EMT-related genes (IL6, FIG. 4D; IL1A, FIG. 4E; NOS2, FIG. 4F; TGFB1, FIG. 4G) in tumor cells (white bars), tumor cells co-cultured with BM mMDSCs (gray bars), and tumor cells co-cultured with BM gMDSCs (black bars) from 4T1 tumor bearing BALB/c mice. FIGS. 4H-4L are bar graphs showing expression of EMT-related genes (IL6, FIG. 4H; IL1A, FIG. 4I; NOS2, FIG. 4J; TGFB1, FIG. 4K; VIM, FIG. 4L) in tumor cells (white bars), tumor cells co-cultured with tumor mMDSCs (gray bars), and tumor cells co-cultured with tumor gMDSCs (black bars) from 4T1 tumor bearing mice. FIGS. 4M-4P are bar graphs showing expression of EMT-related genes (IL6, FIG. 4M; IL1A, FIG. 4N; NOS2, FIG. 4O; TGFB1, FIG. 4P) in tumor cells (white bars), tumor cells co-cultured with BM mMDSCs (gray bars), and tumor cells co-cultured with BM gMDSCs (black bars) in AT-3 tumor bearing C57BL/6J mice. FIGS. 4Q-4U are bar graphs showing expression of EMT-related genes (IL6, FIG. 4Q; IL1A, FIG. 4R; NOS2, FIG. 4S; TGFB1, FIG. 4T; VIM, FIG. 4U) in tumor cells (white bars), tumor cells co-cultured with tumor mMDSCs (gray bars), and tumor cells co-cultured with tumor gMDSCs (black bars) from AT-3 tumor bearing C57BL/6J mice. FIGS. 4V-4W are representative Western blots showing expression of pSTAT3, STAT3, pSTAT1, STAT1, pNFκB, vimentin, pERK1/2, ERK1/2, Twist1, and actin in EMT6 cells alone, with mMSDCs, and with gMDSC in 4T1 tumor bearing mice (FIG. 4V) and AT3 tumor bearing mice (FIG. 4W).

FIGS. 5A-5D are bar graphs showing expression of IL6 (FIG. 5A), IL1A (FIG. 5B), TGFB (FIG. 5C), and Vimentin (FIG. 5D) in EMT6 cells (white bars), EMT6 cells+0.5 mM DPTA (gray bars), and EMT6 cells+2.5 mM DPTA (black bars).

FIGS. 6A-6O are representative fluorescent microscopy images showing Ki67 staining in tumor cells, tumor cells co-cultured with bone marrow derived mMDSC and gMDSC, tumor cells co-cultured with tumor derived gMDSC, and tumor cells co-cultured with lung derived gMDSCs. FIG. 6P is a bar graph showing the percent Ki-67 positive cells in tumor control cells, tumor cells co-cultured with bone marrow derived mMDSC and gMDSC, tumor cells co-cultured with tumor derived gMDSC, and tumor cells co-cultured with lung derived gMDSCs. FIG. 6Q is a bar graph showing relative fold increase of EpCAM in in tumor control cells, tumor cells co-cultured with bone marrow derived mMDSC and gMDSC, tumor cells co-cultured with tumor derived gMDSC, and tumor cells co-cultured with lung derived gMDSCs. FIGS. 6T-6Y are bar graphs that show expression of metastatic genes (S100A9, FIG. 6T; MMP8, FIG. 6U; S100A8, FIG. 6V; CCL3, FIG. 6W; TGFB2, FIG. 6X; PCNA, FIG. 6Y) in tumor cells (white bars), tumor cells+BM mMDSCs (gray bars), and tumor cells+BM gMDSCs (black bars) in 4T1 tumor bearing mice. FIGS. 6Z-6EE are bar graphs that show expression of metastatic genes (S100A9, FIG. 6Z; MMP8, FIG. 6AA; S100A8, FIG. 6BB; CCL3, FIG. 6CC; TGFB2, FIG. 6DD; PCNA, FIG. 6EE) in tumor cells (white bars), tumor cells+lung mMDSCs (gray bars), and tumor cells+lung gMDSCs (black bars) in 4T1 tumor bearing mice. FIGS. 6FF-6KK are bar graphs that show expression of metastatic genes (S100A9, FIG. 6FF; MMP8, FIG. 6GG; S100A8, FIG. 6HH; CCL3, FIG. 6II; TGFB2, FIG. 6JJ; PCNA, FIG. 6KK) in tumor cells (white bars), tumor cells+BM mMDSCs (gray bars), and tumor cells+BM gMDSCs (black bars) in AT3 tumor bearing mice. FIGS. 6LL-6QQ are bar graphs that show expression of metastatic genes (S100A9, FIG. 6LL; MMP8, FIG. 6MM; S100A8, FIG. 6NN; CCL3, FIG. 6OO; TGFB2, FIG. 6PP; PCNA, FIG. 6QQ) in tumor cells (white bars), tumor cells+lung mMDSCs (gray bars), and tumor cells+lung gMDSCs (black bars) in AT3 tumor bearing mice.

FIG. 7A is a survival curve from a TCGA data set showing the correlation between S100A8, S100A9, MMp8, CC13, FPR1, and TGFb2 and survival in breast cancer patients. FIG. 7B is a scatter plot of TCGA data set showing the correlation between the metastatic signature and PCNA expression in tumors. FIG. 7C is a survival curve showing the correlation between PCNA expression (high or low) and survival in breast cancer patients. FIG. 7D is a survival curve showing the correlation between metastatic gene signature, PCNA expression (high or low), and breast cancer survival. FIG. 7E-7L are survival curves showing correlation between metastatic gene signature expression (high or low) and survival rate in brain lower grade glioma (FIG. 7E), colorectal adenocarcinoma (FIG. 7F), cutaneous melanoma (FIG. 7G), endometrial carcinoma (FIG. 7H), stomach adenocarcinoma (FIG. 7I), renal clear cell carcinoma (FIG. 7J), ovarian serous adenocarcinoma (FIG. 7K), prostate adenocarcinoma (FIG. 7L), and hepatocellular carcinoma (FIG. 7M).

FIGS. 8D-8E is a representative flow cytometry plot showing expression of CD11b and Ly6C in EMT6-Luci cells alone or in combination with a conditioned medium from 4T1 cells. FIGS. 8F-8G are full body scan images of metastatic growth in naïve BALB/c mice or 4T1-primed mice (in which primary 4T1 tumors resected after 10 days) IV injected with EMT6-Luci cells (50 k per per injection). FIGS. 8H-8M are full body scan images of mice co-injected with 4T1-luci cells (50 k per injection) and flow cytometry sorted tumor-derived mMDSCs (100 k) or lung-derived gMDSCs (100 k) from 4T1 tumor-bearing mice. The injections were repeated after one week (FIGS. 8K-8M). FIG. 8N is a survival curve for control mice (solid line), mice co-injected with mMDSCs (dashed line), or mice co-injected with lung-derived gMDSCs.

FIG. 10A-10C are full body scan images that show mice with no metastatic growth when primary tumors are resected at 1 week post implantation despite the existence of disseminated tumor cells in regional lymph nodes and lungs as shown in histological images (FIG. 10D-10E). FIGS. 10F-10H are full body scan images showing metastases in mice when primary tumors were resected at 2 weeks post implantation. FIG. 10I is a schematic illustration of the experimental design. FIG. 10J-10K are full body bioluminescence imaging of metastases in mice with primary 4T1-Luci tumors that were resected after 1 week post implantation. FIG. 10L-10M shows full body bioluminescence imaging of mice that were injected (via tail vein) with tumor-derived mMDSCs as indicated after resection of primary tumors. FIG. 10N-10P are full body bioluminescence imaging of mice injected with lung-derived gMDSCs after tumor resection.

FIG. 11B-11D are full body bioluminescence imaging showing tumor metastases in mice treated with saline (FIG. 11B), S100A9 (FIG. 11C), or calprotectin (FIG. 11D). FIGS. 11E-11J show ex vivo lung images. FIG. 11K is a bar graph that shows lung MDSCs in mice treated with saline (white bar), S100A9 (gray bar), or calprotectin (black bar). FIG. 11L is a bar graph that shows CD8+ T cells in mice treated with saline (white bar), S100A9 (gray bar), or calprotectin (black bar). FIG. 11M is a bar graph that shows annexin V+ cells in mice treated with saline (white bar), S100A9 (gray bar), or calprotectin (black bar). FIG. 11N is a bar graph showing caspase 3 positive cells in mice treated with saline (white bar), S100A9 (gray bar), or calprotectin (black bar).

FIGS. 13B-13K are representative flow cytometry plots showing the expression of CD11b and Ly6C in bone marrow cells treated with compounds 4, 10, 13, and 15. FIGS. 13L-13R are bar graphs showing the expression of MDSC-related genes (S100A8, FIG. 13L; S100A9, FIG. 13M; GCSF, FIG. 13N; IL1A, FIG. 13O; NOS2, FIG. 13P; CYB1, FIG. 13Q; and IL4R, FIG. 13R) in bone marrow cells treated with GCSF (black bars), GCSF+#4 (dark gray bars), GCSF+#10 (light gray bars), or untreated (white bars).

FIG. 14A-14D are bioluminescence images of metastatic 4T1-injected mice untreated or treated with drug #10. FIG. 14E-14H are bar graphs showing the extent of mMDSC infiltration in the primary tumor (FIG. 14H) and the BM (FIG. 14E), spleen (FIG. 14F), and lung (FIG. 14G) of metastatic 4T1-injected mice untreated (black bars) or treated with drug #10 (gray bars). FIG. 14I-14L are bar graphs showing the extent of gMDSC infiltration in the primary tumor (FIG. 14L) and the BM (FIG. 14I), spleen (FIG. 14J), and lung (FIG. 14K) of metastatic 4T1-injected mice untreated (black bars) or treated with drug #10 (gray bars).

DETAILED DESCRIPTION OF THE INVENTION

I. Definitions

Figure 1T:
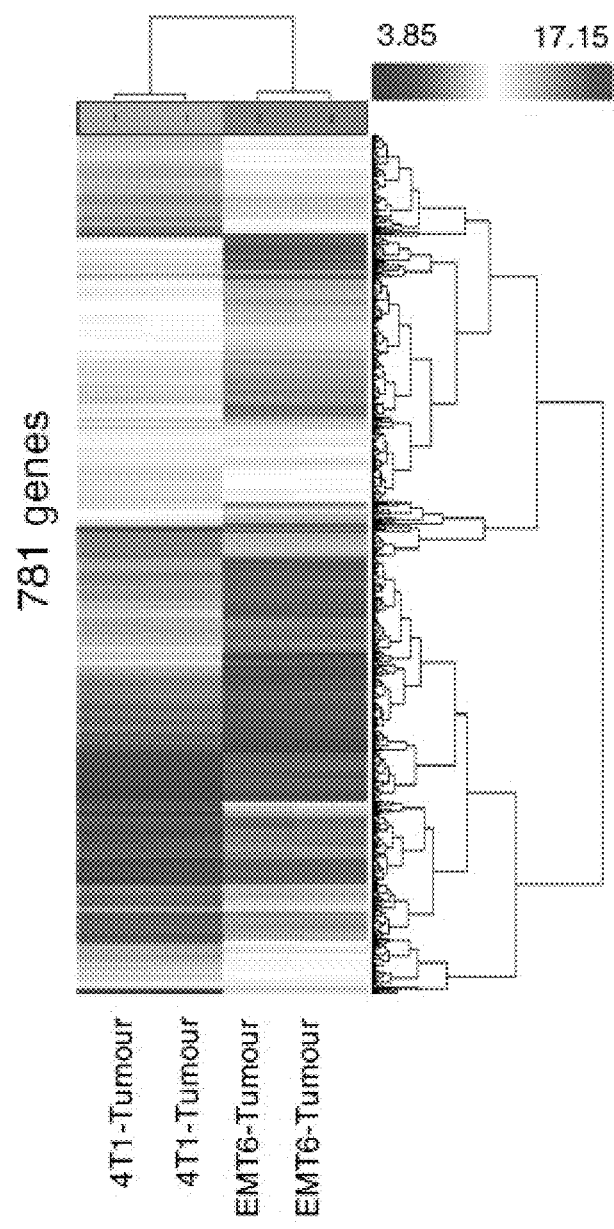
FIG. 1T is a heat map showing transcriptome analysis of 4T1 and EMT6 tumors.

As used herein, the singular forms "a," "an," and "the" include plural referents unless the context clearly dictates otherwise. For example, reference to "the method of treatment" includes reference to equivalent steps and methods known to those skilled in the art, and so forth.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx.+/−10%; in other embodiments, the values may range in value either above or below the stated value in a range of approx.+/−5%; in other embodiments, the values may range in value either above or below the stated value in a range of approx. +/−2%; in other embodiments, the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The terms "treat," "treating," or "treatment" refers to alleviating, reducing, or inhibiting one or more symptoms or physiological aspects of a disease, disorder, syndrome, or condition. "Treatment" as used herein covers any treatment of a disease in a subject, and includes: (a) preventing the disease or symptom from occurring in a subject which may be predisposed to the disease or symptom, but has not yet been diagnosed as having it; (b) inhibiting the disease symptom, i.e., arresting its development; or (c) relieving the disease symptom, i.e., causing regression of the disease or symptom.

The term "pharmaceutically acceptable" refers to derivatives of the compounds defined herein, wherein the parent compound is modified by making acid or base salts thereof.

The term "effective amount" or "therapeutically effective amount" means a dosage sufficient to provide treatment a disorder, disease, or condition being treated, or to otherwise provide a desired pharmacologic and/or physiologic effect. The precise dosage will vary according to a variety of factors such as subject-dependent variables (e.g., age, immune system health, etc.), the disease, and the treatment being effected.

The terms "individual," "individual," "subject," and "patient" are used interchangeably herein, and refer to a mammal, including, but not limited to, humans, rodents, such as mice and rats, and other laboratory animals.

As used herein, "cancer" refers to the uncontrolled growth of abnormal cells in the body. Unregulated cell division and growth results in the formation of malignant tumors that invade neighboring tissues and may also metastasize to distant parts of the body through the lymphatic system or bloodstream.

As used herein, "metastasis" refers to the movement of cancer cells from a primary site to a secondary site. In some instances, the movement to the secondary site results in the development of secondary malignant growths in a site in the body distant from the primary site of the cancer.

As used herein, "MDSC" and "myeloid-derived suppressor cell" can be used interchangeably and refer to a heterogeneous group of immune cells from the myeloid lineage that are known to be increased in states of cancer, inflammation, and infection. MDSCs are capable of suppressing immune responses through the production of arginase 1, iNOS, IDO, NADPH and other suppressive cytokines that have the potential to inhibit cytotoxic T lymphocytes (CTLs), dendritic cells (DC), and natural killer (NK) cells as well as expand CD4+CD25+FoxP3+ regulatory T cells (Tregs).

The term "alkyl" refers to the radical of saturated aliphatic groups (i.e., an alkane with one hydrogen atom removed), including straight-chain alkyl groups, branched-chain alkyl groups, cycloalkyl (alicyclic) groups, alkyl-substituted cycloalkyl groups, and cycloalkyl-substituted alkyl groups.

In preferred embodiments, a straight chain or branched chain alkyl has 30 or fewer carbon atoms in its backbone (e.g., C1-C30 for straight chains, and C3-C30 for branched chains), preferably 20 or fewer, more preferably 15 or fewer, most preferably 10 or fewer. Likewise, preferred cycloalkyls have 3-10 carbon atoms in their ring structure, and more preferably have 5, 6, or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthiols, carbonyls (including ketones, aldehydes, carboxylates, and esters), —CF$_3$, —CN and the like. Cycloalkyls can be substituted in the same manner.

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The terms "alkenyl" and "alkynyl", refer to unsaturated aliphatic groups analogous in length and possible substitution to the alkyls described above, but that contain at least one double or triple bond respectively.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. The terms "aroxy" and "aryloxy", as used interchangeably herein, can be represented by —O-aryl or O-heteroaryl, wherein aryl and heteroaryl are as defined below. The alkoxy and aroxy groups can be substituted as described above for alkyl.

"Aryl", as used herein, refers to C5-C10-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those aryl groups having heteroatoms in the ring structure may also be referred to as "aryl heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. One or more of the rings can be substituted as defined above for "aryl".

The term "aralkyl", as used herein, refers to an alkyl group substituted with an aryl group (e.g., an aromatic or heteroaromatic group).

The term "aralkyloxy" can be represented by —O-aralkyl, wherein aralkyl is as defined above.

The term "heteroatom" as used herein means an atom of any element other than carbon or hydrogen. Preferred heteroatoms are boron, nitrogen, oxygen, phosphorus, sulfur, and selenium. Other heteroatoms include silicon and arsenic.

As used herein, the term "nitro" means —NO$_2$; the term "halogen" designates —F, —Cl, —Br, or —I; the term "sulfhydryl" means —SH; the term "hydroxyl" means —OH; and the term "sulfonyl" means —SO$_2$—.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats.

Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, C3-C20 cyclic, substituted C3-C20 cyclic, heterocyclic, substituted heterocyclic, amino acid, peptide, and polypeptide groups.

Compounds discussed in the present invention can exist as stereoisomers, wherein asymmetric or chiral centers are present. Stereoisomers are designated (R) or (S) depending on the configuration of substituents around the chiral carbon atom. The terms (R) and (S) used herein are configurations as defined in IUPAC 1974 Recommendations for Section E, Fundamental Stereochemistry, Pure Appl. Chem., (1976), 45: 13-30, hereby incorporated by reference.

"Calprotectin" is a complex of the mammalian proteins S100A8 and S100A9 that is expressed during myeloid differentiation. The two subunits of calprotectin are calcium- and zinc-binding proteins that play a prominent role in the regulation of inflammatory processes and immune response. The S100A8/S100A9 complex (calprotectin) has many intracellular functions including but not limited to facilitating leukocyte arachidonic acid trafficking and metabolism, modulating the tubulin-dependent cytoskeleton during migration of phagocytes, and activation of the neutrophilic NADPH-oxidase. Extracellular functions of calprotectin include but are not limited to proinflammatory, antimicrobial, oxidant-scavenging and apoptosis-inducing activities.

The proinflammatory activity includes recruitment of leukocytes, promotion of cytokine and chemokine production, and regulation of leukocyte adhesion and migration.

II. Compositions for Inhibiting Calprotectin

Compounds and pharmaceutical compositions thereof for inhibiting, reducing, or preventing cancer cell metastasis are provided herein. In one embodiment, the compounds and compositions are calprotectin inhibitors. It has been discovered that the compounds according to Formulas I-II or a pharmaceutically acceptable salt, hydrate, solvate, or derivatives thereof can inhibit calprotectin. In one embodiment, these compounds bind to calprotectin and inhibit the induction of gMDSCs. In one embodiment, the inhibition of the induction of gMDSCs inhibits, reduces, or prevents cancer cell metastasis.

A. Compounds

One embodiment provides a compound having a structure according to Formula I or a derivative thereof, as follows:

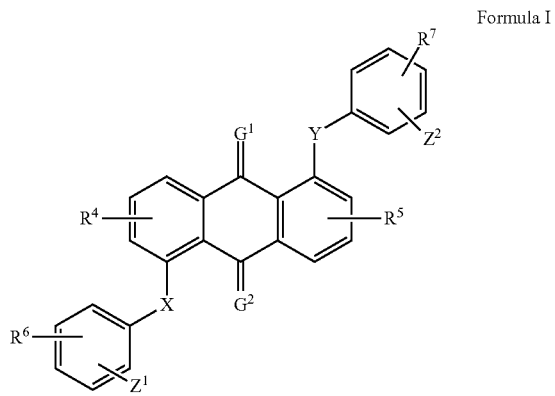

Formula I wherein:

$G^1$ and $G^2$ are each independently —O, —S, —NH, —$NR^1$, —$CH_2$, —$CHR^1$, —$CR^1R^2$, X and Y are each independently —O, —NH, —$NR^1$, or —S, wherein each occurrence of $R^1$ is selected from straight chain or branched non-cyclic lower alkyl group, $R^4$, $R^5$, $R^6$, and $R^7$ are separately selected from a group consisting of —H, —F, —Cl, —Br, —I, alkoxy group, —$CF_3$, —$OCF_3$, —CN, —$CONHR^2$, —$CONR^2R^3$, —$SO_2CH^3$, —$SO_2NHR^3$, $Z^1$ and $Z^2$ may separately be an —H, —F, —Cl, —Br, —I, —N—(C1-C12)-alkyl, N-aryl, —N-aralkyl, benzyl, benzyloxy, alkoxy, aryl, aralkyloxy, —SH, —S—(C1-C12)-alkyl, —S-aryl, —$SO_2$, $CF_3$, —$OCF_3$, —CN, —$CONHR^1$, —$CONR^1R^2$, —$SO_2CH_3$, or —$SO_2NHR^1$, or a pharmaceutically acceptable salt, hydrate, solvate, or derivative thereof.

In another embodiment the compound can be a derivative of Formula I wherein each occurrence of $R^1$, $R^2$ or $R^3$ is independently selected from straight chain or branched chain lower alkyl group, aryl group, substituted alkyl group, substituted aryl, heteroaryl, aralkyloxy, alkoxy, benzyl, phenyl, ester, carboxylic acid or amide, or a pharmaceutically acceptable salt, hydrate, solvate, or derivative thereof.

Another embodiment provides a compound having a structure according to Formula II or a derivative thereof, as follows:

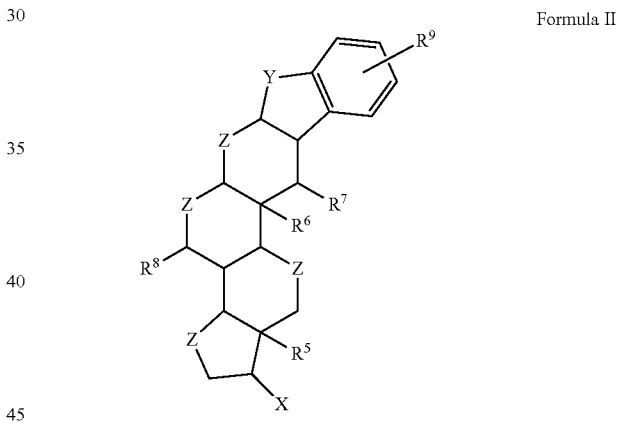

Formula II wherein:

X is selected from a group consisting of alkoxy, —OH, —$NH_2$, —$NHR^1$, —$NR^1R^2$, —SH, or —$SR^1$, lower alkyl group, aryl group, heteroaryl group, aralkyloxy, benzyl, benzoyl, ester, carboxylic acid, aldehyde or amide, Y is selected from a group consisting of —NH, —O, —S, —C═O, $(CH_2)n$, —$CHR^3$, or —$CR^3R^4$, wherein n is 1 to 5, $R^3$ and $R^4$ are each independently selected from —H, —F, —Cl, —Br, —I, —$NH_3$, —$NHR^1$, —$NR^1R^2$, alkoxy, aryl, lower alkyl group, aralkyloxy, benzyl, benzoyl, ester, carboxylic acid or amide, Z is selected from a group consisting of —NH, —O, —S, —C═O, $(CH_2)n$, —$CHR^3$, or —$CR^3R^4$, wherein n is 0 to 5, $R^3$ and $R^4$ are each independently selected from —H, —F, —Cl, —Br, —I, —$NH_3$, —$NHR^1$, —$NR^1R^2$, alkoxy, aryl, lower alkyl group, aralkyloxy, benzyl, benzoyl, or amide, $R^5$, $R^6$, $R^7$ and $R^8$ are separately straight chain or branched non-cyclic lower alkyl group; wherein $R^5$ is selected from a group consisting of —H, —F, —Cl, —Br, —I, alkoxy, aryl, aralkyloxy, —$CF_3$, —$OCF_3$, —CN, —$CONHR^1$, —$CONR^1R^2$, —$SO_2CH_3$, —$SO_2NHR^1$, $R^9$ is selected from —H, —F, —Cl, —Br, —I, —N—(C1-C12)-alkyl, N-aryl, —N-aralkyl, benzyl, benzyloxy, alkoxy, aryl, aralkyloxy, —SH, —S—(C1-C12)-alkyl, —S-aryl, —SO$_2$, CF$_3$, —OCF$_3$, —CN, —CONHR$^1$, —CONR$^1$R$^2$, —SO$_2$CH$_3$, or —SO$_2$NHR$^1$, or a pharmaceutically acceptable salt, hydrate, solvate, or derivative thereof.

In another embodiment of the compound of formula II, $R^1$ and $R^2$ are each independently selected from —H, -alkyl, aryl, or heteroaryl.

In one embodiment, compounds according to Formula I and Formula II are calprotectin inhibitors that to bind to calprotectin. Calprotectin is a heterotetramer complex of S100A8 and S100A9. In one embodiment, the calprotectin inhibitors bind to and inhibit the S100A8 subunit of calprotectin or the S100A9 subunit of calprotectin to disrupt the heterotertramer complex of S100A8 and S100A9.

1. Pharmaceutically Acceptable Salts

Also disclosed herein are pharmaceutically acceptable salts of the compounds represented by Formulas I-II. Pharmaceutically acceptable salts are known in the art. Examples of pharmaceutically acceptable salts include but are not limited to mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, naphthalenesulfonic, methanesulfonic, ethane disulfonic, oxalic, and isethionic salts.

The pharmaceutically acceptable salts of the compounds can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile as preferred. Lists of suitable salts are found in Remington's Pharmaceutical Sciences, 20th ed., Lippincott Williams & Wilkins, Baltimore, Md., 2000, p. 704; and "Handbook of Pharmaceutical Salts: Properties, Selection, and Use," P. Heinrich Stahl and Camille G. Wermuth, Eds., Wiley-VCH, Weinheim, 2002.

2. Intermediates

The compounds identified herein using virtual ligand screening can be used as a starting compound or intermediate compound to produce a final compound that has increased binding to a protein, for example calprotectin, or increased inhibition of the protein, for example calprotectin, relative to starting compound or intermediate compound. The compounds identified herein can be modified to increase bioavailability, increase half-life in the blood stream, increase solubility, increase hydrophilicity, increase hydrophobicity, or a combination thereof using conventional techniques.

The compounds can be modified to incorporate polar functional groups, such as the alcohol, amine, amide, carboxylic acid, sulfonic acid and phosphate groups, which either ionize or are capable of relatively strong intermolecular forces of attraction with water (hydrogen bonding), usually resulting in analogues with an increased water solubility. Acidic and basic groups are particularly useful, since these groups can be used to form salts, which would give a wider range of dosage forms for the final product. However, the formation of zwitterions by the introduction of either an acid group into a structure containing a base or a base group into a structure containing an acid group can reduce water solubility. Introduction of weakly polar groups, such as carboxylic acid esters, aryl halides and alkyl halides, will not significantly improve water solubility and can result in enhanced lipid solubility.

The incorporation of acidic residues into the compound is less likely to change the type of activity, but it can result in the analogue exhibiting hemolytic properties. Furthermore, the introduction of an aromatic acid group usually results in anti-inflammatory activity, whilst carboxylic acids with an alpha functional group may act as chelating agents. Basic water solubilizing groups have a tendency to change the mode of action, since bases often interfere with neurotransmitters and biological processes involving amines. However, their incorporation does mean that the analogue can be formulated as a wide variety of acid salts. Non-ionizable groups do not have the disadvantages of acidic and basic groups.

Groups that are bound directly to the carbon skeleton of the lead compound by less reactive C—C, C—O and C—N bonds are likely to be irreversibly attached to the lead structure. Groups that are linked to the compound by ester, amide, phosphate, sulfate and glycosidic bonds are more likely to be metabolized from the resulting analogue to reform the parent compound as the analogue is transferred from its point of administration to its site of action. Compounds with this type of solubilizing group are acting as prodrugs and so their activity is more likely to be the same as the parent compound. However, the rate of loss of the solubilizing group will depend on the nature of the transfer route, and this could affect the activity of the drug.

To preserve the type of activity exhibited by the compound, a water solubilizing group can be attached to a part of the structure that is not involved in the drug-receptor interaction. Consequently, the route used to introduce a new water solubilizing group and its position in the lead compound will depend on the relative reactivities of the compound and the rest of the molecule. Examples of water solubilizing structures and the routes used to introduce them into the lead structures include but are not limited to N-alkyl-N-alkyloxycarbonylaminomethyl chlorides; ethyl-, propyl-, butyl- and longer chain chlorides or bromides or iodides; tertiary butyl chlorides or bromides, tetradecyloxymethyl halides, phosphoryloxy methyl groups, N-Mannich bases, monoethyl esters, pivaloylmethyl esters, bis-(pivaloyloxy-methy)esters, and bis-(isoproyloxy-carbonyloxymethyl)esters. O-alkylation, N-alkylation, O-acylation and N-acylation reactions are used to introduce both acidic and basic groups. Acetylation methods use both the appropriate acid chloride and anhydride.

Examples of water solubilizing structures and the routes used to introduce them into lead compounds include but are not limited to phosphate acid halides for introducing phosphate groups into compounds. Structures containing hydroxy groups have been introduced by reaction of the corresponding monochlorinated hydrin and the use of suitable epoxides or sulphonic acid groups may be introduced by either direct sulfonation or the addition of bisulfite to reactive C═C bonds.

C. Pharmaceutical Compositions

Pharmaceutical compositions including the disclosed calprotectin inhibitors are provided. Pharmaceutical compositions containing the calprotectin inhibitors can be formulated for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration.

In some in vivo approaches, the compositions disclosed herein are administered to a subject in a therapeutically effective amount. The precise dosage will vary according to a variety of factors such as subject-dependent variables (e.g., age, immune system health, etc.), the disease, and the treatment being effected.

For the disclosed calprotectin inhibitors, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. For the disclosed calprotectin inhibitors, generally dosage levels of 0.001 to 20 mg/kg of body weight are administered to mammals daily. Generally, for intravenous injection or infusion, dosage may be lower.

In certain embodiments, the calprotectin inhibitor is administered locally, for example by injection directly into a site to be treated. Typically, the injection causes an increased localized concentration of the calprotectin inhibitor which is greater than that which can be achieved by systemic administration. The calprotectin inhibitors can be combined with a matrix as described above to assist in creating an increased localized concentration of the polypeptide compositions by reducing the passive diffusion of the polypeptides out of the site to be treated.

1. Formulations for Parenteral Administration

In some embodiments, calprotectin inhibitor compositions disclosed herein, are administered in an aqueous solution, by parenteral injection. The formulation may also be in the form of a suspension or emulsion. In general, pharmaceutical compositions are provided including effective amounts of calprotectin inhibitors, and optionally include pharmaceutically acceptable diluents, preservatives, solubilizers, emulsifiers, adjuvants and/or carriers. Such compositions optionally include one or more for the following: diluents, sterile water, buffered saline of various buffer content (e.g., Tris-HCl, acetate, phosphate), pH and ionic strength; and additives such as detergents and solubilizing agents (e.g., TWEEN 20 (polysorbate-20), TWEEN 80 (polysorbate-80)), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Formulations for Oral Administration

In some embodiments the compositions are formulated for oral delivery. Oral solid dosage forms are described generally in Remington's Pharmaceutical Sciences, 18th Ed. 1990 (Mack Publishing Co. Easton Pa. 18042) at Chapter 89. Solid dosage forms include tablets, capsules, pills, troches or lozenges, cachets, pellets, powders, or granules or incorporation of the material into particulate preparations of polymeric compounds such as polylactic acid, polyglycolic acid, etc. or into liposomes. Such compositions may influence the physical state, stability, rate of in vivo release, and rate of in vivo clearance of the disclosed. See, e.g., Remington's Pharmaceutical Sciences, 18th Ed. (1990, Mack Publishing Co., Easton, Pa. 18042) pages 1435-1712 which are herein incorporated by reference. The compositions may be prepared in liquid form, or may be in dried powder (e.g., lyophilized) form. Liposomal or proteinoid encapsulation may be used to formulate the compositions. Liposomal encapsulation may be used and the liposomes may be derivatized with various polymers (e.g., U.S. Pat. No. 5,013, 556). See also Marshall, K. In: Modern Pharmaceutics Edited by G. S. Banker and C. T. Rhodes Chapter 10, 1979. In general, the formulation will include the calprotectin inhibitor (or chemically modified forms thereof) and inert ingredients which protect the inhibitor in the stomach environment, and release of the biologically active material in the intestine.

The agents can be chemically modified so that oral delivery of the derivative is efficacious. Generally, the chemical modification contemplated is the attachment of at least one moiety to the component molecule itself, where the moiety permits uptake into the blood stream from the stomach or intestine, or uptake directly into the intestinal mucosa. Also desired is the increase in overall stability of the component or components and increase in circulation time in the body. PEGylation is an exemplary chemical modification for pharmaceutical usage. Other moieties that may be used include: propylene glycol, copolymers of ethylene glycol and propylene glycol, carboxymethyl cellulose, dextran, polyvinyl alcohol, polyvinyl pyrrolidone, polyproline, poly-1,3-dioxolane and poly-1,3,6-tioxocane [see, e.g., Abuchowski and Davis (1981) "Soluble Polymer-Enzyme Adducts," in Enzymes as Drugs. Hocenberg and Roberts, eds. (Wiley-Interscience: New York, N.Y.) pp. 367-383; and Newmark, et al. (1982) J. Appl. Biochem. 4:185-189].

Another embodiment provides liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

Controlled release oral formulations may be desirable. The agent can be incorporated into an inert matrix which permits release by either diffusion or leaching mechanisms, e.g., gums. Slowly degenerating matrices may also be incorporated into the formulation. Another form of a controlled release is based on the Oros therapeutic system (Alza Corp.), i.e., the drug is enclosed in a semipermeable membrane which allows water to enter and push drug out through a single small opening due to osmotic effects.

For oral formulations, the location of release may be the stomach, the small intestine (the duodenum, the jejunum, or the ileum), or the large intestine. In some embodiments, the release will avoid the deleterious effects of the stomach environment, either by protection of the agent (or derivative) or by release of the agent (or derivative) beyond the stomach environment, such as in the intestine. To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D™, Aquateric™, cellulose acetate phthalate (CAP), Eudragit L™, Eudragit S™, and Shellac™. These coatings may be used as mixed films.

3. Formulations for Topical Administration

The disclosed calprotectin inhibitors can be applied topically. Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator.

Transdermal formulations may also be prepared. These will typically be ointments, lotions, sprays, or patches, all of which can be prepared using standard technology. Transdermal formulations may require the inclusion of penetration enhancers.

D. Dosage

When a composition according to this invention is administered into a human subject, the daily dosage will normally be determined by one skilled in the art, with the dosage generally varying according to weight, age, pre-existing conditions, disease progression stage, severity of subject's symptoms, and subject's response to the composition.

In an embodiment, a suitable amount of a calprotectin inhibitor is administered to a subject undergoing treatment for cancer. Administration can be given in an amount of inhibitor between 0.1 mg/kg of body weight to about 100 mg/kg of body weight per day, or between 0.5 mg/kg of body weight per day to 50 mg/kg of body weight per day. Another therapeutic dosage that comprises the instant composition includes from about 0.01 mg to about 1000 mg of calprotectin inhibitor. In another embodiment, the dosage comprises from about 1 mg to about 1000 mg of the disclosed calprotectin inhibitors.

In another embodiment, a suitable amount of a calprotectin inhibitor is administered as a combination therapy or an adjuvant therapy to a subject undergoing treatment for cancer. Administration can be an amount of inhibitor between 0.1 mg/kg of body weight to about 100 mg/kg of body weight per day, or between 0.5 mg/kg of body weight per day to 50 mg/kg of body weight per day. The disclosed compositions of calprotectin inhibitors can be used as a combination or an adjuvant therapy. The doses of calprotectin inhibitor for combination or adjuvants therapy includes from about 0.01 mg to about 1000 mg of calprotectin inhibitor. In another embodiment, the dosage comprises from about 1 mg to about 1000 mg of inhibitor of calprotectin.

III. Methods of Use

The disclosed calprotectin inhibitor compositions can be used, for example, to inhibit, reduce, or prevent metastasis, to treat certain types of cancer, and to increase cancer cell sensitivity to cancer chemotherapy or cancer immunotherapy.

In some embodiments, pharmaceutical compositions include compounds according to Formula I or Formula II are administered systemically. In other embodiments, the compositions are administered locally or regionally. For example, in some embodiments, compositions are delivered to or specifically target the tissue or organs in need of modulation.

In some embodiments, the effect of the composition on a subject is compared to a control. For example, the effect of the composition on a particular symptom, pharmacologic, or physiologic indicator can be compared to an untreated subject, or the condition of the subject prior to treatment. In some embodiments, the symptom, pharmacologic, or physiologic indicator is measured in a subject prior to treatment, and again one or more times after treatment is initiated. In some embodiments, the control is a reference level, or average determined based measuring the symptom, pharmacologic, or physiologic indicator in one or more subjects that do not have the disease or condition to be treated (e.g., healthy subjects). In some embodiments, the effect of the treatment is compared to a conventional treatment that is known the art. For example, if the disease to be treated is cancer and conventional treatment could a chemotherapeutic agent.

In some embodiments, the calprotectin inhibitory compositions disclosed herein are administered in combination with one or more additional active agents. The combination therapies can include administration of the active agents together in the same admixture, or in separate admixtures. Therefore, in some embodiments, the pharmaceutical composition includes two, three, or more active agents. The pharmaceutical compositions can be formulated as a pharmaceutical dosage unit, referred to as a unit dosage form. Such formulations typically include an effective amount of one or more of the disclosed immune modulating compounds.

The different active agents can have the same or different mechanisms of action. In some embodiments, the combination results in an additive effect on the treatment of the disease or disorder. In some embodiments, the combinations result in a more than additive effect on the treatment of the disease or disorder.

A. Methods of Inhibiting Metastasis

One embodiment provides a methods for inhibiting, reducing, or preventing metastasis in a subject in need thereof. An exemplary method includes steps of administering a pharmaceutical composition including the disclosed compounds having structures according to Formula I or Formula II or a pharmaceutically acceptable salt, hydrate, solvate, or derivative thereof to a subject in need thereof in an amount effective to inhibit, reduce, or prevent metastasis. Other calprotectin inhibitors that are contemplated include but are not limited to NSC37627 (also referred to as (1,5-diphenoxyanthracen-9-10-dione)), NSC60785 (also referred to as (12a,14a-dimethyl-1,2,3,3a,3b,4,5,5a,6,7,12,12a,12b, 13,14,14a-hexadecahydrocyclopenta[5,6]naphtho[2,1-b] carbazol-1-ol)), and NSC727038. In one embodiment, the disclosed compounds decrease metastasis from the tumor site by inhibiting calprotectin in the tumor microenvironment.

Figure 10Q:
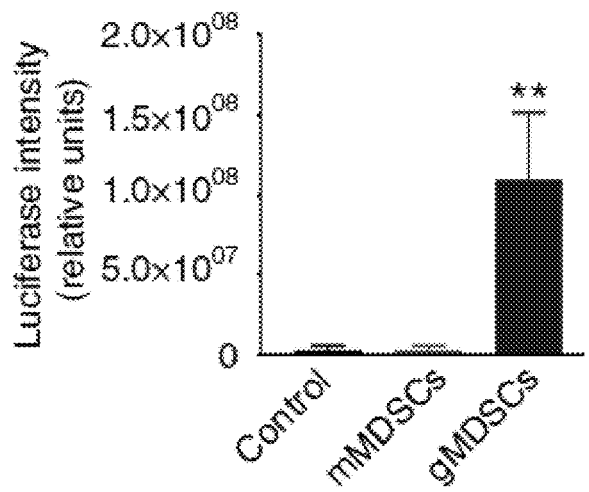
FIG. 10Q is a bar graph showing luciferase activity in control mice, mice injected with tumor-derived mMDSCs or mice injected with lung-derived gMDSCs.
Figure 10R:
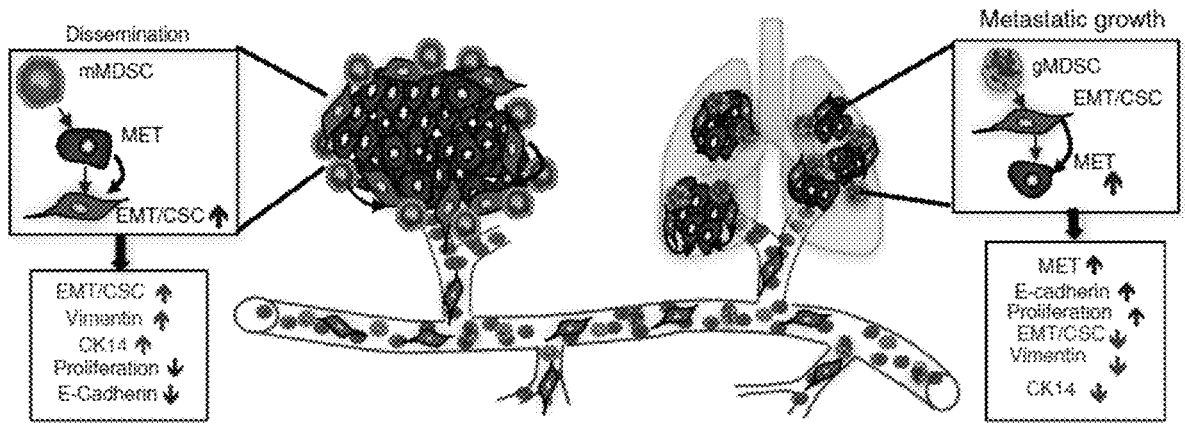
FIG. 10R is a model of the spatiotemporal regulation of tumor plasticity by MDSC subsets in primary site and in distant organs.

Without being bound to any one theory, it is belived that the disclosed compounds inhibit metastasis by inhibiting the induction of gMDSCs. gMDSCs play important roles in the metastatic process of cancer cells. gMDSCs support phenotypic transitions in cancer stem cells and subsequent proliferation of the disseminated cancer cells. gMDSCs also suppress T cells that target cancer cells. FIG. 10R shows the cascade of spatiotemporal regulation of tumor plasticity by mMDSCs and gMDSCs during metastasis. Calprotectin plays a key role in induction of gMDSCs, suppression of T cells and creation of pre-metastatic niche. By inhibiting calprotectin, gMDSC population in tumor microenvironment are drastically decreased, thereby increasing the susceptibility of cancer or tumor cells to T cell mediated apoptosis.

One embodiment provides a method for calprotectin mediated inhibition of gMDSC induction in a subject in need thereof. For example, the compounds and compositions can be used to inhibit gMDSC induction in the subject. In one embodiment, the induction of gMDSCs is inhibited in the tumor microenvironment.

B. Diseases to treat

1. Cancer

The described compositions containing a compound according to Formula I or Formula II, or a pharmaceutically acceptable salt, hydrate, solvate, or derivative thereof can be administered to a subject in need thereof in an effective amount to treat inhibit, reduce to prevent cancer cell metastasis and thereby treat cancer. Cancers that may be treated by the compositions containing a compound according to Formula I or Formula II or a pharmaceutically acceptable salt, hydrate, solvate, or derivative thereof include but are not limited to breast, prostate, colon, colorectal, lung, brain, testicular, stomach, pancreas, skin, small intestine, large intestine, throat, head and neck, oral, bone, liver, bladder, kidney, thyroid and blood. Administration is not limited to the treatment of an existing tumor or infectious disease but can also be used to prevent or lower the risk of developing such diseases in an individual, i.e., for prophylactic use. Potential candidates for prophylactic treatment include individuals with a high risk of developing cancer, i.e., with a personal or familial history of certain types of cancer.

Another embodiment provides a method for reducing tumor burden in a subect in need thereof by administering an effective amount of a compound according to Formulas I-II or a pharmaceutically acceptable salt, hydrate, solvate, or derivative thereof to reduce tumor burden in the subject. Tumors which may be treated are classified herein according to the embryonic origin of the tissue from which the tumor is derived. Carcinomas are tumors arising from endodermal or ectodermal tissues such as skin or the epithelial lining of internal organs and glands. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

C. Combination Therapy

The disclosed compositions containing a compound according to Formula I or Formula II, or derivatives thereof can be administered alone or in combination with one, two, three, or more additional active agents. In some embodiments, the additional active agent is one that is known in the art for treatment of cancer, infections, or administered in combination with a vaccine, etc. The additional therapeutic agents are selected based on the condition, disorder or disease to be treated. For example, compositions for inhibiting calprotectin can be co-administered with one or more additional agents that function to enhance or promote an immune response.

For example, the disclosed compositions containing a compound according to Formula I or Formula II, or derivatives thereof can be administered with an antibody or antigen binding fragment thereof specific for a growth factor receptors or tumor specific antigens. Representative growth factors receptors include, but are not limited to, epidermal growth factor receptor (EGFR; HER1); c-erbB2 (HER2); c-erbB3 (HER3); c-erbB4 (HER4); insulin receptor; insulin-like growth factor receptor 1 (IGF-1R); insulin-like growth factor receptor 2/Mannose-6-phosphate receptor (IGF-II R/M-6-P receptor); insulin receptor related kinase (IRRK); platelet-derived growth factor receptor (PDGFR); colony-stimulating factor-1receptor (CSF-1R) (c-Fms); steel receptor (c-Kit); Flk2/Flt3; fibroblast growth factor receptor 1 (Flg/Cek1); fibroblast growth factor receptor 2 (Bek/Cek3/K-Sam); Fibroblast growth factor receptor 3; Fibroblast growth factor receptor 4; nerve growth factor receptor (NGFR) (TrkA); BDNF receptor (TrkB); NT-3-receptor (TrkC); vascular endothelial growth factor receptor 1 (Flt1); vascular endothelial growth factor receptor 2/Flk1/KDR; hepatocyte growth factor receptor (HGF-R/Met); Eph; Eck; Eek; Cek4/Mek4/HEK; Cek5; Elk/Cek6; Cek7; Sek/Cek8; Cek9; Cek10; HEK11; 9 Ror1; Ror2; Ret; Axl; RYK; DDR; and Tie.

Additional therapeutic agents include conventional cancer therapeutics such as chemotherapeutic agents, cytokines, chemokines, and radiation therapy. The majority of chemotherapeutic drugs can be divided in to: alkylating agents, antimetabolites, anthracyclines, plant alkaloids, topoisomerase inhibitors, and other antitumor agents. All of these drugs affect cell division or DNA synthesis and function in some way. Additional therapeutics include monoclonal antibodies and tyrosine kinase inhibitors e.g. imatinib mesylate (GLEEVEC® or GLIVEC®), which directly targets a molecular abnormality in certain types of cancer (chronic myelogenous leukemia, gastrointestinal stromal tumors).

Representative chemotherapeutic agents include, but are not limited to amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epirubicin, etoposide, fludarabine, fluorouracil, gemcitabine, hydroxycarbamide, idarubicin, ifosfamide, irinotecan, leucovorin, liposomal doxorubicin, liposomal daunorubicin, lomustine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine, or a combination thereof. Representative pro-apoptotic agents include, but are not limited to fludarabinetaurosporine, cycloheximide, actinomycin D, lactosylceramide, 15d-PGJ(2) and combinations thereof.

Representative alkylating agents include but are not limited to cyclophosphamide, chlorambucil, mechhlorethamine, cisplatin, oxaliplatin, carboplatin, temolozomide, melphalan, streptozocin, busulfan, bendamustine, and trabectedin. The cancer immunotherapeutic agent can be selected from the group containing alemtuzumab, trastuzumab, bevacizumab, cetuximab, ibritumomab tiuxetan, brentuximab vedotin, ado-trastuzumab emtansine, denileukin diftitox, and blinatumomab.

Representative cytotoxic/cytostatic agents include but are not limited to 5-Fluorouracil, Doxorubicin, Daunorubicin, lonidamine, altretamine, prednimustine, dibromodulcitol, ranimustine, fotemustine, nedaplatin, temozolomide, hepaplatin, estramustine, improsulfan tosilate, trofosfamide, nimustine, dibrospidium chloride, pumitepa, lobaplatin, Pemetrexed, bevacizumab, cetuximab, tositumonab, bortezomib, gefitinib, ibritumomab tiuxetan, imatinib mesylate, alemtuzumab, arsenic trioxide, gemtuzumab, temozolomide, valrubicin, tanstuzumab, capecitabine, rituximab, interferon-a, topotecan, gemcitabine, topotecan, docetaxel, tretinoin, navelbine, claribine, paclitaxel, bisantrene, mitoxantrone, and elinafide.

In a preferred embodiment, the additional therapeutic agent is cyclophosphamide. Cyclophosphamide (CPA, Cytoxan, or Neosar) is an oxazahosphorine drug and analogs include ifosfamide (IFO, Ifex), perfosfamide, trophosphamide (trofosfamide; Ixoten), and pharmaceutically acceptable salts, solvates, prodrugs and metabolites thereof (US patent application 20070202077 which is incorporated in its entirety). Ifosfamide (MITOXANAO) is a structural analog of cyclophosphamide and its mechanism of action is considered to be identical or substantially similar to that of cyclophosphamide. Perfosfamide (4-hydroperoxycyclophosphamide) and trophosphamide are also alkylating agents, which are structurally related to cyclophosphamide. For example, perfosfamide alkylates DNA, thereby inhibiting DNA replication and RNA and protein synthesis. New oxazaphosphorines derivatives have been designed and evaluated with an attempt to improve the selectivity and response with reduced host toxicity (Ref. Liang J, Huang M, Duan W, Yu X Q, Zhou S. Design of new oxazaphosphorine anticancer drugs. Curr Pharm Des. 2007; 13(9):963-78. Review). These include mafosfamide (NSC 345842), glufosfamide (D19575, beta-D-glucosylisophosphoramide mustard), S-(−)-bromofosfamide (CBM-11), NSC 612567 (aldophosphamide perhydrothiazine) and NSC 613060 (aldophosphamide thiazolidine). Mafosfamide is an oxazaphosphorine analog that is a chemically stable 4-thioethane sulfonic acid salt of 4-hydroxy-CPA. Glufosfamide is IFO derivative in which the isophosphoramide mustard, the alkylating metabolite of IFO, is glycosidically linked to a beta-D-glucose molecule. Additional cyclophosphamide analogs are described in U.S. Pat. No. 5,190,929 entitled "Cyclophosphamide analogs useful as anti-tumor agents" which is incorporated herein by reference in its entirety.

D. Treatment Regimens

The subject can be administered a first therapeutic agent 1, 2, 3, 4, 5, 6, or more hours, or 1, 2, 3, 4, 5, 6, 7, or more days before administration of a second therapeutic agent. In some embodiments, the subject can be administered one or more doses of the first agent every 1, 2, 3, 4, 5, 7, 14, 21, 28, 35, or 48 days prior to a first administration of second agent. The disclosed compositions can be the first or the second therapeutic agent.

The disclosed compositions and the additional therapeutic agent can be administered as part of a therapeutic regimen. For example, if a first therapeutic agent can be administered to a subject every fourth day, the second therapeutic agent can be administered on the first, second, third, or fourth day, or combination thereof. The first therapeutic agent or second therapeutic agent may be repeatedly administered throughout the entire treatment regimen.

Exemplary molecules include, but are not limited to, cytokines, chemotherapeutic agents, radionuclides, other immunotherapeutics, enzymes, antibiotics, growth factors, growth inhibitors, hormones, hormone antagonist, antibodies and bioactive fragments thereof (including humanized, single chain, and chimeric antibodies), antigen and vaccine formulations (including adjuvants), peptide drugs, anti-inflammatories, ligands that bind to Toll-like receptors to activate innate immune system, molecules that mobilize and optimize the adaptive immune system, other molecules that activate or up-regulate the activation of cytotoxic T lymphocytes, natural killer cells and helper T cells, and other molecules that deactivate or down-regulate suppressor or regulatory T cells.

The additional therapeutic agents are selected based on the condition, disorder or disease to be treated. For example, the disclosed compositions can be co-administered with one or more additional agents that function to enhance or promote an immune response.

EXAMPLES

General Materials and Methods:

Cell Lines and Reagents

4T1, 67NR, E0771 and EMT6 cell lines were purchased from American Type Culture Collection (ATCC). All cell lines were analyzed for *mycoplasma* contamination using MycoAlert *Mycoplasma* Detection Kit (Lonza). AT-3 cell line was a generous gift from Dr Kebin Liu (Augusta University). All cell lines were maintained in RPMI supplemented with 10% fetal bovine serum, and antibiotic/antimycotic 10,000 U ml$^{-1}$. CFSE (Invitrogen) staining was performed according to the manufacturer's instructions. Briefly, cells were washed twice in PBS, resuspended in PBS ($1\times10^7$ cells per ml) containing CFSE at a final concentration of 0.5 μM, and incubated for 10 min at room temperature. Subsequently cells were washed three times with saline and resuspended in complete medium at a concentration of $1\times10^6$ per ml. Recombinant mouse G-CSF (Shenandoah Biotechnology), SCF (Gemini Bioproducts), GM-CSF (BioLegend), IL6 (R&D Systems) were used at a final concentration of 50 ng ml$^{-1}$.

Isolation of Bone Marrow Cells

BALB/c mice were euthanized by $CO_2$ asphyxiation. The femur bones were carefully resected under sterile conditions, cleaned to remove the attached muscle/tissue, and cleaned with 70% ethanol. The bones were then transferred on to a sterile Petri dish with culture medium Roswell Park Memorial Institute (RPMI)-1640. Both ends of femurs were carefully trimmed using sterile, sharp scissors to expose the interior marrow shaft. The contents of marrow were flushed with 2-4 ml of culture medium (RPMI-1640 supplemented with 10% FBS) using 1-ml insulin syringe with a 29G×½ needle. Later, the bone marrow was flushed out onto a 70 μm nylon cell strainer placed in a 50 ml Falcon conical tube (The bones should appear white once all the marrow has been expelled out completely). The collected BM cell suspension was further diluted with 20 ml of phosphate buffer saline (PBS), and the cell suspension was centrifuged at 1,000 rpm five times. The supernatant and the cell pellet were collected using red blood cell (RBC) lysis buffer and incubated for 5 minutes. 5-10 mL of PBS was added, and the solution was centrifuged at 1,000 rpm for 5 minutes. The supernatant was discarded and the cell pellet was washed with PBS, and re-centrifuged at 1,000 rpm for 5 minutes. The cells were re-suspended with RPMI medium containing 10% FBS and used for assays or culture.

Implantation of Tumor Cells in Mice and MDSC Analysis

All mice procedures were conducted in accordance with the Institutional Animal Care and Use Committee at Augusta University. Balb/c female mice were purchased from Charles River at NCI and C57BL/6J female mice were purchased from The Jackson Laboratory.

Luciferase expressing 4T1 or EMT6 murine breast cancer cells (50,000 cells per mice) were orthotopically implanted into the fat pads of 5-week-old BALB/c mice. (AT-3 cells in C57BL/J6 mice) and these mice were imaged utilizing the Caliper IVIS imaging systems. To analyse MDSCs, tumor-bearing mice were sacrificed every week and single-cell suspensions were prepared from bone marrows, spleens, lungs and tumor tissues. Bone marrow cells were obtained by flushing bones with PBS using a 28G 1/2 syringe. Tumor and lung tissues were dissociated and digested with collagenase (Stem Cell Technologies) for 1 hr at 37° C. Red blood cells were lysed by ACK lysis buffer (Gibco).

These cells were labeled with fluorescence-conjugated Ly6C (#128015-dilution 1/400), Ly6G (#127605-dilution 1/100) and CD11b (#101208-Dilution 1/200) antibodies (Biolegend) and analyzed on a FACS canto flow cytometer (BD Biosciences).

Transcriptome Analysis and RT-PCR

To determine MDSC-induced global gene expression profile, mouse transcriptome analysis was performed. MDSC subsets derived from the primary tumor and BM of 4T1 tumor-bearing mice at 1 week post implantation were flow sorted by using Ly6C and CD11b surface antibodies. Mouse transcriptome analysis was performed either directly on the isolated MDSC subsets or after co-culturing them with murine tumor cells (Ouzounova, M., et al., *Nat Comm,* 8:14979 (2017)). Total RNA was extracted with Qiagen RNeasy Mini Kit according to the manufacturer's instructions. 500 ng of RNA was used to make cDNA using iScript cDNA synthesis kit (Biorad).

For RT-PCR analyses, KiCqStart SYBR Green predesigned primers (Sigma) were used for the following genes:

```
Vimentin
(F-5'-GCCTGCAGGATGAGATTCAGAATA-3' (SEQ ID NO: 1),

R-5'-AACCAGAGGGAGTGAATCCAGATTA-3') (SEQ ID NO: 2)

Twist
(F-5'-CGGGTCATGGCTAACGTG-3' (SEQ ID NO: 3),

R-5'-CAGCTTGCCATCTTGGAGTC-3') (SEQ ID NO: 4)

Il6
(F-5'-AAGAAATGATGGATGCTACC-3' (SEQ ID NO: 5),

R-5'-GAGTTTCTGTATCTCTCTGAAG-3') (SEQ ID NO: 6)

Il1a
(F-5'-CATAACCCATGATCTGGAAG-3' (SEQ ID NO: 7),

R-5'-ATTCATGACAAACTTCTGCC-3') (SEQ ID NO: 8)

Nos2
(F-5'-CATCAACCAGTATTATGGCTC-3' (SEQ ID NO: 9),

R-5'-TTTCCTTTGTTACAGCTTCC-3') (SEQ ID NO: 10)
```

```
-continued

Tgfb1
(F-5'-CCCTATATTTGGAGCCTGGA-3' (SEQ ID NO: 11),

R-5'-CTTGCGACCCACGTAGTAGA-3') (SEQ ID NO: 12)

Tgfb2
(F-5'-GAGATTTGCAGGTATTGATGG-3' (SEQ ID NO: 13),

R-5'-CAACAACATTAGCAGGAGATG-3') (SEQ ID NO: 14)

S100a8
(F-5'-ATACAAGGAAATCACCATGC-3', R- (SEQ ID NO: 15)

S100a9
(F-5'-CTTTAGCCTTGAGCAAGAAG-3' (SEQ ID NO: 16),

R-5'-TCCTTCCTAGAGTATTGATGG-3') (SEQ ID NO: 17)

Mmp8
(F-5'-AACTATGGATTCCCAAGGAG-3' (SEQ ID NO: 18),

R-5'-CTTTGATTGTCATATCTCCAGC-3' (SEQ ID NO: 19)

Ccl3
(F-5'-CGGAAGATTCCACGCCAATTC-3' (SEQ ID NO: 20),

R-5'-GGTGAGGAACGTGTCCTGAAG-3') (SEQ ID NO: 21),
and

Pcna
(F-5'-CTGAGGTACCTGAACTTTTTC-3' (SEQ ID NO: 22),

R-5'-TATACTCTACAACAAGGGGC-3') (SEQ ID NO: 23).
```

The relative expression mRNA level was normalized against the internal control GAPDH (F-5'-AAGGTCATC-CCAGAGCTGAA-3' (SEQ ID NO:24), R-5'-CTGCT-TCACCACCTTCTTGA-3') (SEQ ID NO:25) or ACTB (F-5'-GATGTATGAAGGCTTTGGTC-3' (SEQ ID NO:26), R-5'-TGTGCACTTTTATTGGTCTC-3') (SEQ ID NO:27) gene (ΔCt=Ct (target gene)–Ct (internal control gene)). The relative fold change was measured by 2-ΔΔCt formula compared to the control cells. Means and differences of the means with 95% confidence intervals were obtained using GraphPad Prism (GraphPad Software Inc.). Two-tailed Student's t-test was used for unpaired analysis comparing average expression between conditions. P values<0.05 were considered statistically significant.

Gene expression analysis was performed using a Nanodrop 2000 spectrophotometer (Thermo Fisher Scientific, Waltham, Mass.). The labeling, hybridization, scanning and data extraction of microarray were performed according to the recommended Affymetrix protocols. Briefly, the fluorescence signals of the microarray were scanned and saved as DAT image files. The AGCC software (Affymetrix GeneChip Command Console) transformed DAT files into CEL files to change image signals into digital signals, which recorded the fluorescence density of probes. Next, Affymetrix Expression Console software was used to pretreat CEL files through Robust Multichip Analysis (RMA) algorithm, including background correction, probeset signal integration, and quantile normalization. After pretreatment, the obtained chip files were analyzed by Affymetrix Transcriptome Analysis Console software to detect differentially expressed genes.

In vitro suppression: Multigrams of recombinant Calprotectin, S100A8 and S100A9 proteins were isolated, purified and confirmed for their activity with commercially available proteins. Bone marrow cells were treated with recombinant S100A8 (A8), S100A(9) or Calprotectin (CALP) in presence of GM-CSF (Granulocyte Macrophage-Colony Stimulating Factor Protein) in vitro for 7 days for gMDSC differentiation. The cells were then co-mixed and incubated 3 more days with activated CFSE labeled T cells.

In vivo gMDSC induction: EMT6 tumor model was selected as platform to examine the role of the proteins in regulation gMDSCs and the resultant metastatic cascade. EMT6-Luc cells were implanted into the mammary fat pads of BALB/c mice (purchased from Charles Rivers at NCI). The mice were then injected (via tail vein) either with saline (control), recombinant S100A9 or Calprotectin (100 ng/mouse) every alternate day for three weeks.

Example 1: Characterization of Murine Mammary Tumors in Syngeneic Mice

Results

To investigate the role of immune system in the metastatic process, metastatic (4T1) and less invasive (EMT6) murine mammary cell lines were used in a syngeneic (BALB/c) mouse xenograft model. Murine 4T1 cells were originally isolated from a spontaneous mammary tumor in the BALB/c strain and have been reported as metastatic and also exhibit the characteristics of human basal/triple-negative breast cancer (TNBC) subtype (Kaur, P., et al., BMC Cancer, 12:120 (2012)). In contrast, the EMT6 and 67NR murine cell lines have been shown to be less invasive (Aslakson, et al., Cancer Res, 52:1399-1405 (1992); Erin, N., et al., Oncogene, 34:3860-3870 (2014)). The tumorigenic and metastatic ability of EMT6 and 4T1 tumors were verified by injecting 50,000 cells from both lines into the mammary fat pads of mice. Both cell lines produced similarly sized tumors within 8 weeks. The 4T1 tumors showed pulmonary infiltrates as early as 1 week post implantation and developed spontaneous metastases by 5 weeks in 100% of animals (FIG. 1A-1J) and also displayed enlarged spleens size and weight (FIG. 1K-1L).

To determine whether the metastatic ability of the 4T1 murine tumors demonstrates both an epithelial-mesenchymal transition (EMT) phenotype and had cancer stem cell (CSC) properties, the CD29 and CD24 murine mammary stem cell markers were used. As determined by immunofluorescence staining and flow cytometry analyses, 4T1 cells showed higher Vimentin expression compared to the EMT6 cells under serum free culture conditions and also displayed a higher proportion of CSC as assessed by CD29+CD24+ phenotype. It was previously demonstrated that the aggressive human basal-triple-negative breast cancer (TNBC) subtype produces higher levels of inflammatory cytokines compared to other subtypes (Marotta, L. L., et al., J Clin Invest, 121:2723-2735 (2011); Kim G., et al., Oncogene, 34:671-680 (2014)). To determine whether 4T1 murine tumor cells also secrete higher levels of inflammatory cytokines, a cytokine antibody array (Ray Biotech) was used. The array demonstrated that compared to non-metastatic EMT6 or 67NR cells, metastatic 4T1 tumor cells secrete higher levels of inflammatory cytokines/chemokines including IL6, IL8, RANTES, G-CSF, GM-CSF, IL12, CXCL16, CXCL5 and VCAM (FIG. 1M-S).

Although the metastatic property of 4T1 tumor compared to EMT6 is well established in functional mouse transplantation studies, there was lack of detailed comparative gene expression analyses. Mouse transcriptome analyses were performed to compare the gene expression profile of 4T1 and EMT cell lines to their corresponding tumor xenografts grown in BALB/c mice. In comparison between 4T1 and EMT6 cells grown either in vitro or in orthotopic xenografts, 41,000 genes were identified that are differentially expressed between the in vitro cell lines versus xenografts and 781 differentially expressed genes between 4T1 and EMT6 xenografts (FIG. 1T). Among these were genes implicated in metastasis and that were expressed at higher levels in 4T1 tumors (Table 1).

TABLE 1

Upregulated genes in 4T1 xenograft.
Distinctly upregulated genes in 4T1 xenograft

| Gene | Fold change |
| --- | --- |
| KRT18 | 68.79 |
| EPCAM | 31.2 |
| MMP8 | 21.15 |
| ITGA2 | 17.91 |
| MMP1 | 15.68 |
| S100a9 | 12.32 |
| S100a8 | 11.86 |
| MMP3 | 7.39 |
| WFDC21 | 5.04 |
| CSF3 | 4.46 |
| CCL8 | 3.6 |
| LYZ1 | 3.4 |
| ICAM1 | 3.15 |
| CXCL9 | 2.98 |

Example 2: Induction and Infiltration of MDSCs by Metastatic Tumors

Results

Figure 2X:
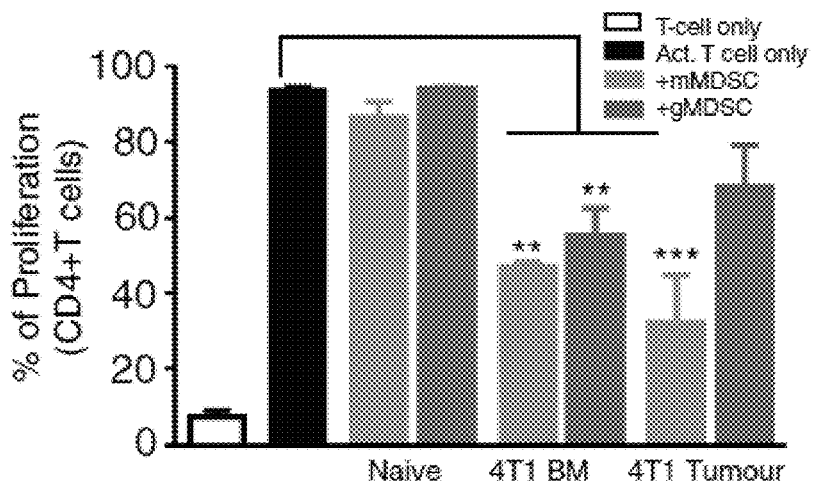
FIG. 2X is a bar graph showing % proliferation of T cells in T-cell only population (white bar), activated T cells (black bar), naïve T cells in the presence and absence of mMDSCs and gMDSCs, 4T1 bone marrow cells in the presence and absence of mMDSCs and gMDSCs, and 4T1 tumor cells in the presence and absence of mMDSCs and gMDSCs. Light gray bars represent mMDSCs and dark gray bars represent gMDSCs. The X axis represents the experimental group and the Y axis represents % proliferation of CD4+ T cells.
Figure 2Y:
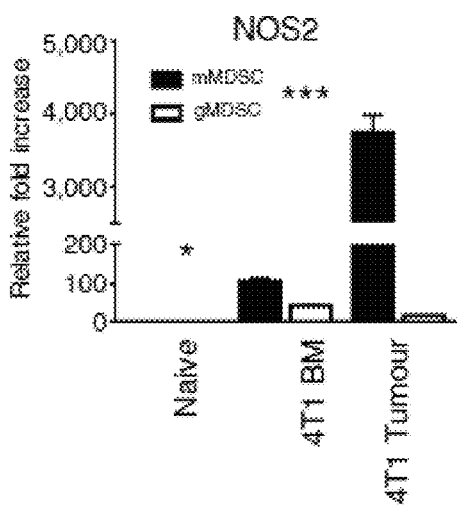
FIGS. 2Y-2Z are bar graphs showing the expression of NOS2 (FIG. 2Y) and Arg (FIG. 2Z) in naïve, 4T1 BM, and 4T1 tumor cells. Black bar represents mMDSC and white bar represents gMDSC.
Figure 2Z:
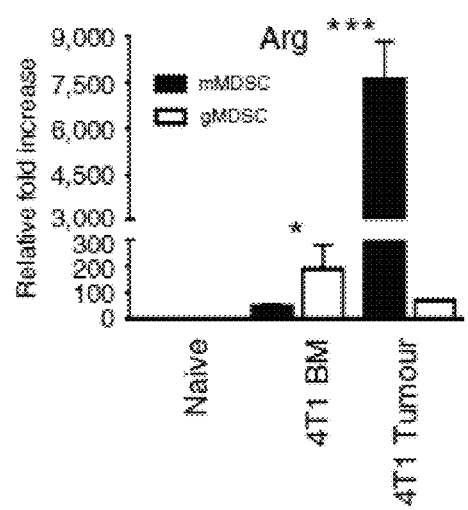

MDSCs are a heterogeneous population of immature myeloid cells with two main subsets called mMDSC and gMDSC. MDSC induction and infiltration in mouse mammary tumor models as well as the clinical setting of breast cancer have been previously reported. However, the identity of the MDSC subsets in these tumors and their molecular mechanism of interaction with the tumor remain elusive. The systemic induction and infiltration of mMDSCs and gMDSCs in primary tumor, bone marrow, spleen and lungs at weeks 1-4 post implantation of EMT6 or 4T1 tumors was investigated. Early infiltration (as early as 1 week) of mMDSCs within primary tumors and a gradual increase of gMDSCs by week 4 was detected in the 4T1 tumors (FIG. 2A-2O). Although pulmonary mMDSC infiltration was lower compared to infiltration in primary tumors of 4T1 tumor-bearing mice, pulmonary gMDSC infiltrates were increased 10-fold by week 3 (FIG. 2A-2O) preceding the detection of metastatic lesions in the lungs. Flow cytometry analyses identified that mMDSCs are characterized by CD11b$^+$ Ly6C$^{hi}$Ly6G$^-$ phenotype compared with the gMDSC subset which have a CD11b+Ly6C$^{low}$Ly6G$^+$ phenotype (FIG. 2A-2O). The findings were also verified using AT-3 tumor model in the C57BL/6J mouse strain, though with different kinetics, demonstrating a similar induction and infiltration of MDSC subsets in BM, spleen, primary tumor and lungs with different time kinetics due to differences in tumor growth rate (FIG. 2P-2W). To determine whether these MDSC subsets derived from either BM or tumor show T-cell suppression, in vitro suppression assays were performed in the presence or absence of the BM- or tumor-derived MDSC subsets from 4T1 tumor-bearing mice. As shown in FIG. 2X, tumor-derived mMDSCs showed higher levels of T-cell suppression in vitro that may be due to higher levels of nitric oxide synthase (NOS2; FIG. 2Y) and arginase 1 (ARG1; FIG. 2Z). These findings suggest that mMDSCs and gMDSCs infiltrate in the primary tumor and lungs, respectively, to promote metastasis in addition to suppressing anti-tumor immune responses.

Example 3: Induction of EMT/CSC by mMDSC at the Invasive Edge

Materials and Methods

Figure 3A:
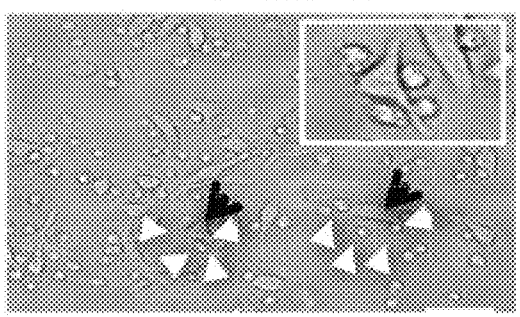
FIGS. 3A-3B are bright field images of co-cultures of EMT6 tumor cells (arrows) with mMDSC (arrowheads, FIG. 3A) or gMDSC (arrowheads, FIG. 3B) derived from 4T1 tumor-bearing mice.
Figure 3B:
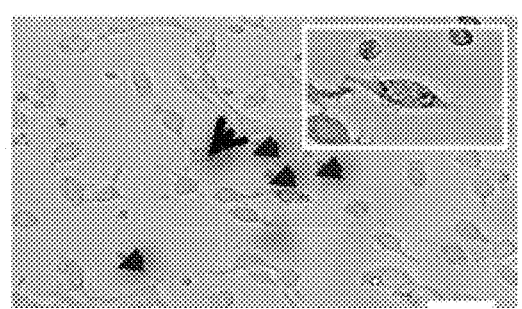
Figures 3C, 3D, 3E, 3F, 3G, 3H, 3I, 3J, 3K, 3L:
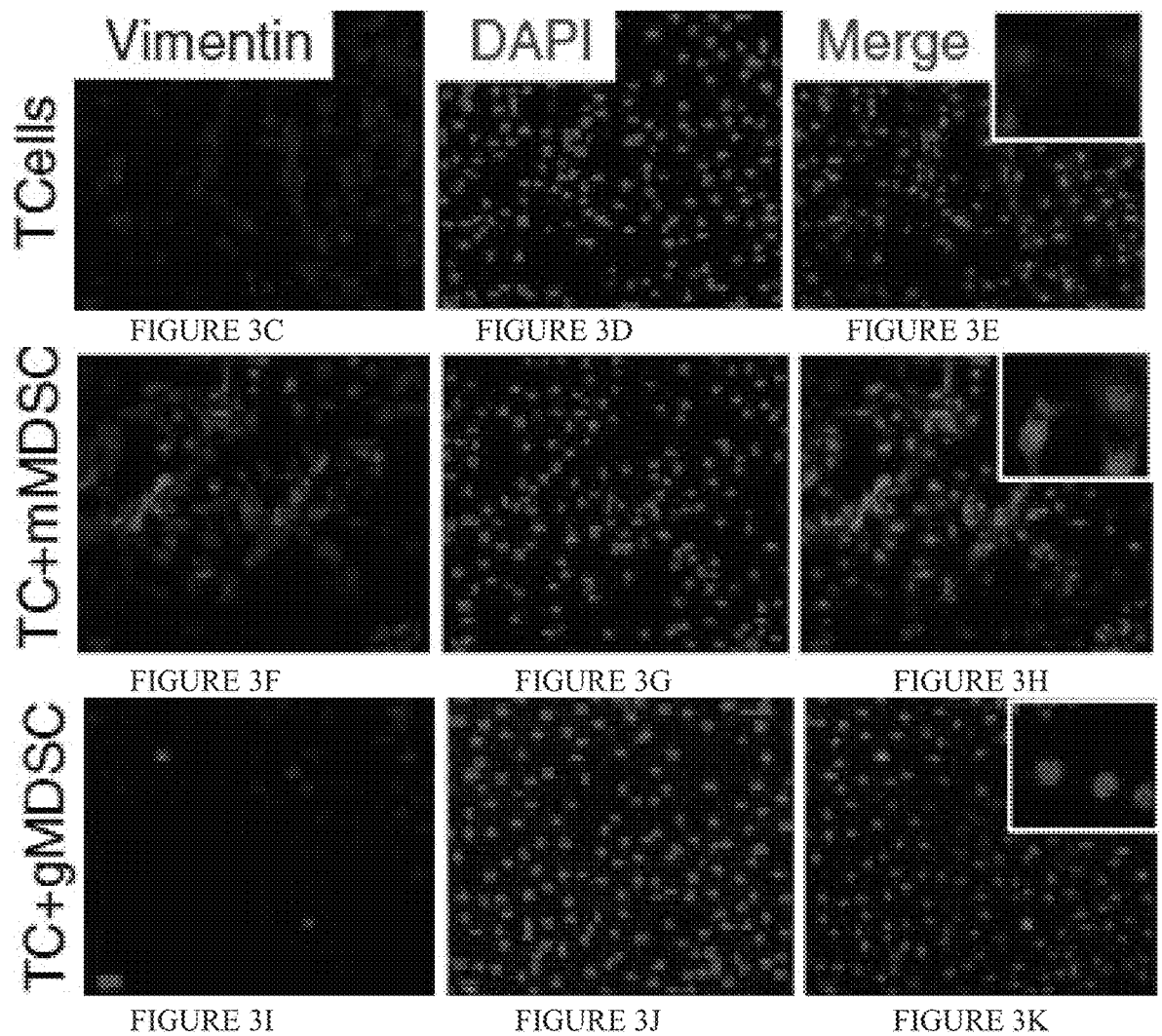
FIG. 3C-3K are fluorescence microscopy images of vimentin in T cells (FIGS. 3C-3E), T cells co-cultured with mMDSC (FIGS. 3F-3H), and T cells co-cultured with gMDSC (FIGS. 3I-3K).
FIG. 3L is a bar graph showing the percent vimetin positive cells in T cells (white bar), T cells co-cultured with mMDSC (gray bar), and T cells co-cultured with gMDSC (black bar).
Figures 3M, 3N, 3O, 3P, 3Q, 3R, 3S, 3T, 3U, 3V:
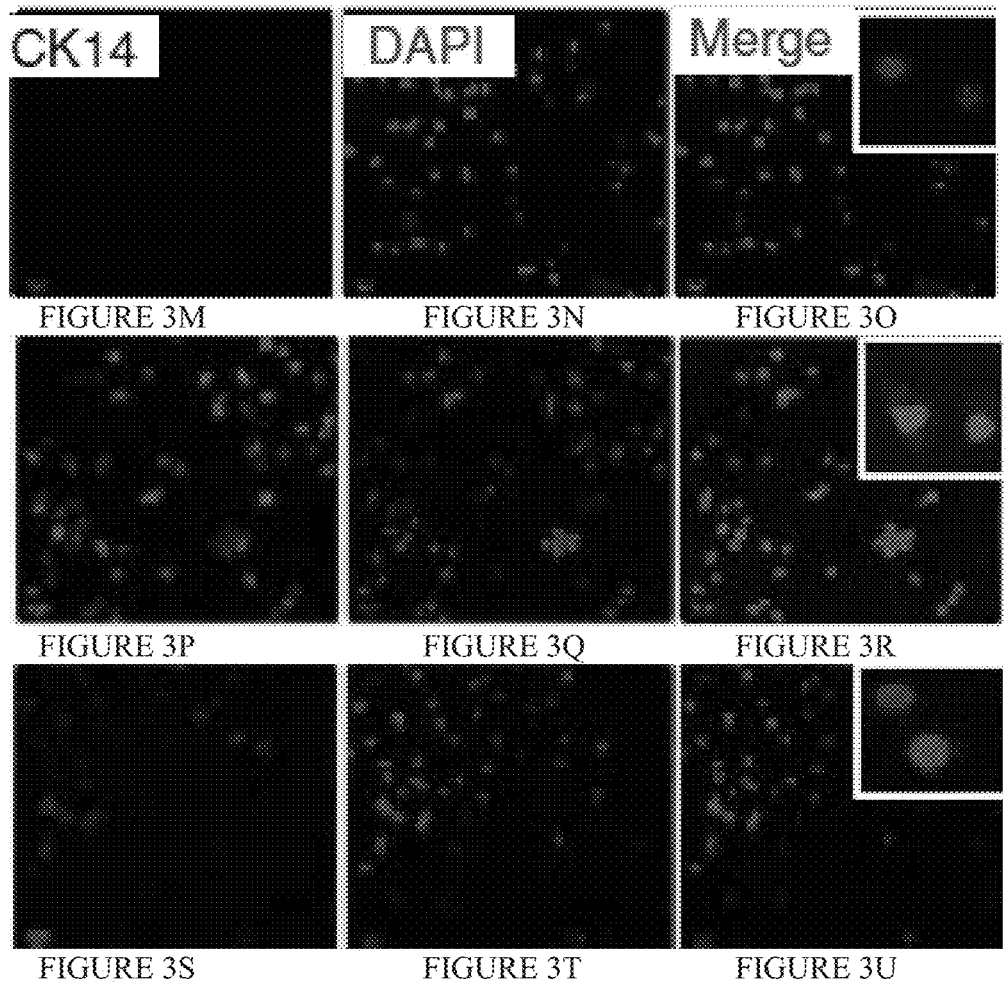
FIG. 3M-3U are fluorescence microscopy images of CK14 in T cells (FIGS. 3M-3O), T cells co-cultured with mMDSC (FIGS. 3P-3R), and T cells co-cultured with gMDSC (FIGS. 3S-3U).
FIG. 3V is a bar graph showing the percent CK14 positive cells in T cells (white bar), T cells co-cultured with mMDSC (gray bar), and T cells co-cultured with gMDSC (black bar).

Flow Cytometry Analysis:

Phenotype analyses of both mMDSCs and gMDSCs were performed using flow cytometry. To analyze MDSCs, single-cell suspensions were prepared from bone marrow, spleen, lung and tumor tissues. Bone marrow cells were obtained by flushing bones with PBS using a 28G ½ syringe. Tumor and lung tissues were dissociated and digested with collagenase (Stem Cell Technologies) for 1 hr at 37° C. Red blood cells were lysed by ACK lysis buffer (Gibco). These cells were labelled with fluorescence-conjugated Ly6C (#128015-dilution 1/400), Ly6G (#127605-dilution 1/100) and CD11b (#101208-Dilution 1/200) antibodies (Biolegend) and analyzed on a FACS canto flow cytometer (BD Biosciences). Different subsets of MDSCs were sorted with a FACS Aria cell sorter (BD Biosciences). For co-culture experiments, tumor cells were cultured either alone (control) or with 1 µM carboxyfluorescein diacetate succinimidyl ester (CFSE, Molecular probes) labelled MDSCs in 10% FBS RPMI media unless indicated otherwise for 24-48 h at the ratio of 1:1. After incubation, FITC negative tumor cells were isolated with a FACS Aria cell sorter for following experiments Results To investigate the effects of MDSC subsets on tumors, mMDSC and gMDSC subsets were independently flow sorted from the bone marrow of 4T1 tumor-bearing animals and co-cultured with the weakly metastatic EMT6 cells. As shown in FIG. 3A-3B, mMDSCs but not gMDSCs show strong affinity towards the tumor cells and induce EMT phenotype (elongated spindle-shaped morphology), which was confirmed by strong Vimentin and CK14 expressions (FIG. 3C-3V), established markers of EMT phenotype and invasion. In contrast, gMDSCs failed to induce the expression of EMT markers (FIG. 3C-3V). Analyses of EMT6 tumor-bearing animals also showed induction of MDSC subsets to a lesser degree, but they were less efficient in inducing the EMT phenotype. Molecular studies confirmed that expression of Vimentin and Twist were only upregulated by mMDSCs derived from 4T1 tumor-bearing mice compared with mMDSCs derived from EMT6 tumor-bearing animals (FIG. 3W).

To determine whether MDSCs from 4T1 tumor-bearing animals were more efficient in inducing cytokines compared with EMT6 tumor-bearing mice, the MDSC subsets from primary tumors, bone marrow and lungs of 4T1 or EMT6 tumor-bearing mice were flow-sorted and co-cultured with EMT6 tumor cells. Using a multiplex assay, MDSCs from 4T1 tumor-bearing mice were determined to be more potent in inducing the levels of cytokines in co-culture experiments compared with those from the EMT6 tumor-bearing mice It is well established that increased expression of EMT markers correlate with enhanced invasive potential of tumor cells. Consistent with this notion, invasion of EMT6 cells was enhanced when they were co-cultured with mMDSCs, while gMDSCs modestly (not significant) suppressed this process (FIG. 3X-3AA). EMT6 cells were co-cultured with mMDSCs from 4T1 tumor-bearing mice. EMT6 cells contain a small subset (41%) of CSC population as assessed by $CD24^+CD29^+$ phenotype17 but when co-cultured with mMDSCs, there was more than threefold expansion of the CSC population; co-culture with gMDSCs had no effect on CSC levels (FIG. 3BB). Expansion of the CSC population by mMDSCs was confirmed using the tumor sphere assay (FIG. 3CC).

To confirm in situ localization of MDSC subsets, formalin-fixed, paraffin-embedded tumors (at week 1) and lung sections (at week 5) from 4T1 tumor-bearing mice were analyzed using immunohistochemistry. Ly6C and Ly6G antibodies were used to identify mMDSCs and gMDSCs, respectively, Vimentin antibody as an EMT marker and Ki67 for proliferating cells. Ly6G positive cells were absent from the tumor at week 1, gMDSCs infiltrated in and around the metastatic lesions of lung at week 5 (FIG. 3DD-3OO). Vimentin expression was restricted to the invasive edge in the primary tumor where mMDSC infiltration was seen (FIG. 3DD). These Vimentin-positive cells were Ki67 negative. However, in pulmonary metastatic lesions, the majority of tumor cells were Ki67 positive and co-localized with the gMDSCs (FIG. 3JJ-3OO). Human mMDSCs are characterized by surface CD11b and CD14 expressions. To provide evidence of mMDSC infiltration in human breast cancer samples, immunohistochemical staining of 11 primary human tumor tissues was performed with the CD14 antibody. There was higher levels of CD14-positive cells detected in metastatic tumors compared to the indolent tumors (FIG. 3PP-3QQ).

Example 4: NOS2 Production by mMDSCs Induce Tumor EMT/CSC Phenotype

Results

To determine MDSC-induced global gene expression profile, mouse transcriptome analyses were performed. MDSC subsets derived from the primary tumor and BM of 4T1 tumor-bearing mice at 1 week post implantation were flow sorted by using Ly6C and CD11b surface antibodies. The mouse transcriptome analyses were performed either directly on these MDSC subsets or after co-culturing them with murine tumor cells in vitro. Results revealed that mMDSC and gMDSC subsets from BM or tumor displayed distinct gene expression profiles, with over 1,000 differentially expressed genes. Moreover, mMDSCs showed elevated expression of many EMT-related genes such as IL1a, IL6, TGFB1 and NOS2. In contrast, gMDSCs displayed expression of a different set of genes such as S100A8, S100A9, MMP8 and TGFb3 (FIG. 4A). To determine the effect of MDSC subsets on tumor cells, the gene expression profiles of tumor cells that were co-cultured with mMDSC or gMDSC subsets derived from tumor or bone marrow of 4T1 tumor-bearing mice were analyzed. Several hundred genes were differently expressed in EMT6 tumor cells when co-cultured with mMDSCs or gMDSCs (FIG. 4B-4C). Tumor cells that were co-cultured with mMDSC showed more than twofold upregulation of EMT-related genes (FIG. 4B-4C). Upregulation of these genes were confirmed by quantitative PCR (qPCR) using the indicated samples (FIG. 4D-4L). The results were independently validated by qPCR in AT-3 tumor-bearing C57BL/6J mouse model, where the same genes were upregulated in tumor cells in response to the co-culture with mMDSCs derived from AT-3 tumor-bearing animals (FIG. 4M-4U).

To determine the effect of MDSC subsets on the major signaling pathways, western blotting assay was performed on tumor cell lysates after over-night co-culture with mMDSCs or gMDSCs. Data support the gene expression analyses showing that MDSC subsets have differential effects on tumor cells. As shown in both 4T1/BALB/c and AT-3/C57BL/6J tumor models, mMDSCs induce a strong upregulation of pStat1, pStat3 and pNF-kB as well as enhanced expression of vimentin and twist in tumor cells, while sup-pressing the pERK1/2 activity (FIG. 4V-4W). In contrast, gMDSCs show enhanced pERK1/2 activity while showing no effect on pStat1 and pStat3 activation (FIG. 4V-4W).

Figures 5E, 5F, 5G, 5H:
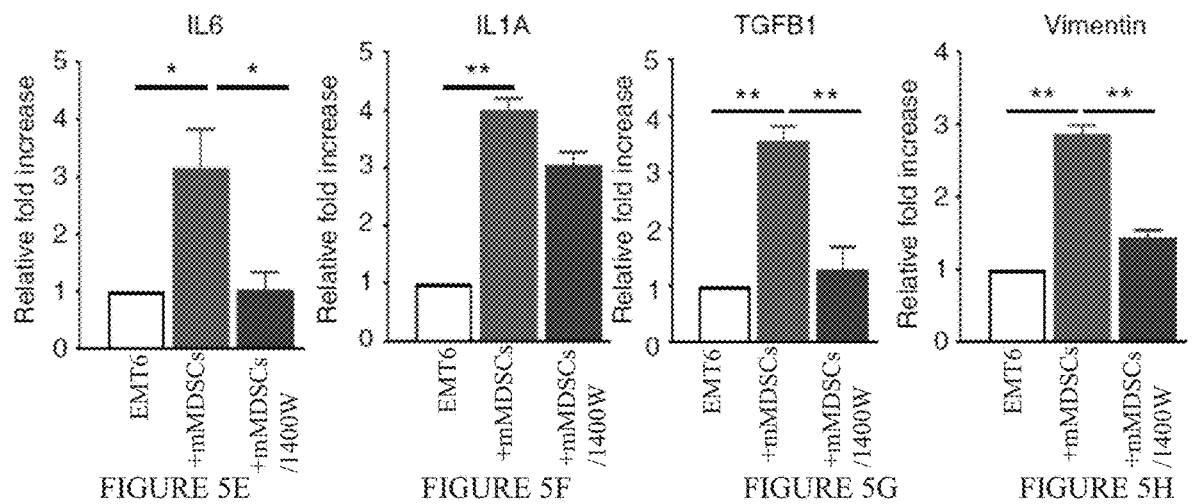
FIG. 5E-5H are bar graphs showing expression of IL6 (FIG. 5E), IL1A (FIG. 5F), TGFB (FIG. 5G), and Vimentin (FIG. 5H) in EMT6 cells (white bars), EMT6 cells+mMD-SCs (gray bars), and EMT6 cells+mMDSCs/1400W (black bar).
Figure 5I:
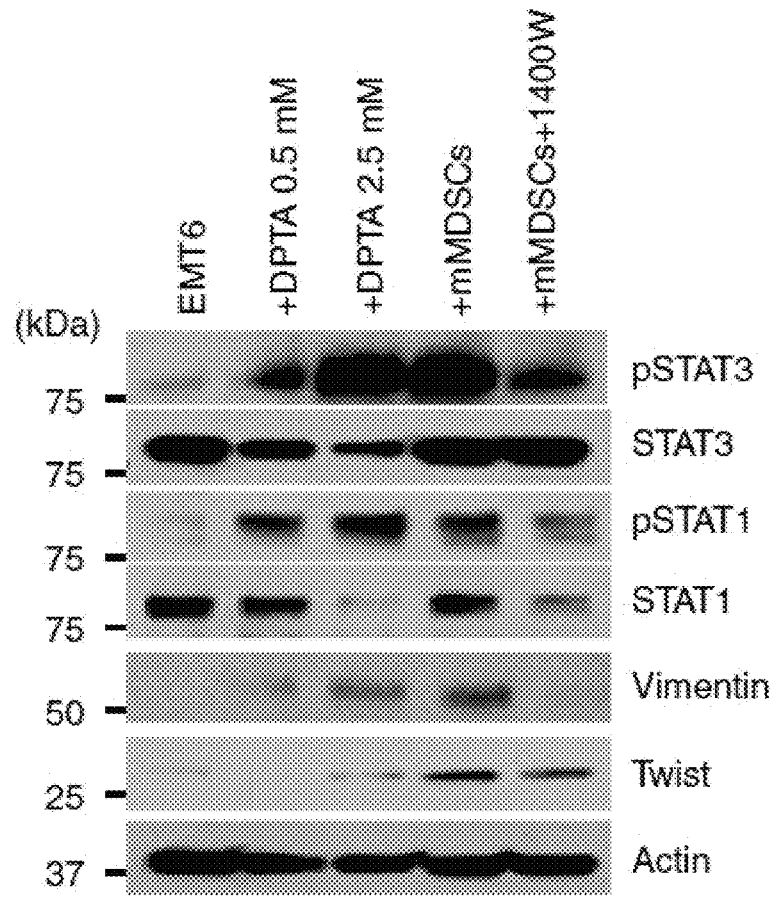
FIG. 5I is a representative Western blot showing pSTAT3, STAT3, pSTAT1, STAT1, Vimentin, Twist, and actin expression in untreated EMT6 cell, or EMT6 cells treated with 0.5 mM or 2.5 mM DPTA, mMDSCs, or mMDSCs+1400W.

Treatment of EMT6 cells with NOS2 donor, DPTA induced the expressions of indicated genes; IL1A, IL6, TGFB1 and VIM in dose-dependent manner as determined by qPCR analyses (FIG. 5A-5D). In line with these findings, NOS2 inhibitor, 1400 W was able to suppress the mMDSC-induced transcription of these genes (FIG. 5E-5H). NOS2 activation by DPTA induced the activation of pStat1 and pStat3 signaling pathways and protein levels of EMT markers, vimentin and twist, while the NOS2 inhibitor, 1,400 W suppressed the activation of the latter pathways and EMT markers (FIG. 5I).

Example 5: G-MDSCs Promote Primary and Disseminated Tumor Cell Growth

Results

The effect of MDSC subsets on tumor cell growth under in vitro co-culture conditions was examined. EMT6 tumor cells were co-cultured with mMDSC or gMDSCs from bone marrow (BM), tumor or lungs of 4T1 tumor-bearing mice. While tumor cell proliferation is enhanced by gMDSCs derived from lungs (60%) or tumor (40%), in contrast, bone-marrow-derived mMDSC or gMDSCs failed to do so (FIG. 6A-6P). Lung-derived gMDSCs also enhanced the expression of EpCAM in tumor cells in co-culture experiments (FIG. 6Q).

Figures 6R, 6S:
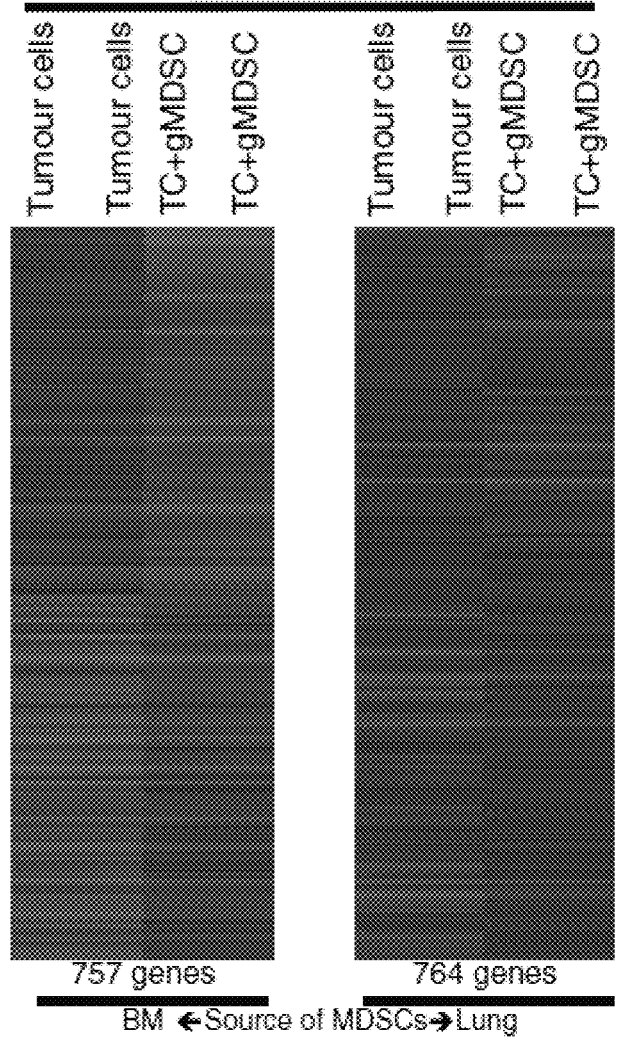
FIG. 6R-6S are heat maps showing differentially expressed genes in tumor cells co-cultured with gMDSCs.

Mouse transcriptome analysis revealed that BM or lung derived gMDSCs from 4T1 tumor-bearing animals regulate several hundred genes (757 and 764 genes, respectively) in tumor cells upon co-culture (FIG. 6R-6S). Interestingly, the top genes (S100A8, S100A9, MMP8, WFDC21, CCL3, LYZ1, FPR1 and TGFB2) that are upregulated up to several hundred fold upon co-culture with BM- or lung-derived gMDSCs. Upregulation of indicated genes as well as the proliferation marker PCNA were validated by qPCR analyses in both 4T1-BALB/c and AT-3/C57BL/6J tumor models (FIG. 6T-6QQ).

Example 6: A Murine Gene Expression Signature Predicts Poor Survival

Results

Figure 7A:
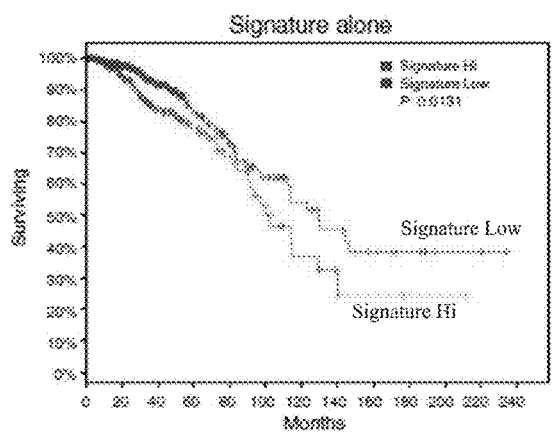
FIGS. 7A-7M are a set of survival curves from a TCGA data set of 971 breast cancer patients.
Figure 7B:
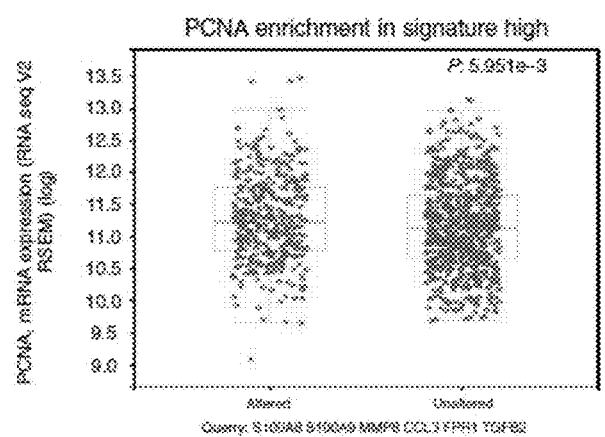
Figure 7C:
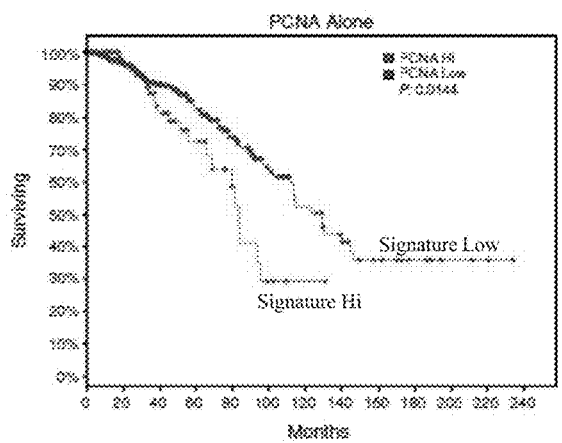
Figure 7D:
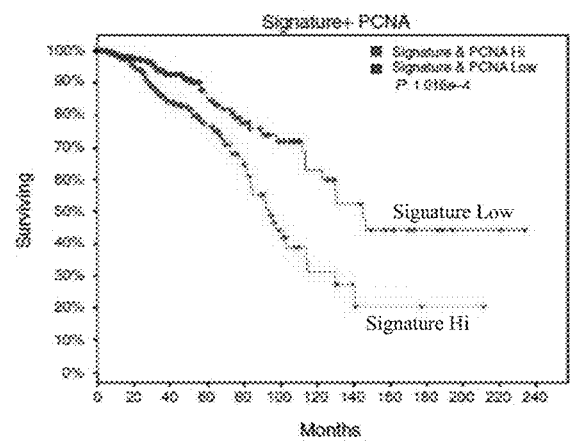
Figure 7E:
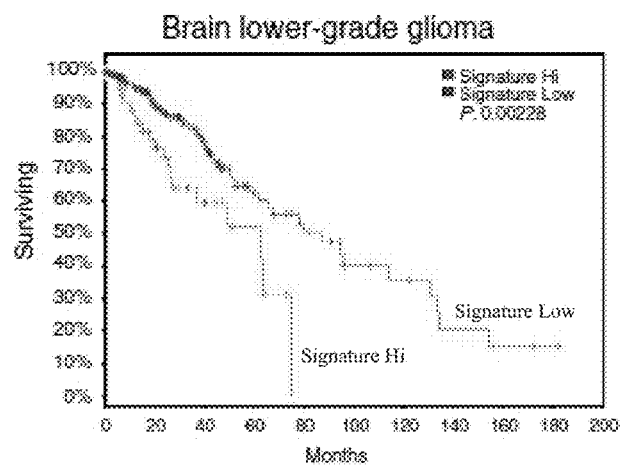
Figure 7F:
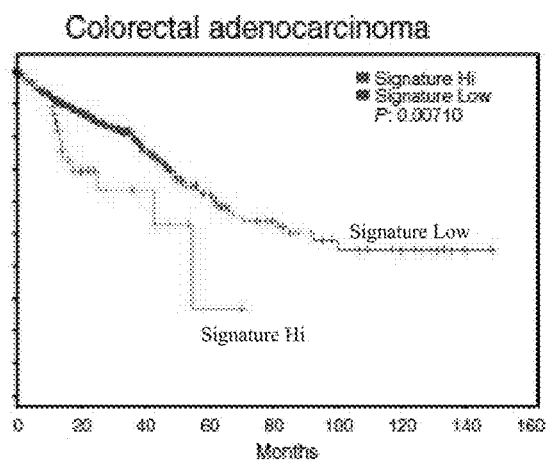
Figure 7G:
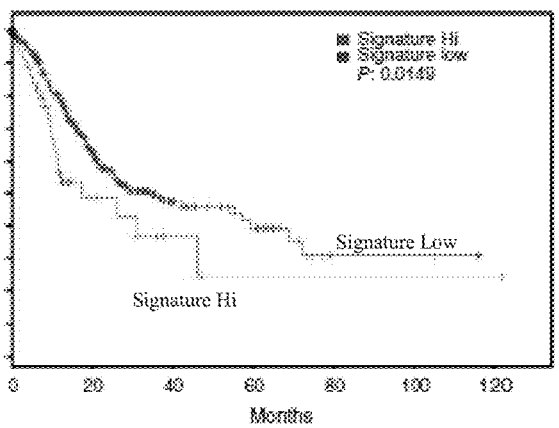
Figure 7H:
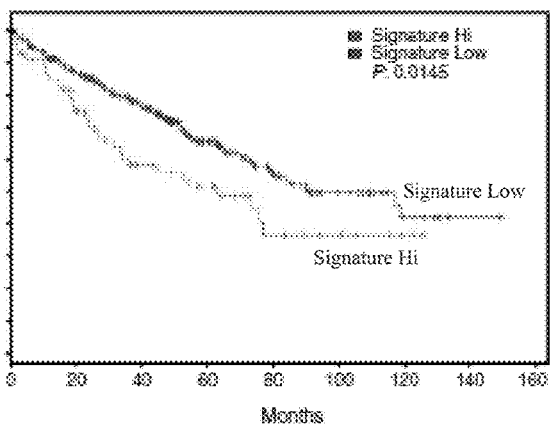
Figure 7I:
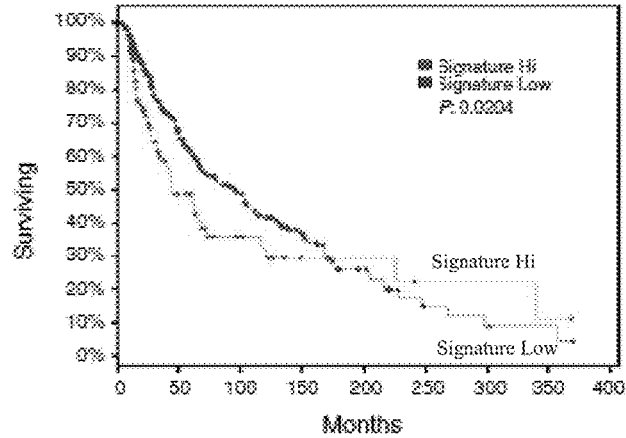
Figure 7J:
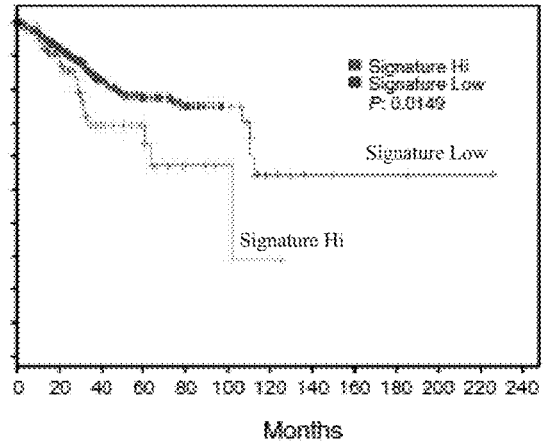
Figure 7K:
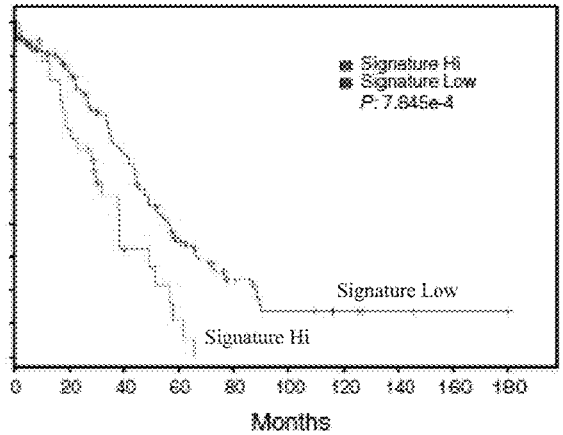
Figure 7L:
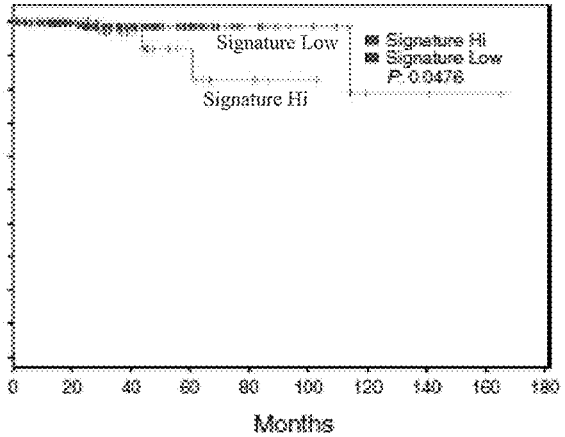
Figure 7M:
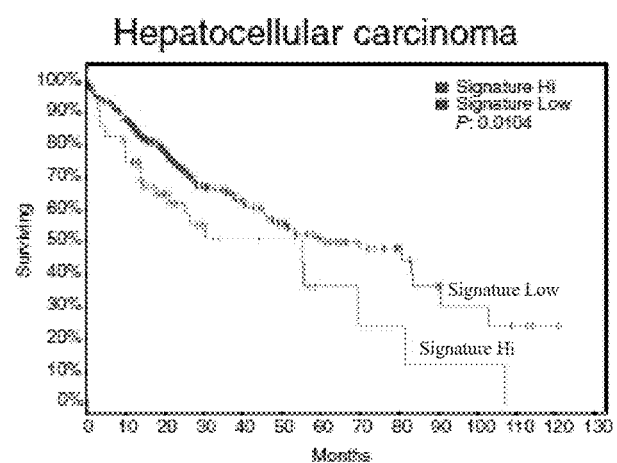

Although it is well established that EMT gene signature does not predict poor survival, ability of tumors to undergo dynamic EMT-MET transition is widely accepted to be a defining characteristic of metastatic cancers. The six genes (S100A9, MMP8, S100A8, FPR1, CCL3 and TGFB2) are referred to herein as 'metastatic gene signature' since they were particularly upregulated by lung-derived gMDSCs and are also distinctly upregulated in 4T1 xenografts compared to the 4T1 cells grown under culture conditions. The prognostic utility of the 'metastatic gene signature' in human samples was tested using the TCGA data set (TCGA, Cell 2015). This signature predicted poor survival in breast cancer patients (FIG. 7A) and also correlated with enriched PCNA expression (FIG. 7C). Moreover, the metastatic gene signature correlated with higher expression of previously reported proliferation cluster genes as 38 out of 40 genes were upregulated in patients with high metastatic signature (Table 2). Although high PCNA expression alone predicts poor survival (P=0.0144, Log-rank test) in breast cancer patients (FIG. 7B), combining PCNA and metastatic signature together improves the poor survival prediction (P=1.018e$^{-4}$, Log-rank test) in the same cancer patients (FIG. 7D). Surprisingly, the metastatic gene signature identified in mouse model-based studies was able to predict poor patient survival in 9 other solid tumors; brain lower-grade glioma (FIG. 7E), colorectal adenocarcinoma (FIG. 7F), stomach adenocarcinoma (FIG. 7G), renal cell carcinoma (FIG. 7H), cutaneous melanoma (FIG. 7I), endometrial carcinoma (FIG. 7J), ovarian serous adenocarcinoma (FIG. 7K), prostate adenocarcinoma (FIG. 7L) and hepatocellular carcinoma (FIG. 7M).

Example 7: 4T1 Tumor-Secreted Cytokines Enhance Pulmonary Metastasis

Results

Figures 8A, 8B:
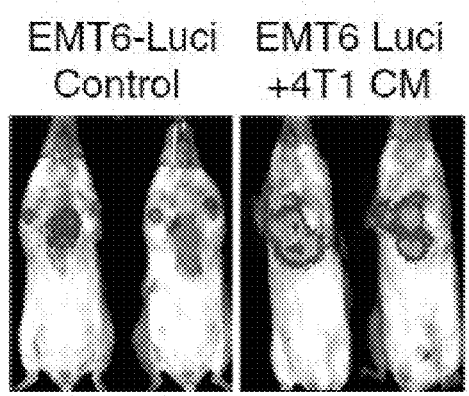
FIGS. 8A-8B are full body imaging scans of mice IV injected with EMT6-Luci cells alone or in combination with a conditioned medium from 4T1 cells.
Figure 8C:
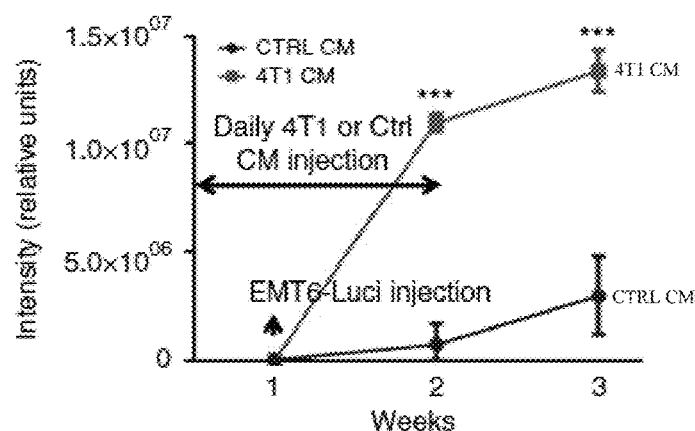
FIG. 8C is a line graph showing intensity of EMT6-Luci cells over time in the mice from FIG. 6A. (•) represents control and (■) represents 4T1 tumor conditioned medium. The X axis represents time (weeks) and the Y axis represents intensity.

EMT6-Luci cells were injected into BALB/c mice which were injected (intraperitoneally) with conditioned medium (CM) derived from 4T1 cells (FIG. 8A-8B) which resulted in enhanced EMT6-Luci lung metastasis compared to control medium injected animals. Enhanced pulmonary metastasis also correlated with the expansion of MDSCs in 4T1 CM injected animals (FIG. 8C). To further corroborate, 4T1-primed mice in which orthotopically injected 4T1 tumors were resected after 10 days were generated The metastatic ability of EMT6-Luci tumors was enhanced in 4T1-primed mice (FIG. 8E) compared to the injection in naïve mice (FIG. 8D).

Figure 9J:
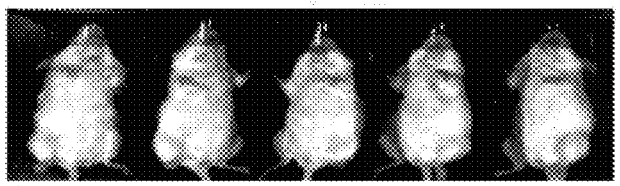
FIG. 9A-9R are full body scan images and ex vivo lung images of 4T1 tumor-injected control mice (FIGS. 9A-9I) or mice treated with anti-Ly6g antibody to deplete gMDSCs (FIGS. 9J-9R).
FIG. 9S is a line graph showing luciferase intensity over time in isotype control (•) and anti-Ly6G (■) mice from FIG. 9A-9B. The X axis represents time (days) and the Y axis represents luciferase intensity.
FIG. 9T is a bar graph showing lung gMDSCs in isotype control (black bars) and anti-Ly6G (white bars). The Y axis represents % of Ly6G+CD11b+ cells.
Figure 9K:
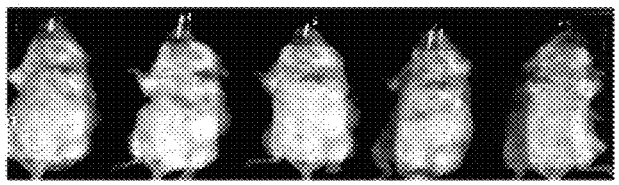
Figure 9L:
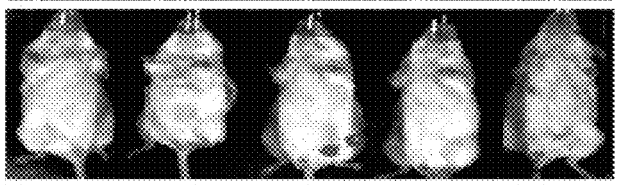
Figure 9M:
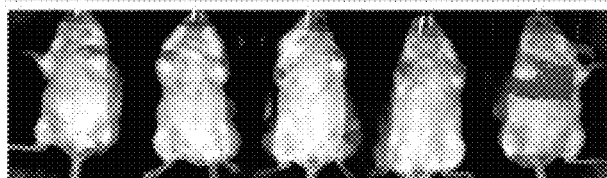
Figures 9N, 9O, 9P, 9Q, 9R:
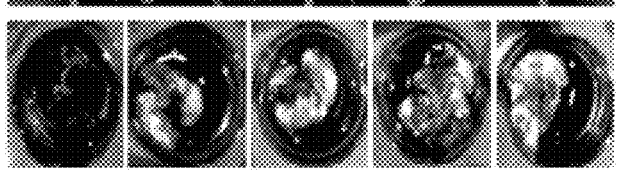
Figure 9S:
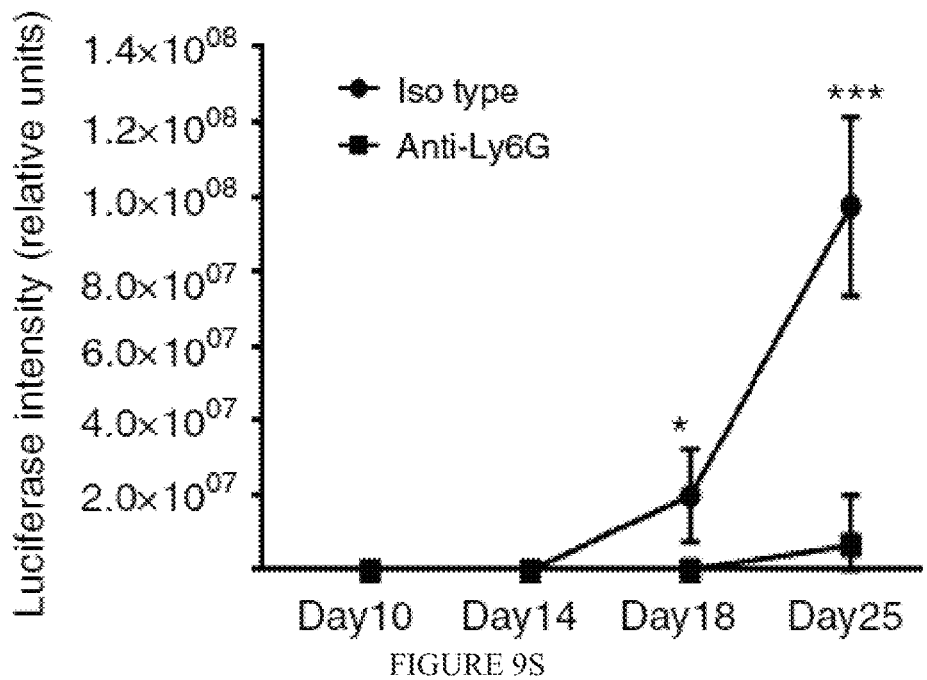

To determine the direct role of MDSC subsets in pulmonary metastasis, 4T1-luci cells were injected either alone or combined with lung-derived mMDSCs or gMDSCs isolated from 4T1 tumor-bearing mice. There was an enhanced pulmonary metastasis and shortened survival when 4T1-luci cells were injected in combination with gMDSCs compared to the 4T1-luci alone or combination with mMDSCs (FIG. 8F-8N) supporting the findings that gMDSCs promote tumor growth. To further support these findings, gMDSCs were depleted in 4T1 tumor-bearing mice. Mice injected with 4T1 tumor cells (10,000 cells) via tail vein developed pulmonary metastasis (4 out of 5 mice) within 2-3 weeks (FIG. 9A-9I), however, depletion of gMDSCs using anti-Ly6g antibody resulted in suppression of pulmonary metastasis (1 out 5 mice; FIG. 9J-9R) via reducing the infiltration of gMDSCs in the lungs (FIG. 9S-9T). Ex vivo lung images clearly show the difference of metastatic growth between control and Ly6G-antibody treated groups.

Example 8: Lung gMDSCs Promote the Growth of Disseminated Tumor Cells

Results

A mouse model in which orthotopically (fat pads) implanted tumors were resected at 1 week post implantation was developed. Despite the presence of disseminated tumor cells in regional lymph nodes and lungs, there was no metastatic growth up to 12 weeks of follow up (FIG. 10A-10E). In contrast, the majority of animals developed metastasis when the primary tumors were resected at 2 weeks post implantation (FIG. 10F-10H). These findings provided further evidence that infiltration of gMDSCs in the secondary organs is required for successful metastasis. As shown in FIG. 2, expansion and infiltration of gMDSCs in lungs occur at 2 weeks post implantation. This model may offer a great utility for investigation of the disseminated tumor cells in the absence of primary tumors as shown in the experimental outline (FIG. 10I). This model was utilized to evaluate the functional role of gMDSCs. In three groups of mice, luciferase-tagged primary tumors were resected at 1 week post implantation. First control group were not treated after resection (FIG. 10J-10K), second group were injected twice with tumor-derived mMDSCs (250 K per mice by tail vein; FIG. 10L-10M) and third group were injected twice with lung-derived gMDSCs (250 K per mice by tail vein; FIG. 10N-10P) isolated from 4T1 tumor-bearing animals. First and second group of mice were followed up for metastatic growth by bioluminescence imaging (BLI) up to 11 weeks without any detectable metastasis (FIG. 10J-10M). In contrast, 3 out of 4 mice injected with lung-derived gMDSCs developed metastasis (FIG. 10N-10Q). Collectively, this data suggests that dissemination and metastatic colonization/growth are two independent steps in the metastatic cascade and may be regulated by different subsets of MDSCs as depicted by the illustration of the working hypothesis (FIG. 10R).

Example 9: Calprotectin Promotes Metastasis by Inducing gMDSCs

Figure 11A:
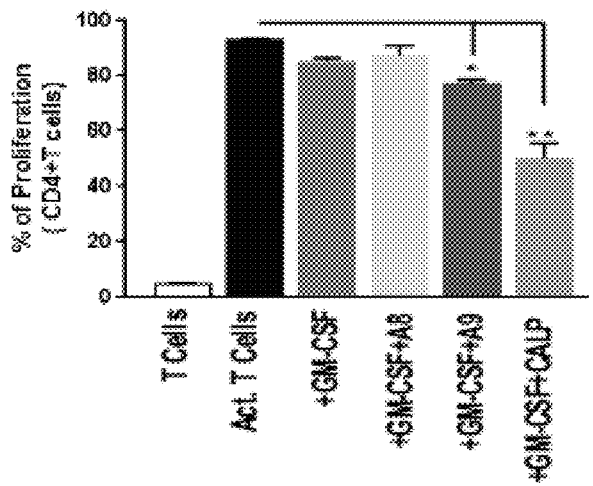
FIG. 11A is a bar graph showing percent proliferation of bone marrow derived T cells either unactivated (white bar) or activated (black bar) and treated with GM-CSF (medium gray bar), GM-CSF+A8 (light gray bar), GM-CSF+A9 (dark gray bar), or GM-CSF+CALP (medium light gray bar).

Materials and Methods
In Vitro Suppression:
Multigrams of recombinant Calprotectin, S100A8 and S100A9 proteins were isolated, purified and confirmed for their activity with commercially available proteins. Bone marrow cells were treated with recombinant S10A8 (A8), S100A(9) or Calprotectin (CALP) in presence of GM-CSF (Granulocyte Macrophage—Colony Stimulating Factor Protein) in vitro for 7 days for gMDSC differentiation. The cells were then co-mixed and incubated 3 more days with activated CFSE labeled T cells.
In Vivo gMDSC Induction:
EMT6 tumor model was selected as platform to examine the role of the proteins in regulation gMDSCs and the resultant metastatic cascade. EMT6-Luc cells were implanted into the mammary fat pads of BALB/c mice (purchased from Charles Rivers at NCI). The mice were then injected (via tail vein) either with saline (control), recombinant S100A9 or Calprotectin (100 ng/mouse) every alternate day for three weeks.
Results
Calprotectin treated gMDSCs suppressed T cell proliferation more efficiently compared to S100A9, while S100A8 had no significant effect (FIG. 11A). Calprotectin treated mice showed an enhanced primary tumor growth and spontaneous metastasis to the lungs and liver (FIG. 11B-11K). Calprotectin treated mice also showed an increase in CD8+ T cells (FIG. 11L). T cells from calprotectin treated mice significantly suppressed the tumor cell killing activity compared to control treated mice, while T cells from S100A9 treated mice had moderate activity (FIG. 11M). The levels of caspase 3 mediated apoptosis were reduced in S100A9 and calprotectin treated mice (FIG. 11N).

Example 10: Elevated Levels of Calprotectin in Animals and Patients with Tumor Metastasis Materials and Methods
Blood samples were collected from mice bearing EMT6 and 4T1 tumor bearing mice at weeks 1-2 post implantation via tail vein. Circulating Calprotectin levels were measured using ELISA. Similarly, blood samples from human patients with various stages of breast cancer were collected and measured for circulating Calprotectin levels.

Figures 12A, 12B:
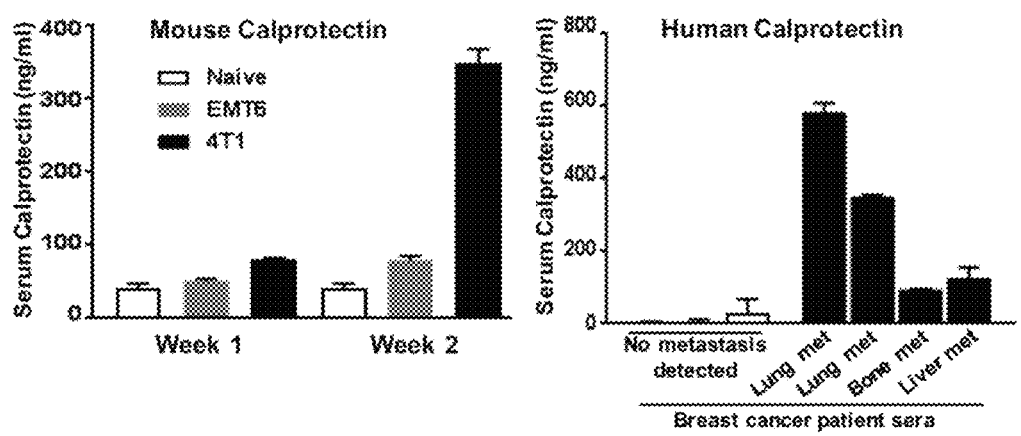
FIG. 12A is a bar graph showing calprotectin levels in serum from naïve mice (white bars), EMT6 mice (gray bars), and 4T1 tumor-bearing mice (black bars) one or two weeks after tumor implantation. The X-axis represents time (weeks) and the Y-axis represents serum calprotectin (ng/ml).
FIG. 12B is a bar graph showing serum calprotectin levels in breast cancer patients with various levels of metastases. The X-axis represents the metastatic status of the breast cancer patient and the Y-axis represents serum calprotectin (nm/ml).

Results
4T1 tumor bearing mice showed a gradual and significant upregulation of serum calprotectin compared with EMT6 tumor bearing mice (FIG. 12A). Similarly, circulating calprotectin levels were found elevated in human patients with metastatic breast cancer compared to patients with indolent tumors (FIG. 12B).

Example 11: Screening and Functional Characterization of Lead NCI Compounds

Figure 13A:
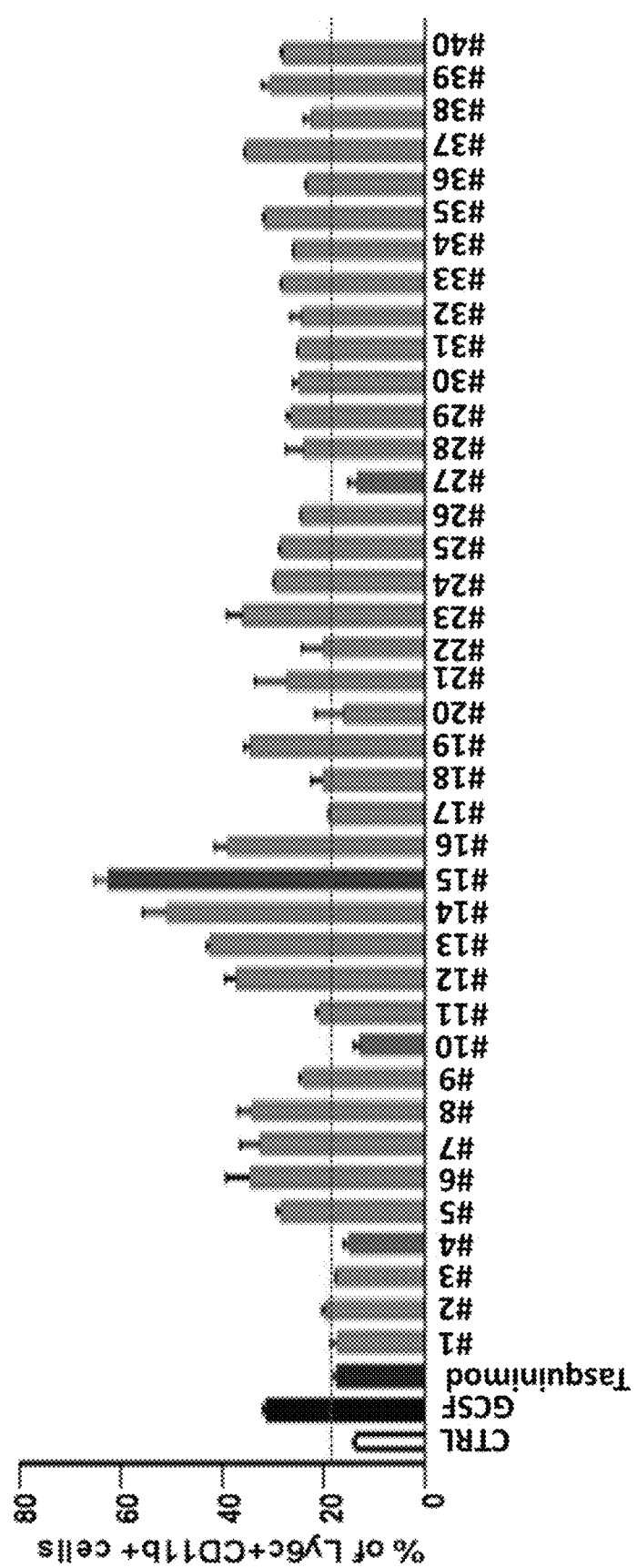
FIG. 13A is a bar graph showing Ly6c+Ly6g+CD11b+ gMDSCs differentiation in vitro in bone marrow cells treated with GCSF and the lead NCI compounds identified by computational screen against S100A8/A9 (calprotectin).

Materials and Methods
Drug Screening:
Computational screening of certain select NCI chemical library was performed again the crystal structure of calprotectin. 40 lead compounds were identified with potential to bind to calprotectin and suppress gMDSC differentiation. In vitro screening using the 40 lead compounds was performed. Bone marrow cells were counted using hemocytometer or Beckman Z2 coulter counter and suspended in culture medium (RPMI 1640+10% FBS+1% penicillin/streptomycin) to achieve a final cell density of 2×106 BM cells/well. T20 ng/mL of recombinant mouse GM-CSF (Granulocyte Macrophage—Colony Stimulating Factor Protein) was added followed by 50 ng/mL G-CSF or individual selected drug. The cells were incubated at 37° C., under 5% CO2 and 95% humidity in $CO_2$ incubator for 3 days. The BM cells were then pipetted into the FACS tubes, followed by addition of 1 mL PBS, and centrifuged at 1000 rpm for 5 minutes. The supernatant was removed and the cells were re-suspended with 100 ml 2% FBS+PBS, and fluorescent labeled antibodies and isotype control. The cells were set for 30 minutes at 4° C. in dark to allow proper staining with PBS. 0.5 ml of PBS was added in each FACS tube and flow cytometry analysis was performed. (the mouse markers used for analysis are: For total MDSCs—Gr1+CD11b+; Monocytic MDSCs—LY6CHiLY6G-CD11b+; Granulocytic MDSCs: LY6CMid/−LY6G+CD11b+).
Suppressive Assay:
Bone marrow cells were treated with recombinant Calprotectin (CALP) in presence of GM-CSF (Granulocyte Macrophage—Colony Stimulating Factor Protein), and compound #4 or #10, in vitro for 7 days for gMDSC differentiation. The cells were then co-mixed and incubated 3 more days with activated CFSE labeled T cells.
Results
FIG. 13A shows gMDSC induction by 40 compounds identified from NCI library in comparison to G-CSF. Out of the 40 compounds, compounds number #4 (NSC37627), #10 (NSC60785), and #27 (NSC135168) showed significant inhibition of gMDSC differentiation (FIG. 13B-13K). Drug #4 and drug #10 reduced the expression of MDSC-related genes S100A8, S100S9, GCSF, IL1A, NOS2, CYBB1, and IL4R (FIG. 13L-13R).
FIGS. 14A-14D show that compound #10 suppresses tumor growth and metastasis in 4T1-injected mice. FIGS. 14E-14L show that drug #10 can reduce gMDSC infiltration into the tumor and distant organ sites.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or

We claim:

1. A method for inhibiting or reducing cancer cell metastasis in a subject in need thereof comprising administering to the subject a composition comprising at least one calprotectin inhibitor, in an amount effective to inhibit or reduce cancer cell metastasis, and a pharmaceutically acceptable excipient.

2. The method of claim 1, wherein the calprotectin inhibitor is NSC37627, NSC60785, or NSC727038.

3. The method of claim 1, further comprising administering to the subject a second cancer therapeutic selected from the group consisting of alkylating agents, cancer immunotherapeutic agents, chemotherapeutics, or cytotoxic/cytostatic agents.

4. The method of claim 3, wherein the alkylating agent is selected from the group consisting of cyclophosphamide, chlorambucil, mechhlorethamine, cisplatin, oxaliplatin, carboplatin, temolozomide, melphalan, streptozocin, busulfan, bendamustine, and trabectedin.

5. The method of claim 3, wherein the cancer immunotherapeutic agent is selected from the group consisting of alemtuzumab, trastuzumab, bevacizumab, cetuximab, ibritumomab tiuxetan, brentuximab vedotin, ado-trastuzumab emtansine, denileukin diftitox, and blinatumomab.

6. The method of claim 3, wherein the cytotoxic/cytostatic agent is selected from the group consisting of 5-Fluorouracil, doxorubicin, daunorubicin, lonidamine, altretamine, prednimustine, dibromodulcitol, ranimustine, fotemustine, nedaplatin, temozolomide, hepaplatin, estramustine, improsulfan tosilate, trofosfamide, nimustine, dibrospidium chloride, pumitepa, lobaplatin, pemetrexed, bevacizumab, cetuximab, tositumonab, bortezomib, gefitinib, ibritumomab tiuxetan, imatinib mesylate, alemtuzumab, arsenic trioxide, gemtuzumab, temozolomide, valrubicin, tanstuzumab, capecitabine, rituximab, interferon-a, topotecan, gemcitabine, topotecan, docetaxel, tretinoin, navelbine, claribine, paclitaxel, bisantrene, mitox-antrone, and elinafide.

7. The method of claim 1, wherein the effective amount of calprotectin inhibitor inhibits the induction of gMDSCs in the tumor microenvironment of the subject.

8. The method of claim 1, wherein the cancer is selected from the group consisting of bladder, brain, cervical, colorectal, esophageal, kidney, liver, lung, nasopharangeal, pancreatic, prostate, skin, stomach, uterine, ovarian, testicular and hematologic cancers.

9. The method of claim 1, wherein the cancer is pre-metastatic.

10. The method of claim 1, wherein the cancer is metastatic.

11. The method of claim 1, wherein the composition is administered parenterally.

12. The method of claim 1, wherein the composition is administered enterally.

13. A method for reducing tumor size or tumor burden in a subject in need thereof, comprising administering to the subject an effective amount of a pharmaceutical composition containing a calprotectin inhibitor.

14. The method of claim 13, further comprising administering cyclophosphamide in combination or alternation with the pharmaceutical composition.

15. A method for inhibiting or reducing breast cancer cell metastasis in a subject in need thereof comprising administering to the subject a composition comprising at least one calprotectin inhibitor, in an amount effective to inhibit or reduce cancer cell metastasis, and a pharmaceutically acceptable excipient.

* * * * *